(12) United States Patent (10) Patent No.: US 7,594,594 B2
Troost et al. (45) Date of Patent: *Sep. 29, 2009

(54) MULTI-COMPARTMENT STORAGE AND DELIVERY CONTAINERS AND DELIVERY SYSTEM FOR MICROENCAPSULATED FRAGRANCES

(75) Inventors: Erik Herman Troost, Amsterdam (NL); Joseph Brain, Bussum (NL); Lewis Michael Popplewell, Morganville, NJ (US); Kaiping Lee, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 682 days.

This patent is subject to a terminal disclaimer.

(21) Appl. No.: 10/991,048

(22) Filed: Nov. 17, 2004

(65) Prior Publication Data

US 2006/0102656 A1 May 18, 2006

(51) Int. Cl.
*B67D 5/60* (2006.01)
(52) U.S. Cl. .................. 222/145.5; 222/132; 222/212; 206/219
(58) Field of Classification Search ... 222/145.4–145.6, 222/132, 206, 212–215, 481.5; 206/219; 512/4; 510/303
See application file for complete search history.

(56) References Cited

U.S. PATENT DOCUMENTS

| | | | |
|---|---|---|---|
| 2,661,870 A | 12/1953 | Huenergardt | |
| 2,800,457 A | 7/1957 | Green et al. | |
| 2,941,696 A | 6/1960 | Homm | |
| 2,973,883 A | 3/1961 | Modderno | |
| 3,041,288 A | 6/1962 | Anthony | |
| 3,269,389 A | 8/1966 | Meurer et al. | |
| 3,415,758 A | 12/1968 | Powell et al. | |
| 3,416,709 A | 12/1968 | Schultz et al. | |
| 3,505,432 A | 4/1970 | Neuwald | |
| 3,516,846 A | 6/1970 | Matson | |
| 3,516,941 A | 6/1970 | Matson | |

(Continued)

FOREIGN PATENT DOCUMENTS

DE 101 09 063 A1 9/2002

(Continued)

OTHER PUBLICATIONS

Lochhead, et al, Encyclopedia of Polymers and Thickeners for Cosmetics, Cosmetics & Toiletries, vol. 108, May 1993, pp. 95-138.

(Continued)

*Primary Examiner*—Frederick C. Nicolas
(74) *Attorney, Agent, or Firm*—Elizabeth M. Quirk; XuFan Tseng; Joseph F. Leightner

(57) ABSTRACT

Described is a multiple (2-4)-compartment fluidic individually stable pre-storable composition storage and unstable mixture-forming and delivery container having separate compartments each communicating with a single mixing zone via an externally-located fluidic composition multiple delivery tube system juxtaposed with the outer surfaces of the compartment walls. These containers are well suited for storing and transporting compositions such as a cleaning agent composition, a personal care composition, an aqueous liquid detergent composition and/or a fabric softening composition and then promptly delivering the resulting unstable mixture to the desired location. The container has been advantageously found to deliver unstable mixtures which could include aqueous suspensions of microencapsulated fragrances or other ingredients.

11 Claims, 25 Drawing Sheets

U.S. PATENT DOCUMENTS

| | | | |
|---|---|---|---|
| 3,686,025 A | 8/1972 | Morton |
| 3,760,986 A | 9/1973 | Castner et al. |
| 3,861,870 A | 1/1975 | Edwards et al. |
| 3,870,542 A | 3/1975 | Ida et al. |
| 4,081,384 A | 3/1978 | Pracht |
| 4,082,223 A | 4/1978 | Nozawa |
| 4,124,521 A | 11/1978 | Jedzinak |
| 4,145,184 A | 3/1979 | Brain et al. |
| 4,206,816 A | 6/1980 | Richardson et al. |
| 4,209,417 A | 6/1980 | Whyte |
| 4,234,627 A | 11/1980 | Schilling |
| 4,247,498 A | 1/1981 | Castro |
| 4,318,818 A | 3/1982 | Letton et al. |
| 4,387,090 A | 6/1983 | Bolich, Jr. |
| 4,395,541 A | 7/1983 | Jacquet et al. |
| 4,402,856 A | 9/1983 | Schnoring et al. |
| 4,406,816 A | 9/1983 | Sliwka |
| 4,424,134 A | 1/1984 | Sissin et al. |
| 4,428,869 A | 1/1984 | Munteanu et al. |
| 4,446,032 A | 5/1984 | Munteanu et al. |
| 4,446,042 A | 5/1984 | Leslie |
| 4,464,271 A | 8/1984 | Munteanu et al. |
| 4,496,467 A | 1/1985 | Munteanu et al. |
| 4,514,461 A | 4/1985 | Woo |
| 4,515,705 A | 5/1985 | Moeddel |
| 4,521,541 A | 6/1985 | Rutherford et al. |
| 4,528,180 A | 7/1985 | Schaeffer |
| 4,534,891 A | 8/1985 | Boden et al. |
| 4,537,706 A | 8/1985 | Severson, Jr. |
| 4,537,707 A | 8/1985 | Severson, Jr. |
| 4,539,135 A | 9/1985 | Ramachandran et al. |
| 4,550,862 A | 11/1985 | Barker et al. |
| 4,561,998 A | 12/1985 | Wertz et al. |
| 4,585,150 A | 4/1986 | Beacham et al. |
| 4,597,898 A | 7/1986 | Vander Meer |
| 4,597,962 A | 7/1986 | Grollier et al. |
| 4,673,568 A | 6/1987 | Grollier et al. |
| 4,681,806 A | 7/1987 | Matkan et al. |
| 4,687,663 A | 8/1987 | Schaeffer |
| 4,705,681 A | 11/1987 | Maes et al. |
| 4,708,267 A | 11/1987 | Sieverding et al. |
| 4,714,562 A | 12/1987 | Roselle et al. |
| 4,731,243 A | 3/1988 | Lindauer et al. |
| 4,767,547 A | 8/1988 | Straathof et al. |
| 4,819,835 A | 4/1989 | Tasaki |
| 4,826,048 A | 5/1989 | Skorka et al. |
| 4,830,855 A | 5/1989 | Stewart |
| 4,858,758 A | 8/1989 | Mitchell et al. |
| 4,917,920 A | 4/1990 | Ono et al. |
| 4,961,871 A | 10/1990 | Michael |
| 4,968,451 A | 11/1990 | Scheibel et al. |
| 4,973,422 A | 11/1990 | Schmidt |
| 5,066,419 A | 11/1991 | Walley et al. |
| 5,085,857 A | 2/1992 | Reid et al. |
| 5,112,688 A | 5/1992 | Michael |
| 5,137,646 A | 8/1992 | Schmidt et al. |
| 5,154,842 A | 10/1992 | Walley et al. |
| 5,160,655 A | 11/1992 | Donker et al. |
| 5,169,552 A | 12/1992 | Wise |
| 5,188,753 A | 2/1993 | Schmidt et al. |
| 5,194,639 A | 3/1993 | Connor et al. |
| D336,846 S | 6/1993 | Proctor |
| 5,232,769 A | 8/1993 | Yamato et al. |
| 5,237,035 A | 8/1993 | O'Lenick, Jr. et al. |
| 5,252,312 A | 10/1993 | Gentile et al. |
| 5,275,755 A | 1/1994 | Sebag et al. |
| 5,288,417 A | 2/1994 | Bauer et al. |
| 5,288,431 A | 2/1994 | Huber et al. |
| 5,403,499 A | 4/1995 | Kiefer et al. |
| 5,411,671 A | 5/1995 | Bauer et al. |
| 5,458,809 A | 10/1995 | Fredj et al. |
| 5,458,810 A | 10/1995 | Fredj et al. |
| 5,460,752 A | 10/1995 | Fredj et al. |
| 5,460,805 A | 10/1995 | Davis et al. |
| 5,466,802 A | 11/1995 | Panandiker et al. |
| 5,470,507 A | 11/1995 | Fredj et al. |
| 5,500,138 A | 3/1996 | Bacon et al. |
| 5,534,197 A | 7/1996 | Scheibel et al. |
| 5,540,853 A | 7/1996 | Trinh et al. |
| 5,545,340 A | 8/1996 | Wahl et al. |
| 5,545,350 A | 8/1996 | Baker et al. |
| 5,559,261 A | 9/1996 | Sivik |
| 5,562,849 A | 10/1996 | Wahl et al. |
| 5,565,145 A | 10/1996 | Watson et al. |
| 5,574,179 A | 11/1996 | Wahl et al. |
| 5,581,005 A | 12/1996 | Perkins |
| 5,597,936 A | 1/1997 | Perkins et al. |
| 5,612,025 A | 3/1997 | Cauwet-Martin et al. |
| 5,612,044 A | 3/1997 | Suares et al. |
| 5,618,523 A | 4/1997 | Zysman et al. |
| 5,633,236 A | 5/1997 | Warren et al. |
| 5,656,585 A | 8/1997 | Grandmaire et al. |
| 5,661,118 A | 8/1997 | Cauwet et al. |
| 5,665,781 A | 9/1997 | Warren et al. |
| 5,665,822 A | 9/1997 | Bitler et al. |
| 5,674,832 A | 10/1997 | Keys |
| 5,679,630 A | 10/1997 | Baeck et al. |
| 5,684,199 A | 11/1997 | Francotte |
| 5,685,422 A | 11/1997 | Kim |
| 5,703,030 A | 12/1997 | Perkins et al. |
| 5,703,034 A | 12/1997 | Offshack et al. |
| 5,705,464 A | 1/1998 | Scheper et al. |
| 5,723,434 A | 3/1998 | Falk et al. |
| 5,726,144 A | 3/1998 | Dewez et al. |
| 5,731,278 A | 3/1998 | Nair et al. |
| 5,740,947 A | 4/1998 | Flaig et al. |
| 5,753,686 A | 5/1998 | Marin et al. |
| 5,756,436 A | 5/1998 | Royce et al. |
| 5,759,990 A | 6/1998 | Wahl et al. |
| 5,767,055 A | 6/1998 | Choy et al. |
| 5,776,443 A | 7/1998 | Vinski et al. |
| 5,776,883 A | 7/1998 | Vasudevan |
| 5,783,302 A | 7/1998 | Bitler et al. |
| 5,783,544 A | 7/1998 | Trinh et al. |
| 5,798,385 A | 8/1998 | Marin |
| 5,804,546 A | 9/1998 | Hall |
| 5,837,661 A | 11/1998 | Evans et al. |
| 5,849,313 A | 12/1998 | Fost et al. |
| 5,877,145 A | 3/1999 | Wahl et al. |
| 5,880,084 A | 3/1999 | Ewbank et al. |
| 5,902,781 A | 5/1999 | Painter |
| 5,914,307 A | 6/1999 | DeNome et al. |
| 5,916,862 A | 6/1999 | Morelli et al. |
| 5,929,022 A | 7/1999 | Velazquez |
| 5,932,203 A | 8/1999 | Coffindaffer et al. |
| 5,935,561 A | 8/1999 | Inman et al. |
| 5,939,373 A | 8/1999 | Haeggberg et al. |
| 5,962,386 A | 10/1999 | Scheper et al. |
| 5,968,286 A | 10/1999 | Crudele et al. |
| 5,968,404 A | 10/1999 | Trinh et al. |
| 5,968,881 A | 10/1999 | Haeggberg et al. |
| 5,990,065 A | 11/1999 | Vinson et al. |
| 6,001,343 A | 12/1999 | Trinh et al. |
| 6,017,871 A | 1/2000 | Baeck et al. |
| 6,020,294 A | 2/2000 | Getty et al. |
| 6,024,943 A | 2/2000 | Ness et al. |
| 6,042,792 A | 3/2000 | Shefer et al. |
| 6,057,404 A | 5/2000 | Utecht et al. |
| 6,069,122 A | 5/2000 | Vinson et al. |
| 6,071,569 A | 6/2000 | Stambaugh |
| 6,106,875 A | 8/2000 | Soper et al. |
| 6,113,935 A | 9/2000 | Rodson et al. |
| 6,133,226 A | 10/2000 | Knowlton et al. |
| 6,143,707 A | 11/2000 | Trinh et al. |

| | | | | | | |
|---|---|---|---|---|---|---|
| 6,146,621 | A | 11/2000 | Trinh et al. | 6,696,395 B1 | 2/2004 | Woo et al. |
| 6,162,423 | A | 12/2000 | Sebag et al. | 6,696,402 B2 | 2/2004 | Gosselink et al. |
| 6,180,594 | B1 | 1/2001 | Fender et al. | 6,699,824 B1 | 3/2004 | Dawson et al. |
| 6,190,678 | B1 | 2/2001 | Hasenoehrl et al. | 6,758,411 B2 | 7/2004 | Conway et al. |
| 6,194,375 | B1 | 2/2001 | Ness et al. | 6,764,986 B1 | 7/2004 | Busch et al. |
| 6,200,554 | B1 | 3/2001 | Yeoh et al. | 6,767,875 B1 | 7/2004 | Snyder et al. |
| 6,213,409 | B1 | 4/2001 | Warren et al. | 6,770,103 B2 | 8/2004 | Patel et al. |
| 6,221,826 | B1 | 4/2001 | Surutzidis et al. | 6,770,715 B2 | 8/2004 | Garrison et al. |
| 6,225,489 | B1 | 5/2001 | Fost et al. | 6,776,308 B1 | 8/2004 | Davis et al. |
| 6,248,315 | B1 | 6/2001 | Young et al. | 6,784,224 B2 | 8/2004 | Nakayama et al. |
| 6,255,367 | B1 | 7/2001 | Bitler et al. | 6,784,248 B2 | 8/2004 | Coca et al. |
| 6,261,483 | B1 | 7/2001 | Frank et al. | 6,784,258 B2 | 8/2004 | Ambrose et al. |
| 6,268,431 | B1 | 7/2001 | Snyder et al. | D495,949 S | 9/2004 | Rymer et al. |
| 6,297,203 | B1 | 10/2001 | Guskey et al. | 6,787,589 B2 | 9/2004 | Weaver et al. |
| 6,297,210 | B1 | 10/2001 | Hsu et al. | 6,790,434 B2 | 9/2004 | Borchert et al. |
| 6,329,057 | B1 | 12/2001 | Dungworth et al. | 6,790,453 B2 | 9/2004 | Porzio et al. |
| 6,335,315 | B1 | 1/2002 | Trinh et al. | 6,790,463 B2 | 9/2004 | Hofmann et al. |
| 6,348,218 | B1 | 2/2002 | Hed et al. | 6,790,819 B2 | 9/2004 | Trinh et al. |
| 6,355,234 | B1 | 3/2002 | Birtwistle et al. | 6,790,919 B2 | 9/2004 | Matyjaszewski et al. |
| 6,379,658 | B1 | 4/2002 | Marano et al. | 6,790,921 B1 | 9/2004 | Rodewald et al. |
| 6,413,548 | B1 | 7/2002 | Hamer et al. | 6,794,346 B2 | 9/2004 | Wick et al. |
| 6,436,383 | B2 | 8/2002 | Murray | 6,794,356 B2 | 9/2004 | Turner et al. |
| 6,451,065 | B2 | 9/2002 | Trinh et al. | 6,794,479 B2 | 9/2004 | Okuhira et al. |
| 6,479,042 | B1 | 11/2002 | Nguyen et al. | 6,797,756 B2 | 9/2004 | Agniel et al. |
| 6,479,043 | B1 | 11/2002 | Tietjen et al. | D545,219 S * | 6/2007 | Troost et al. ................. D9/738 |
| 6,479,059 | B2 | 11/2002 | Montanari et al. | 2001/0008674 A1 | 7/2001 | Igari et al. |
| 6,485,713 | B1 | 11/2002 | Bonda et al. | 2002/0016269 A1 | 2/2002 | Noda et al. |
| 6,491,902 | B2 | 12/2002 | Shefer et al. | 2003/0005522 A1 | 1/2003 | Trinh et al. |
| 6,491,933 | B2 | 12/2002 | Lorenzi et al. | 2003/0013632 A1 | 1/2003 | Santos et al. |
| 6,492,462 | B2 | 12/2002 | Bitler et al. | 2003/0069164 A1 | 4/2003 | Levinson |
| 6,495,058 | B1 | 12/2002 | Frankenbach et al. | 2003/0092600 A1 | 5/2003 | Shepherd, Jr. |
| 6,497,860 | B1 | 12/2002 | Kawato et al. | 2003/0119713 A1 | 6/2003 | Heltovics et al. |
| 6,509,034 | B1 | 1/2003 | Calanchi et al. | 2003/0125222 A1 | 7/2003 | Jahns et al. |
| 6,514,487 | B1 | 2/2003 | Barr | 2003/0158072 A1 | 8/2003 | Goodson et al. |
| 6,514,489 | B1 | 2/2003 | Shacknai et al. | 2003/0168462 A1 | 9/2003 | Kiyota |
| 6,514,504 | B1 | 2/2003 | Yen et al. | 2003/0171234 A1 | 9/2003 | Ajmani et al. |
| 6,514,918 | B1 | 2/2003 | Librizzi | 2003/0171246 A1 | 9/2003 | Boeckh et al. |
| 6,514,923 | B1 | 2/2003 | Cheung et al. | 2003/0180335 A1 | 9/2003 | Ohmori et al. |
| 6,517,588 | B2 | 2/2003 | Hopkinson | 2003/0199412 A1 | 10/2003 | Gupta et al. |
| 6,521,589 | B2 | 2/2003 | Demeyere et al. | 2004/0002434 A1 | 1/2004 | Perkins et al. |
| 6,524,494 | B2 | 2/2003 | Hart et al. | 2004/0060840 A1 | 4/2004 | Williams et al. |
| 6,528,013 | B1 | 3/2003 | Trinh et al. | 2004/0063600 A1 | 4/2004 | Williams et al. |
| 6,528,046 | B1 | 3/2003 | Schmenger et al. | 2004/0071742 A1 | 4/2004 | Popplewell et al. |
| 6,531,113 | B1 | 3/2003 | Mougin et al. | 2004/0071746 A1 | 4/2004 | Popplewell et al. |
| 6,531,160 | B2 | 3/2003 | Biatry et al. | 2004/0072719 A1 | 4/2004 | Bennett et al. |
| 6,531,437 | B1 | 3/2003 | Ryan et al. | 2004/0072720 A1 | 4/2004 | Brain et al. |
| 6,540,989 | B2 | 4/2003 | Janchitraponvej | 2004/0138093 A1 | 7/2004 | Brain et al. |
| 6,544,535 | B2 | 4/2003 | Sakurai et al. | 2004/0142828 A1 | 7/2004 | Popplewell et al. |
| 6,545,084 | B2 | 4/2003 | Brown et al. | | | |
| 6,551,604 | B1 | 4/2003 | Beck et al. | | FOREIGN PATENT DOCUMENTS | |
| 6,551,970 | B2 | 4/2003 | Decoster et al. | EP | 0 327 927 | 1/1989 |
| 6,555,098 | B1 | 4/2003 | Murphy et al. | EP | 0 376 385 | 12/1989 |
| 6,569,826 | B1 | 5/2003 | Chiaradonna et al. | EP | 0 437 098 | 7/1991 |
| 6,592,813 | B1 | 7/2003 | Fox et al. | EP | 0 733 097 | 9/1996 |
| 6,592,857 | B2 | 7/2003 | Lawson et al. | EP | 0 965 326 | 12/1999 |
| 6,620,437 | B2 | 9/2003 | Ewbank et al. | EP | 1 061 124 | 12/2000 |
| 6,620,777 | B2 | 9/2003 | Heibel et al. | GB | 1180427 | 2/1970 |
| 6,645,479 | B1 | 11/2003 | Shefer et al. | GB | 2 006 709 | 5/1979 |
| 6,649,154 | B1 | 11/2003 | Yoshida et al. | GB | 1 561 389 | 2/1980 |
| 6,649,173 | B1 | 11/2003 | Arnaud et al. | GB | 2 062 570 | 5/2001 |
| 6,649,175 | B1 | 11/2003 | Haslwanter et al. | WO | 95/18096 | 7/1995 |
| 6,649,178 | B2 | 11/2003 | Mohammadi et al. | WO | 97/12022 | 4/1997 |
| 6,649,578 | B1 | 11/2003 | O'Lenick, Jr. | WO | 97/12027 | 4/1997 |
| 6,649,579 | B2 | 11/2003 | Denton | WO | 98/33880 | 8/1998 |
| 6,652,766 | B1 | 11/2003 | Frankenbach et al. | WO | 01/00765 | 1/2001 |
| 6,653,277 | B1 | 11/2003 | Golz-Berner et al. | WO | 01/05358 | 1/2001 |
| D484,038 | S | 12/2003 | Santiago et al. | WO | 01/40430 | 6/2001 |
| 6,656,923 | B1 | 12/2003 | Trinh et al. | WO | 01/49817 | 7/2001 |
| 6,664,223 | B2 | 12/2003 | Zappone et al. | WO | 01/62376 | 8/2001 |
| 6,667,287 | B2 | 12/2003 | Aszman et al. | WO | 02/34225 | 5/2002 |
| 6,693,065 | B2 | 2/2004 | Gentilhomme et al. | WO | 02/34226 | 5/2002 |
| 6,693,068 | B1 | 2/2004 | Ryan et al. | WO | 02/074430 | 9/2002 |
| 6,696,053 | B1 | 2/2004 | Ma et al. | | | |

| | | |
|---|---|---|
| WO | 02/085420 | 10/2002 |
| WO | 03/002699 | 1/2003 |
| WO | 03/074580 | 9/2003 |

OTHER PUBLICATIONS

Barton, CRC Handbook of Polymer-Liquid Interaction Parameters and Solubility Parameters, CRC Press, Part I, Introduction.

Gmehling, et al, Vapor-Liquid Equilibria by UNIFAC Group Contribution.Revision and Extension.2, Ind.Eng.Chem.Process Des.Dev., 1982, 21, pp. 118-127.

U.S. Appl. No. 10/706,888, filed Nov. 13, 2003, Parekh et al (IFF-71).

U.S. Appl. No. 10/718,239, filed Nov. 20, 2003, Parekh et al (IFF-70).

U.S. Appl. No. 10/718,240, filed Nov. 20, 2003, Popplewell et al (IFF-56).

U.S. Appl. No. 10/718,368, filed Nov. 20, 2003, Popplewell et al (IFF-43).

U.S. Appl. No. 10/720,572, filed Nov. 24, 2003, Brain et al (IFF-40-2).

U.S. Appl. No. 10/720,574, filed Nov. 24, 2003, Popplewell et al (IFF-36-2).

* cited by examiner

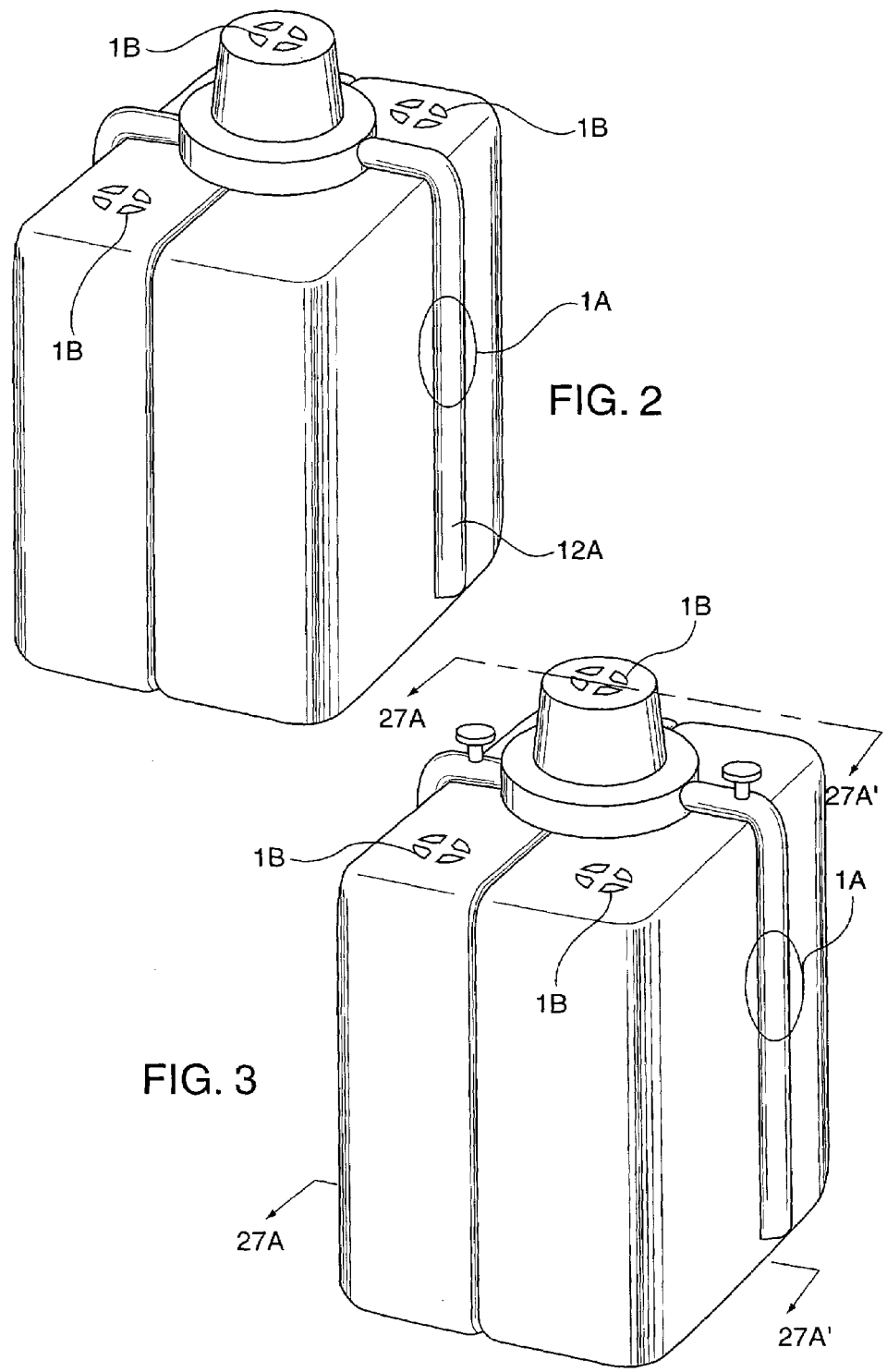

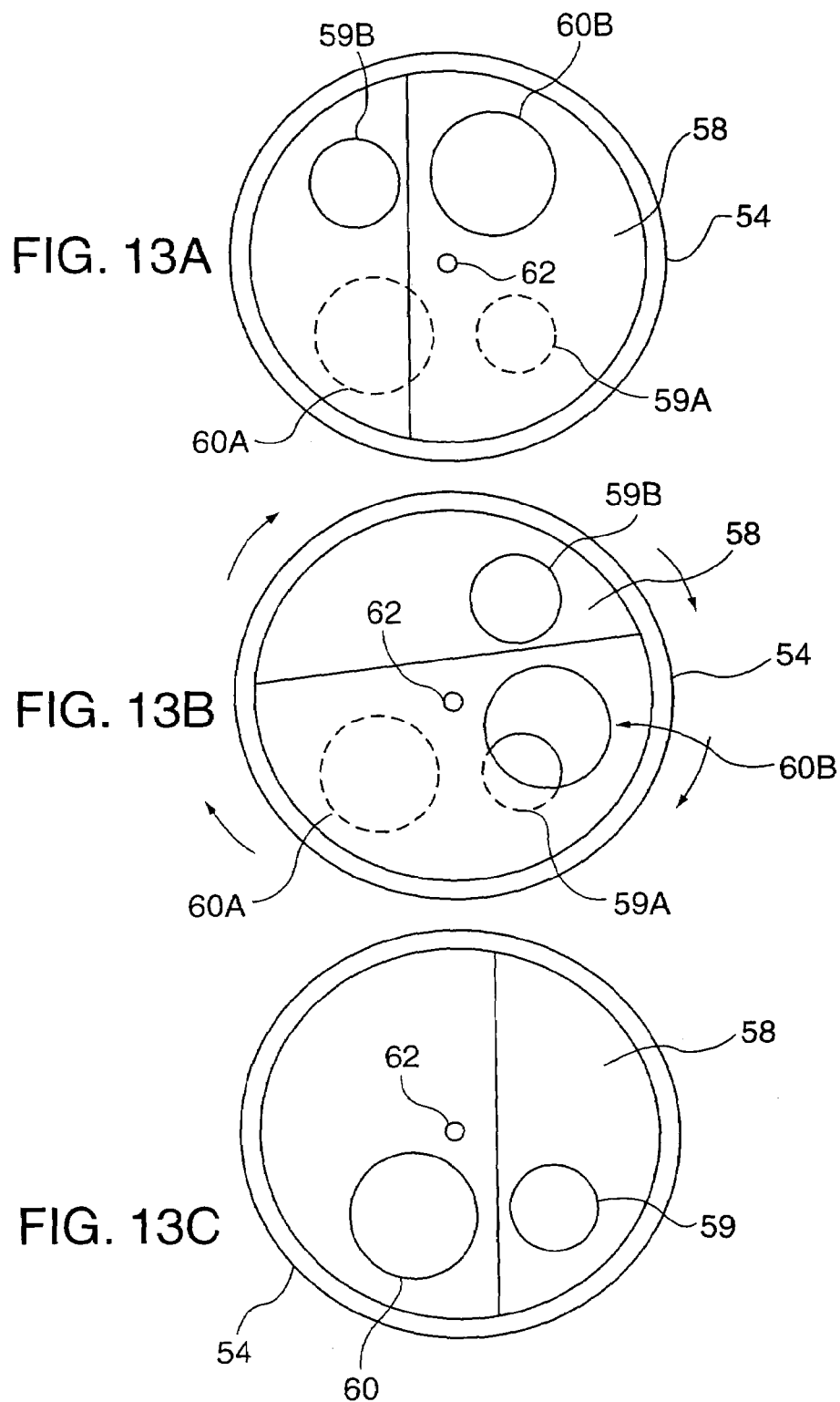

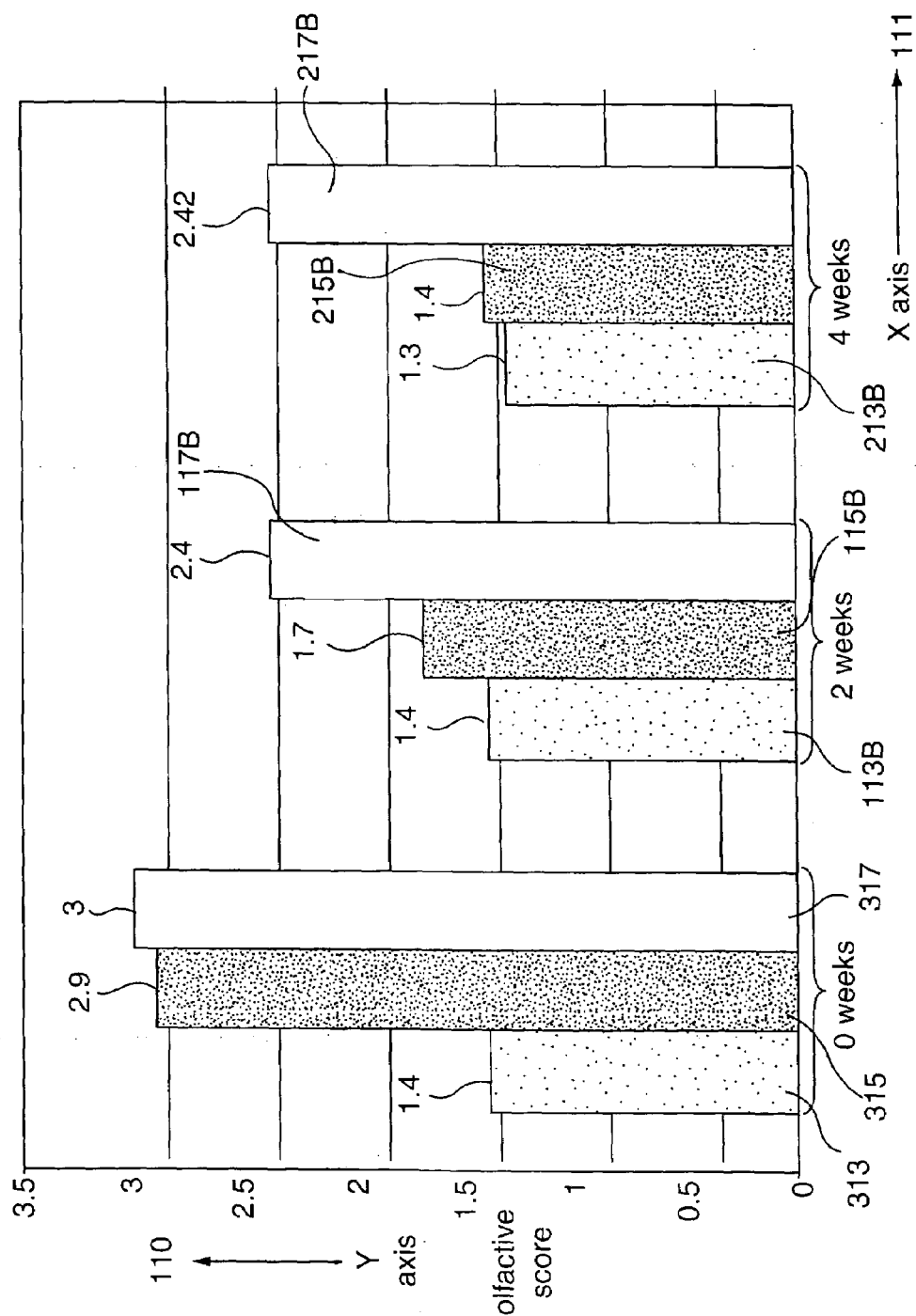

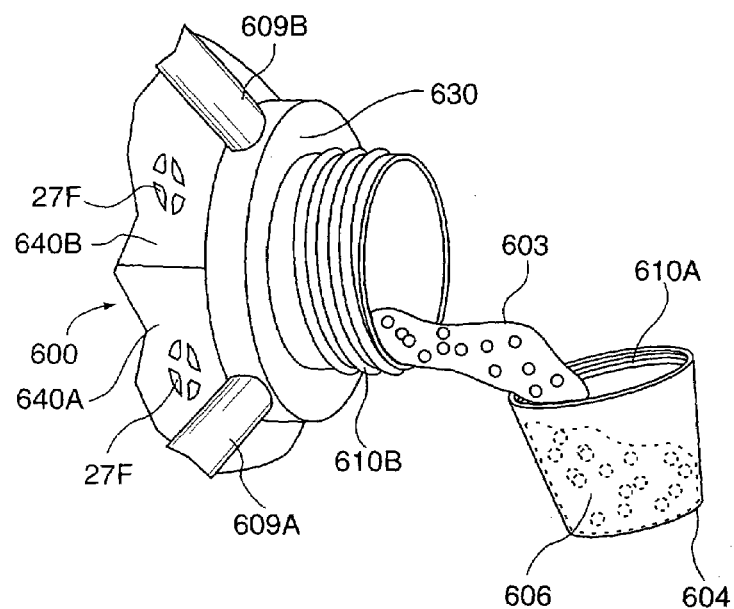
FIG. 27C
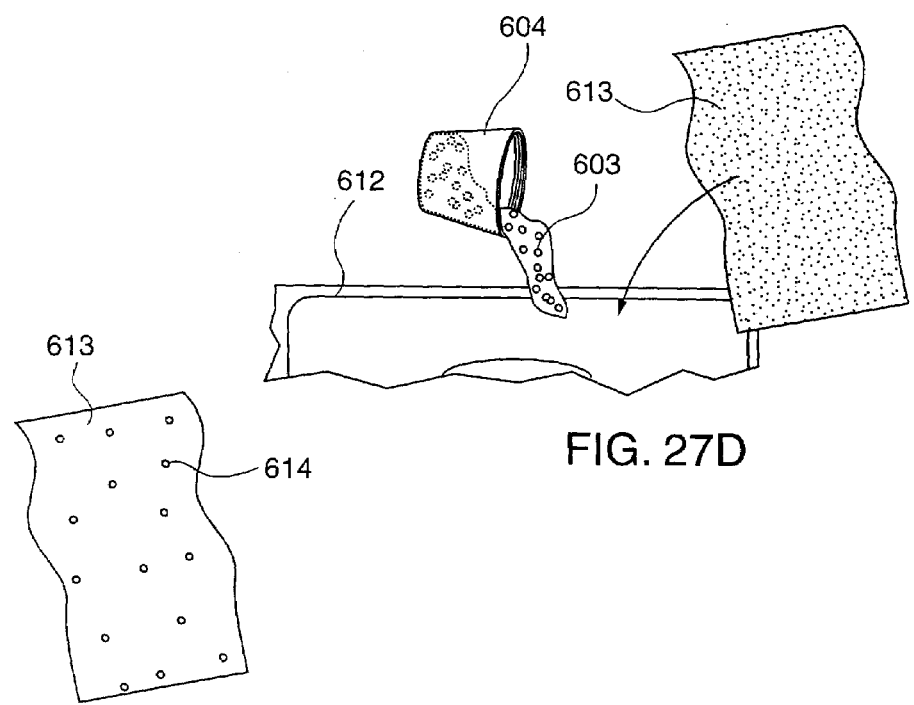
FIG. 27D
FIG. 27E

US 7,594,594 B2

MULTI-COMPARTMENT STORAGE AND DELIVERY CONTAINERS AND DELIVERY SYSTEM FOR MICROENCAPSULATED FRAGRANCES

FIELD OF THE INVENTION

Multi-compartment storage and delivery containers, use of storing and dispensing reactive fluidic compositions, and utilization of such containers for pre-storing in separate compartments and subsequently mixing (i) suspensions of microencapsulated fragrance(s) and/or benefit agent(s) with (ii) fluidic surface or volume treatment agent compositions and then delivering the resulting mixture(s) to at least one solid or semi-solid surface and/or gaseous-phase or liquid-phase defined volumes.

BACKGROUND OF THE INVENTION

Situations exist where it is desirable to provide to a solid or semi-solid surface or to a liquid phase or vapor phase three-dimensional volume a mixture of two, three or four compositions, one or more components of which chemically react and/or physically interact with another of the components of another of the compositions and whose reaction and/or interaction is desired to occur on the aforementioned solid or semi-solid surface or in the aforementioned liquid phase or vapor phase three-dimensional volume but not in the container wherein the aforementioned two, three or four compositions are stored. Examples of this type of system include:

(a) cleaning systems in which (i) an alkaline material and (ii) an acid material and/or (i) an oxidative material and (ii) a reductive material are brought together on a solid or semi-solid surface and/or in a liquid-phase volume to provide, for example, an effervescing action, a cleansing action, and a dissolution of soil on a solid or semi-solid surface and/or in a liquid phase volume, e.g. utilizing the dual container article and drain-cleaning compositions, LIQUID-PLUMR®, The Clorox Company or the dual container article and drain-cleaning compositions DRANO® The Drackett Company; or the dual container article and carpet care compositions stored OXY KIC® BISSEL Homecare;

(b) oral care systems in which (i) an oxidative material and (ii) a reductive material are brought together in the oral cavity to provide a cleansing action therein, e.g. utilizing the container article and compositions, MENTADENT® Church & Dwight Company;

(c) liquid personal care products in which (i) a body wash, a lotion, a cream, a shampoo, a hair conditioner, a hair color former and/or a hair color modifier, e.g. a hair bleach and (ii) a fluidic microencapsulated fragrance and/or benefit composition, such as an aqueous slurry of microencapsulated fragrance and/or benefit agent are admixed;

(d) liquid fabric care products in which (i) a liquid detergent, including. WISK® Cheseborough Ponds Inc; and/or a liquid fabric softener, such as SUAVITEL® Colgate-Palmolive Company. and (ii) a fluidic microencapsulated fragrance and/or benefit agent composition, e.g. an aqueous slurry of microencapsulated fragrance and/or benefit agent are brought together on a solid or semi-solid surface or in a temporarily-storable admixture to provide an appropriately-treated solid or semi-solid surface e.g. a fabric surface or a cookware surface;

(e) color forming systems in which (i) a first dye precursor and (ii) a second dye precursor are brought together and the resulting dye is appropriately applied to a surface or subsequently admixed with other appropriate components; and (f) adhesion systems and/or plumbing systems in which (i) a pre-polymer such as an epoxy resin pre-polymer, e.g. the reaction product of epichlorohydrin and bis-phenol-A or a cross-linkable vinyl polymer such as a low molecular weight polyacrylic acid-polyacrylamide co-polymer, (ii) optionally a cross-linking agent such as a melamine-formaldehyde cross-linker and (iii) a curing catalyst are brought together at the junction of two solid surfaces of two articles in order to permanently adhere the article surfaces, one to the other, for example, using the package instructions for the epoxy resin pre-polymer—curing agent , J-B WELD® Mary L. Bonham and VersaChem® 4 Minute Epoxy Steel Quick Set Type 44™, ITW Performance Polymers Consumer Division.

The aforementioned reactive and/or interactive compositions cannot be stored in the same three-space or three-dimensional volume for an extended period of time, such as more than 1 minute or, constituting an unstable system, they would react and/or interact while in storage, whereupon their solid or semi-solid surface or liquid phase three-dimensional volume treatment capabilities would be totally or substantially nullified.

The prior art recognizes the aforementioned reaction and/or interactive composition storage problems and discloses a number of dual container article systems for storing such reactive compositions and/or interactive compositions, and delivering the compositions to solid or semi-solid surfaces or to liquid-phase or gaseous-phase volumes, for example in U.S. Pat. Nos. 3,760,986, 4,585,150, and 6,776,308

The prior art, however, does not provide reactive and/or interactive composition pre-storage and delivery systems where, immediately prior to use, the rate of mixing of the reactive and/or interactive compositions and time of mixture storage prior to delivery to the surface-to-be-treated or to the liquid phase or gaseous phase volume-to-be treated are readily controllable. Further, although such problems as the interaction of personal care, surface cleaning and fabric care bases with microencapsulated fragrance and/or benefit agents, such as air freshener, malodour counteractant and/or insect repellent, slurry suspensions appear to be recognized in such disclosures as published U.S. patent application Ser. No. 2004/0071742 which discloses:

". . . if stability of the capsule and coating system is compromised by inclusion in the product base, product forms which separate the bulk of the base from the fragrance composition may be employed . . ."

no specificity as to the 'product forms' mentioned is disclosed or suggested in the prior art.

In addition, the prior art does not disclose or suggest a versatile multiple, such as 2-4 separated, compartment article initially containing, in each compartment, a fluidic composition which contains at least one component which will chemically react and/or physically interact over a relatively short period of time with at least one component of another fluidic composition located in another of the compartments on mixing therewith that can, when in either (i) a stationery upright position or (ii) when being held in a non-vertical position is capable of providing in an expeditiously controlled manner a temporarily storable, deliverable and promptly usable mixture of the reactive and/or interactive component-containing pre-stored compositions.

SUMMARY OF THE INVENTION

It is, accordingly, an object of our invention to provide reactive and/or interactive composition pre-storage and delivery systems where, immediately prior to use, the rate of mixing of the reactive and/or interactive compositions and time of mixture storage prior to delivery to the surface-to-be-treated or to the liquid phase or gaseous phase three-dimensional volume-to-be treated are readily controllable.

Another object of our invention is to provide a 'product form' for enabling storage and delivery of personal care, surface cleaning and fabric care "bases" with microencapsulated fragrance and/or benefit agent, such as an insect repellent, an air freshener and/or a malodour counteractant slurry suspensions.

Another object of our invention is to provide a versatile multiple (2-4) separated compartment article, initially containing, separately, in each compartment, a fluidic composition which contains at least one component which will chemically react and/or physically interact over a relatively short period of time with at least one component of another fluidic composition located in another of the compartments on mixing therewith, that can, when in either (i) a stationery upright position or (ii)when being held in a non-vertical position is capable of providing in an expeditiously controlled manner a temporarily storable, deliverable and promptly usable mixture of the reactive and/or interactive component-containing pre-stored compositions.

One embodiment of the invention is drawn to (i) a method for mixing pre-storable, individually stable compositions and then delivering to a solid or semi-solid surface or to a liquid phase or gaseous phase defined volume to be treated an unstable liquid surface or volume treatment system containing (a) a microencapsulated fragrance and/or benefit agent slurry suspension which is stable when individually pre-stored and (b) one or more liquid surface or volume treatment compositions each of which is stable when individually pre-stored and (ii) an article for pre-storing from two to four fluidic compositions each of which composition is stable when individually pre-stored but unstable on mixing, enabling the mixing of two or more of the fluidic pre-stored, individually stable compositions, and effecting delivery of the resulting unstable mixture to a solid or semi-solid surface or liquid phase or gaseous phase volume.

The method for mixing ((i), pre-storable, individually stable compositions of our invention is applicable to a multitude of multi-compartment containers including but is not limited to the articles described in the attached specification The article of our invention is applicable to a multitude of methods for mixing pre-storable individually stable compositions which, upon admixture thereof evolve into unstable mixtures, including, but not limited to the method for mixing of our invention.

The term unstable used herein is herein intended to refer to a mixture of two or more compositions, at least one component of each of which is chemically reactive or physically interactive with at least one component of another of the compositions. For example, one stably pre-storable composition contains an oxidizing agent and a second stably pre-storable composition contains a reducing agent, but when the compositions are admixed, the resulting mixture is unstable due to the immediate reactivity of the oxidizing agent with the reducing agent.

The term benefit agent is herein intended to mean a substance that when applied to a solid or semi-solid surface or to a liquid or gaseous defined volume will provide a benefit other than a fragrance, for example, air-freshening, insect repellency, malodour counteractancy, anti-microorganism properties, e.g. anti-bacterial or anti-fungal properties and/or hair color modification.

In particular, our invention provides:
 (a) reactive and/or interactive composition pre-storage and delivery systems where, immediately prior to use, the rate of mixing of the reactive and/or interactive compositions and time of mixture storage prior to delivery to the surface-to-be-treated or to the liquid phase or gaseous phase three-dimensional volume-to-be treated are readily controllable;
 (b) a 'product form' for enabling storage and delivery of personal care, surface cleaning and fabric care "bases" with microencapsulated fragrance and/or benefit agent, slurry suspensions; and
 (c) a versatile multi (2-4) separated compartment article (initially containing, separately, in each compartment, a fluidic composition which contains at least one component which will chemically react and/or physically interact over a relatively short period of time with at least one component of another fluidic composition located in another of the compartments on mixing therewith) that can, when in either (i) a stationery upright position or (ii) when being held in a non-vertical position is capable of providing in an expeditiously controlled manner a temporarily storable, deliverable and promptly usable mixture of the reactive and/or interactive component-containing pre-stored compositions.

More particularly, our invention is directed to a multiple (2-4)-compartment fluidic individually stable, pre-storable composition storage and unstable mixture-forming and delivery container having separate compartments each communicating with a single mixing zone, where reactive and/or interactive fluidic compositions, each of which is individually stable and pre-storable, are mixed, via an externally-located fluidic composition multiple delivery tube system juxtaposed with the outer surfaces of the compartment walls; and (2) a system designed for the utilization of such a multiple (2-4)-compartment stable composition storage, unstable mixture-forming and delivery container for pre-storing in separate compartments and subsequently mixing (i) individually stable, pre-storable suspensions of microencapsulated fragrance(s) and/or benefit agent(s) with (ii) one or more individually stable, pre-storable fluidic surface or volume treatment compositions such as a cleaning agent composition, a personal care composition, an aqueous liquid detergent composition and/or a fabric softening composition and then delivering the resulting unstable mixture(s) to at least one solid or semi-solid surface or a liquid-phase or gaseous-phase defined volume. The system includes (a) a shelf-stable pre-mix comprising two or more components wherein at least one component is an aqueous suspension of microencapsulated fragrance(s) and/or benefit agent(s) and a second component is a fluidic surface or volume treatment composition such as a liquid detergent composition or liquid fabric softener composition; wherein each of the fluidic compositions is stored separately and, as which are stable, but the fluidic compositions are combinable and thus in an unstable state, and wherein are included all ingredients necessary to be applied to a solid or semi-solid surface or a liquid or gaseous defined volume causing the benefits of said fluidic surface or volume treatment composition(s) and said fragrance and/or benefit agent to be imparted to said solid or semi-solid surface or gaseous-phase or liquid-phase defined volume; (b) a method for combining the components of the premix and (c) a specific article for effecting the admixture and subsequent delivery of the pre-mix components.

More specifically, our invention is directed to the following:

(A) an article for effecting the dispensing of a mixture of from two to four fluidic compositions each of which fluidic composition has a chemical constituency different from any other of the fluidic compositions and each of which fluidic composition is chemically and/or physically reactive with each of the other fluidic compositions when in intimate contact therewith over a finite period of time, such as 1-30 minutes. Such article comprises:

(a) from two to four upright hollow storage members, such as in the shape of cylinders, elliptical cylinders and/or parallelepipeds, vertically juxtaposed to one-another, each of which storage member has an internal storage 3-space and each of which storage member has a substantially horizontally-disposed substantially planar storage member base having a storage member base circumferential edge. Extending upwardly from the entirety of the storage member base circumferential edge, an elastically deformable vertically-disposed liquid-impermeable storage member sidewall, preferably fabricated from an elastomer, having an outer side and an inner side, terminating at its upper end at the entirety of the circumferential edge of a substantially horizontally-disposed planar storage member lid. Each storage member sidewall has a fluidic composition-exiting orifice there through proximate, i.e. immediately above the location of the storage member base. Each orifice has an internal diameter equal to the external diameter of a storage compartment-mixing chamber communication tube fitted thereto, described, infra. Each of the internal storage 3-spaces (also, herein termed 'three-dimensional volumes') is thus bounded by (i) a planar storage member base, (ii) at least one storage member sidewall and (iii) a planar storage member lid and is fully enclosed and liquid-tight except for the exiting orifice connected to an external fluidic composition communication tube;

(b) atop a section of each of the storage member lids, and covering a substantial surface area thereof, is a single upright hollow mixing chamber having a horizontally-disposed planar mixing chamber base juxtaposed in its entirety with a section of each of said planar storage member lids and having a mixing chamber circumferential edge. Extending upwardly from the entirety of the mixing chamber base circumferential edge is a substantially vertically-disposed continuous liquid-impermeable mixing chamber sidewall terminating at its upper end at a mixing chamber upper horizontally-disposed planar lid. The mixing chamber lid has an orifice there through (preferably circular or elliptical in shape) which orifice has a mixing chamber upper inner orifice rim. The mixing chamber sidewall has from two to four spaced mixing chamber fluidic composition entry orifices there through with the number of the mixing chamber fluidic composition entry orifices being equal to the number of hollow upright storage members. Each mixing chamber entry orifice is in communication with each storage member exiting orifice via a communication tube as more fully described, supra. Also, each mixing chamber entry orifice has an inside diameter equal to that of the inside diameter of a corresponding vertically-positioned fluidic composition communication tube fitted thereto, as more fully described, infra;

(c) abutting the entirety of the mixing chamber upper orifice rim in a liquid-tight manner, a hollow substantially cylindrical or frusto-conical cap member having a substantially planar horizontally-disposed upper cap base having an upper cap base circumferential edge. Extending downwardly from the upper cap base circumferential edge, a substantially continuous substantially vertically-disposed cap sidewall terminating at and abutting the upper inner orifice rim of the mixing chamber; and (d) from two to four vertically disposed storage member-mixing chamber fluidic composition elastically deformable communication tubes each of which tube extends in a substantially vertical direction from and connects the fluidic composition exiting orifice of a storage member to one fluidic composition entry orifice of the mixing chamber adjacent to and abutting the outer side of the storage member sidewall.

Accordingly, when external manual pressure is exerted on a given storage member sidewall when the storage member contains a fluidic composition, the fluidic composition contained therein will flow from the storage member 3-space through the fluid communication tube connected to the storage member sidewall exiting orifice, past the corresponding mixing chamber fluidic composition entry orifice into the mixing chamber;

(B) A process for dispensing from the immediately-aforementioned article (A), above an unstable mixture of at least two fluidic compositions, termed "$S_1$", "$S_2$" "$S_3$" and "$S_4$", or, more generally, "$S_1+\ldots+S_n$" wherein n is an integer of from 2 to 4, which react and/or interact with one-another over a given period of time. Such process comprises the steps of:

(a) providing a dis-assembled article whereby the cap member is removed from the mixing chamber upper inner orifice rim in order to facilitate fluidic composition entry into each 3-space of each of said storage members;

(b) at least partially filling each storage member 3-space with a different individually stable, pre-storable fluidic composition;

(c) completing assembly of the article whereby the cap member is detachably attached to the mixing chamber upper inner orifice rim;

(d) Applying manual pressure to the flexible (or 'elastically deformable') sidewall of each of the storage members containing an individually stable, pre-storable fluidic composition, thereby effecting fluid flow from at least two of said storage member 3-spaces into the mixing chamber thereby forming in said mixing chamber an unstable mixture of $S_1+\ldots+S_n$;

(e) Removing the cap member from the article;

(f) transporting the resulting unstable mixture of $S_1+\ldots+S_n$ into the inner void of the cap member; and (g) dispensing the unstable mixture of $S_1+\ldots+S_n$ from the cap member;

(C) a method for simultaneously (i) substantively imparting a fragrance and/or benefit agent to a solid or semi-solid surface and/or liquid-phase or gaseous-phase defined volume and (ii) treating said solid or semi-solid surface and/or liquid-phase or gaseous-phase defined volume with a fluidic surface or volume treatment agent composition. The method comprises the steps of:

(a) transporting a measured quantity of a pre-stored stable aqueous suspension of microencapsulated fragrance(s)

and/or benefit agent(s) from a first storage location to a given mixing location proximate the first storage location;

(b) simultaneously transporting a measured quantity of a pre-stored stable fluidic surface or volume treatment agent composition from a second storage location juxtaposed with (or abutting) the first storage location to the mixing location, with the mixing location being proximate each of the first storage location and said second storage location;

(c) effecting the mixing of the measured quantity of suspension of microencapsulated fragrance(s) and/or benefit agent(s) and the measured quantity of fluidic surface or volume treatment agent composition at said mixing location whereby an intimate unstable admixture of suspension of microencapsulated fragrance(s) and/or benefit agent(s) and fluidic surface or volume treatment agent composition is formed; and (d) transporting the intimate unstable admixture of suspension and fluidic surface treatment agent composition to the solid or semi-solid surface or to the gaseous-phase or liquid-phase defined volume.

With respect to this method, is to be herein emphasized that the suspension of microencapsulated fragrance(s) and/or benefit agent(s) and the fluidic surface or volume treatment composition are initially contained in separate compartments in a dual compartment article for storage and delivery which prevents contact between the fluidic surface or volume treatment composition and the aqueous suspension of microencapsulated fragrance(s) and/or benefit agent(s) prior to the formation of the intimate unstable admixture thereof at the mixing location. Such article includes (i) first means for dispensing controlled quantities of the suspension of microencapsulated fragrance(s) and/or benefit agent(s) and the fluidic surface or volume treatment composition from each of the dual compartments into the mixing means whereby the intimate unstable admixture is formed and (ii) second means for dispensing the resulting intimate unstable admixture to the exterior of the dual compartment article and onto the solid or semi-solid surface or into the gaseous-phase or liquid-phase defined volume to be treated;

(D) A laundry article for providing fabric care benefits to fabrics. The laundry article comprises:

(a) a container having a three-dimensional mixing zone, which mixing zone has entry and exit ports. Adjacent the mixing zone are at least two separate compartments each of which has an orifice communicating with the entry ports of the mixing zone;

(b) at least one individually stable, pre-storable liquid fabric benefaction composition contained in at least one of the compartments with the liquid fabric benefaction composition containing at least one fabric benefaction agent;

(c) at least one individually stable, pre-storable aqueous suspension of microencapsulated fragrance(s) and/or benefit agent(s) contained in one or more compartments isolatably separate from the compartment(s) containing the fabric cleaning composition(s);

(d) means for causing at least one of the aqueous suspensions to be admixed with at least one of the fabric benefaction compositions in the mixing zone whereby an unstable suspension-cleaning composition mixture is formed; and (e) means for dispensing said suspension-cleaning composition mixture to the exterior of said laundry article substantially immediately subsequent to the formation of said suspension-cleaning composition mixture; and (E) A shelf-stable pre-mix. The pre-mix comprises two or more components wherein at least one component is an individually stable, pre-storable aqueous suspension of microencapsulated fragrance(s) and/or benefit agent(s) and a second component is an individually stable, pre-storable liquid detergent composition and/or an individually stable pre-storable liquid fabric softener composition. The components are stored separately but are combinable to form an unstable mixture, and include all ingredients necessary to be applied to a solid or semi-solid surface or into a gaseous-phase or liquid-phase defined volume causing the benefits of the liquid detergent composition and/or liquid fabric softener composition and the fragrance and/or benefit agent to be imparted to the solid or semi-solid surface or into the liquid-phase or gaseous-phase defined volume, notwithstanding the instability of the resulting combination of (i) the aqueous suspension and (ii) the liquid detergent composition or the liquid fabric softener composition.

BRIEF DESCRIPTION OF THE DRAWINGS

FIG. 1B' is a detailed bottom view of the air vent of FIG. 1B.

FIG. 2 is a front perspective view of a second embodiment of the multi-compartment storage and delivery system of our invention, a dual compartment storage and delivery container with the parallel fluidic composition communication tubes 12A and 12B abutting opposite external sides of the container.

FIGS. 3 and 4A are each front perspective views of the storage and delivery container of FIG. 2 wherein each of the parallel fluidic composition communication tubes is equipped with a fluidic composition flow rate control valve.

FIGS. 13A, 13B and 13C each shows a top view of the mixing chamber of the dual-compartment storage and delivery container of FIG. 12 having compound mixing chamber lid-containing orifices having adjustable dimensions with FIG. 13A showing the compound mixing chamber lid in a closed position; FIG. 13B showing the compound mixing chamber lid in a 'partially-opened' position; and FIG. 13C showing the compound mixing chamber lid in a fully open position.

FIGS. 15-17 are a set of bar graphs of perceived sensory intensity for a microencapsulated fragrance.

$$(v-100)\left(\frac{T}{273}\right) = 47.27e^{-0.14\theta} - 1.62$$

with a standard error of estimate=2.89.

Figure 25:
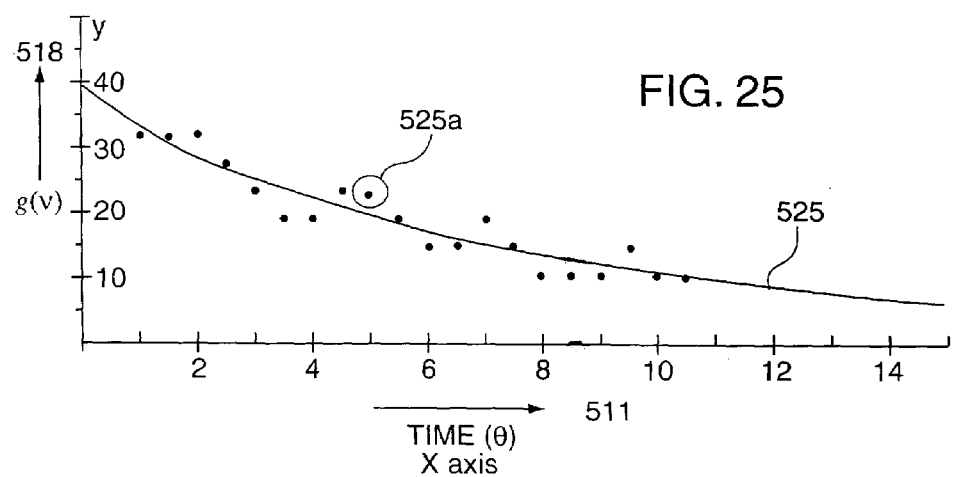

FIG. 25 is a graph of the viscosity function (measured along the "Y" axis for the microencapsulated fragrance of Example B, below, in a capsule slurry suspension vs. storage time measured along the "X" axis.

Figure 26:
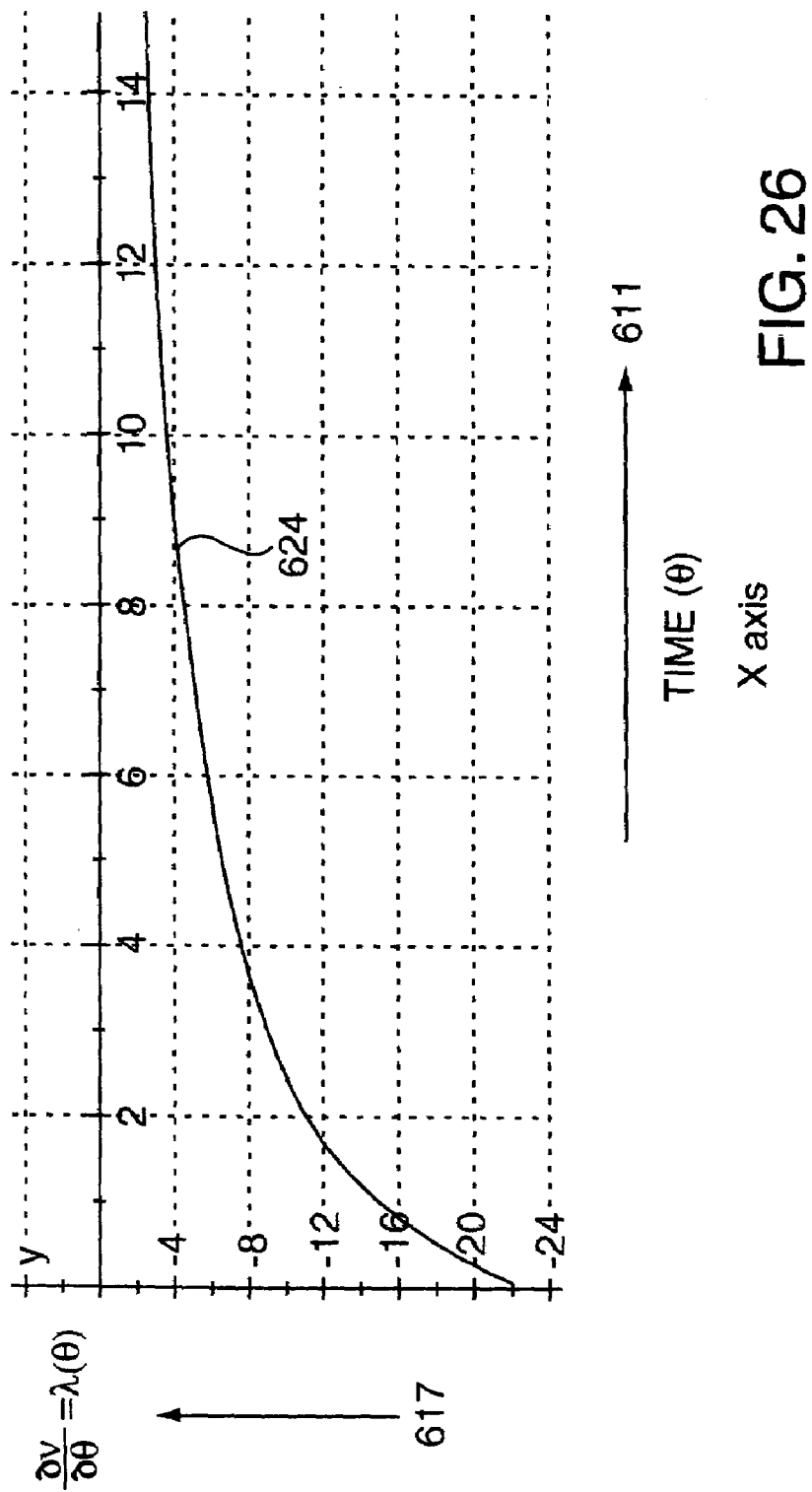

FIG. 26 is a graph of the rate of change of viscosity with respect to time, as a function of time in minutes $$\left(\frac{\partial v}{\partial \theta} = \lambda(\theta)\right)$$

for the microencapsulated fragrance of Example B, below, in a capsule slurry in liquid detergent using the data of FIGS. 24 and 25.

Figure 27A:
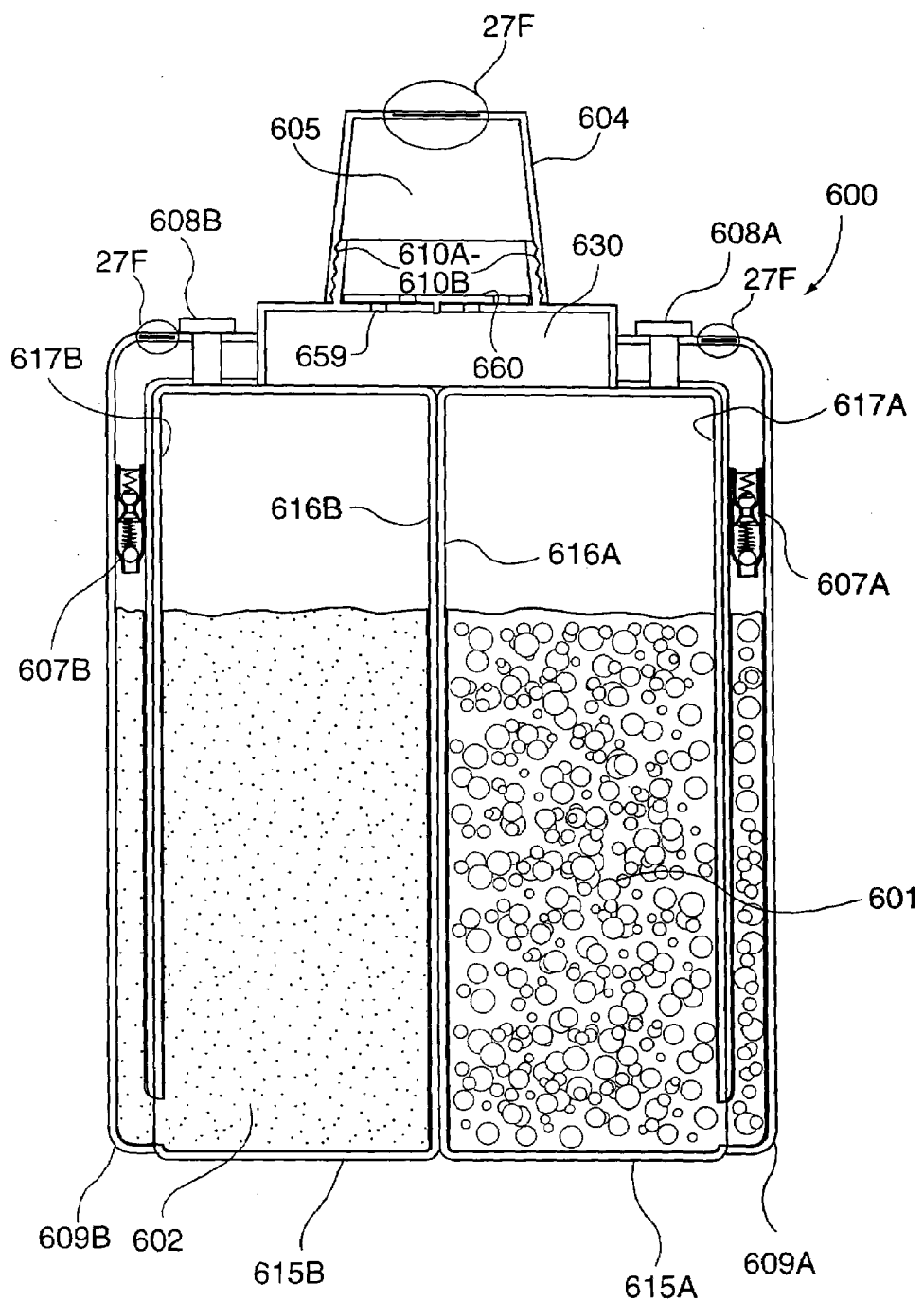

FIG. 27A is a cut-away side elevation view of the storage and delivery container of FIG. 3 taken along lines 27A-27A' prior to flow of the compartment-containing fluidic compositions.

Figure 27B:
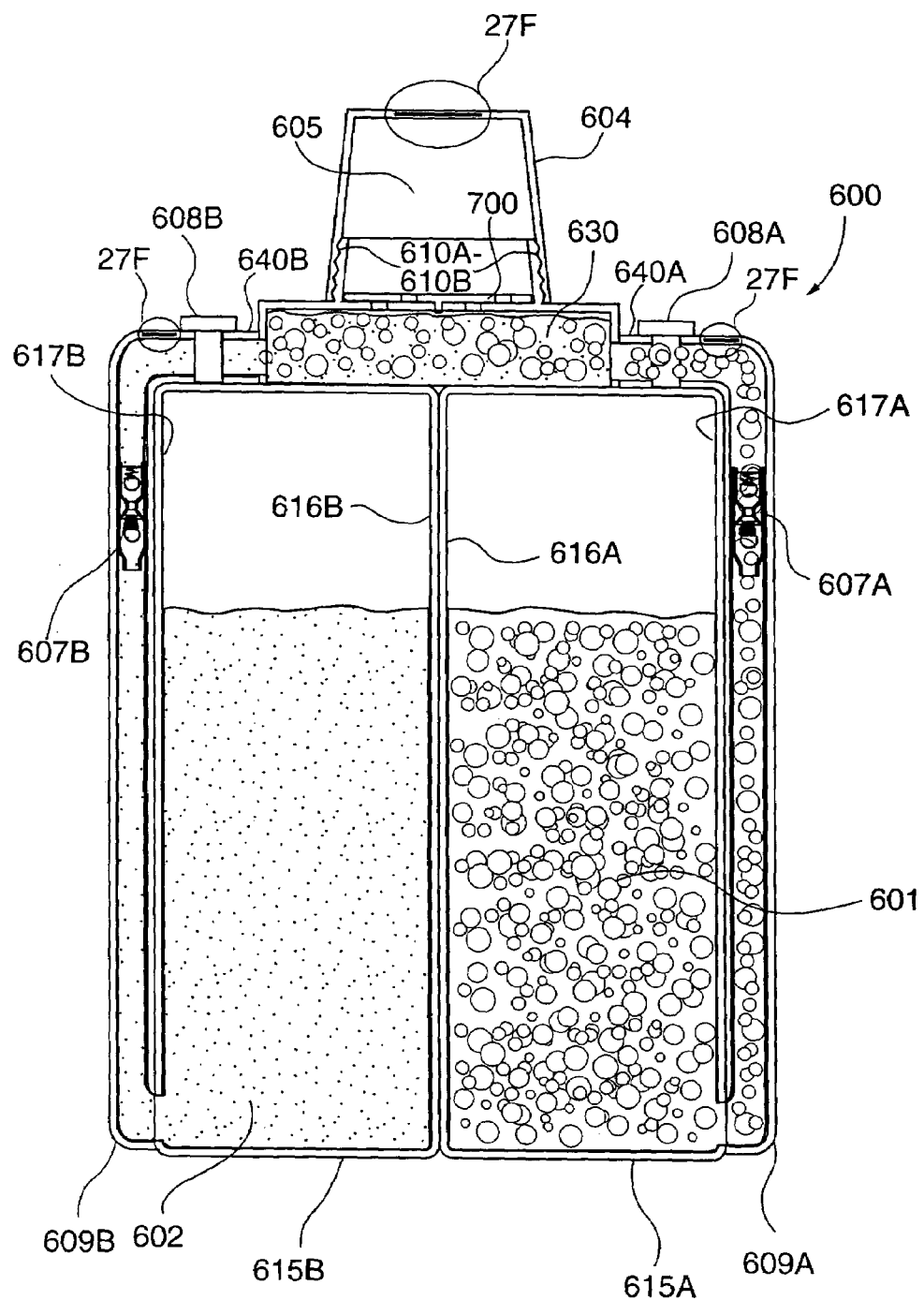

FIG. 27B is a cut-away side elevation view of the storage and delivery container of FIG. 3 taken along lines 27A-27A' during the flow of the compartment-containing fluidic compositions into the mixing chamber.

FIG. 27C is a schematic perspective diagram showing transfer of the mixture from the mixing chamber to the inner void of the cap member.

FIG. 27D is a schematic perspective diagram showing placement of (i) the mixture from the inner void of the cap member of FIG. 3 to a surface treatment apparatus and (ii) a fabric section, the surfaces of which are to be treated, into the same surface treatment apparatus.

FIG. 27E is a schematic diagram of the treated fabric shown in FIG. 27D having microencapsulated fragrances adhered thereto.

Figure 1:
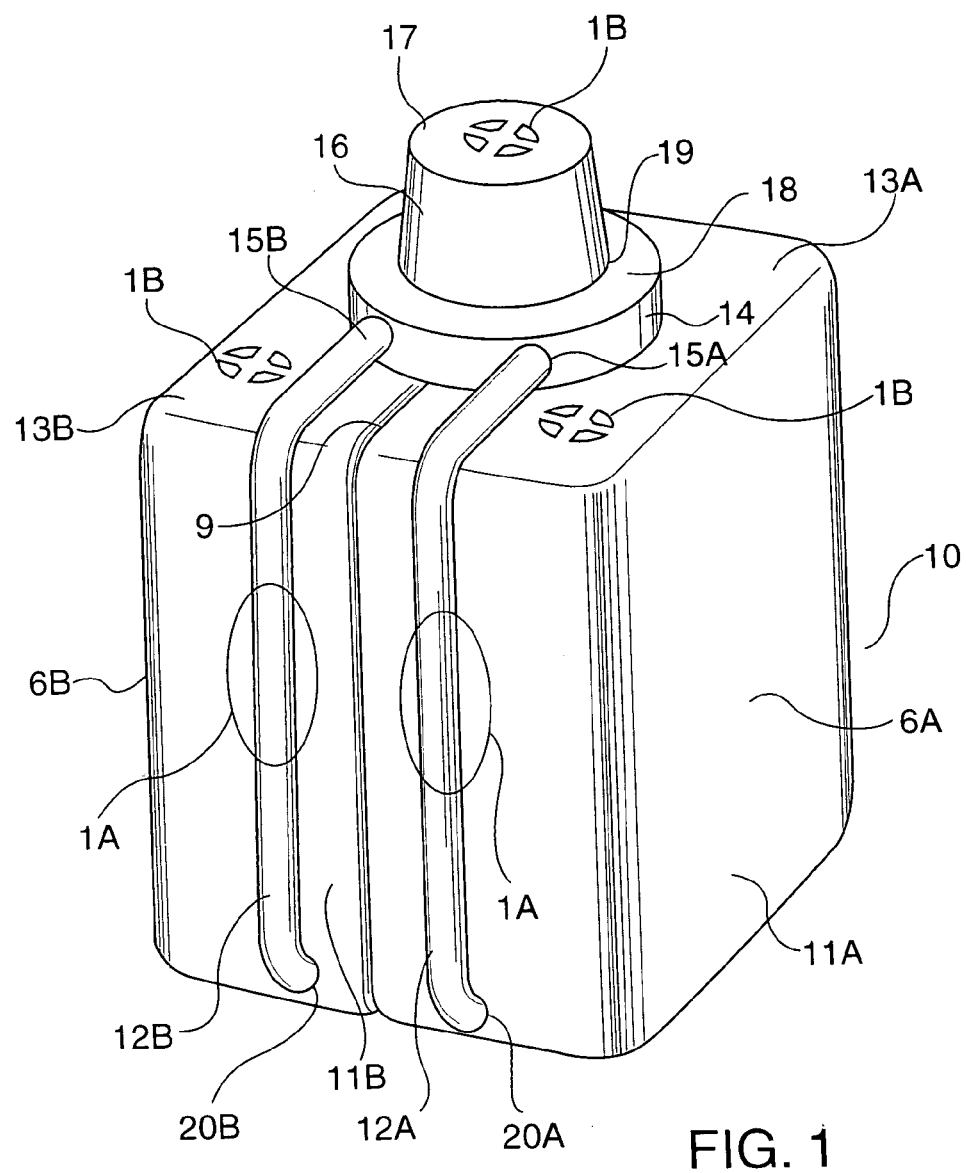
FIG. 1 is a front perspective view of a first embodiment of the multi-compartment storage and delivery container of our invention, a dual compartment storage and delivery container with the vertically-positioned parallel fluidic composition communication tubes thereof, 12A and 12B, being located at the front of the container.
Figure 1A:
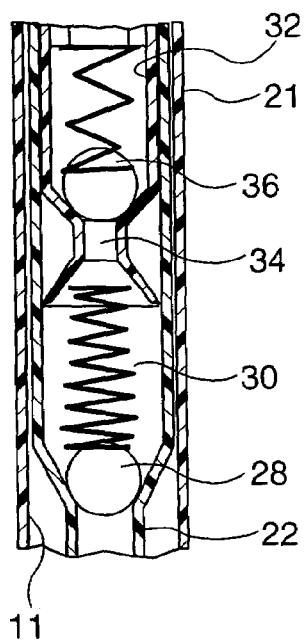
FIG. 1A is a detailed cut-away side elevation view of an inner section of fluidic composition communication tube 12A or 12B of the storage and delivery container of FIG. 1 showing a one-way fluidic composition flow check valve contained therein, also shown in FIGS. 2, 3, 4A, 6, 8, 11, 27A and 27B.
Figure 1B:
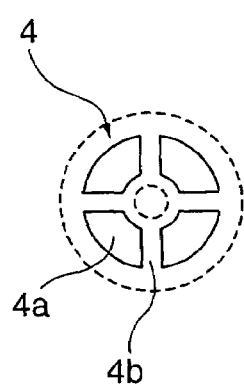
FIG. 1B is a detailed top view of air vent 1B located in each of storage member lids 13A and 13B and in the upper cap member base 17 of the storage and delivery container of FIG. 1, also shown in FIGS. 2, 3, 4A, 4B, 5, 6, 7, 8, 9, 10, 27A, 27B and 27C.
Figure 1B:
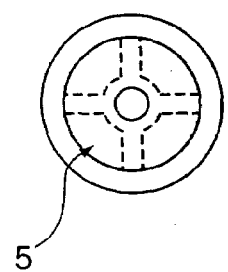
Figure 27F:
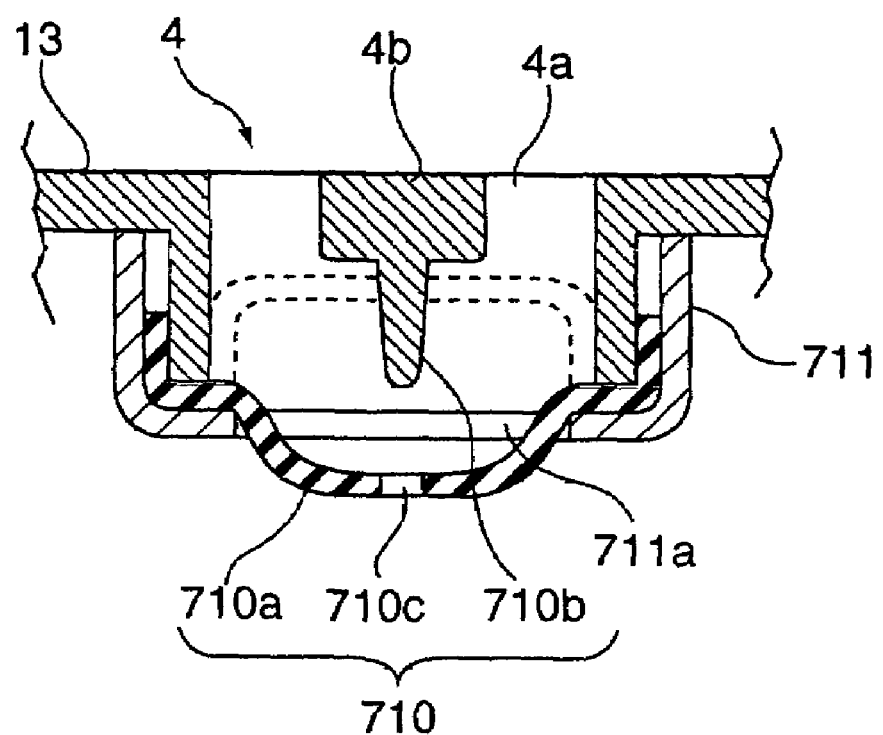

FIG. 27F is a detailed cut-away side elevation view of the air vent of FIGS. 1B and 1B'.

Figure 28A:
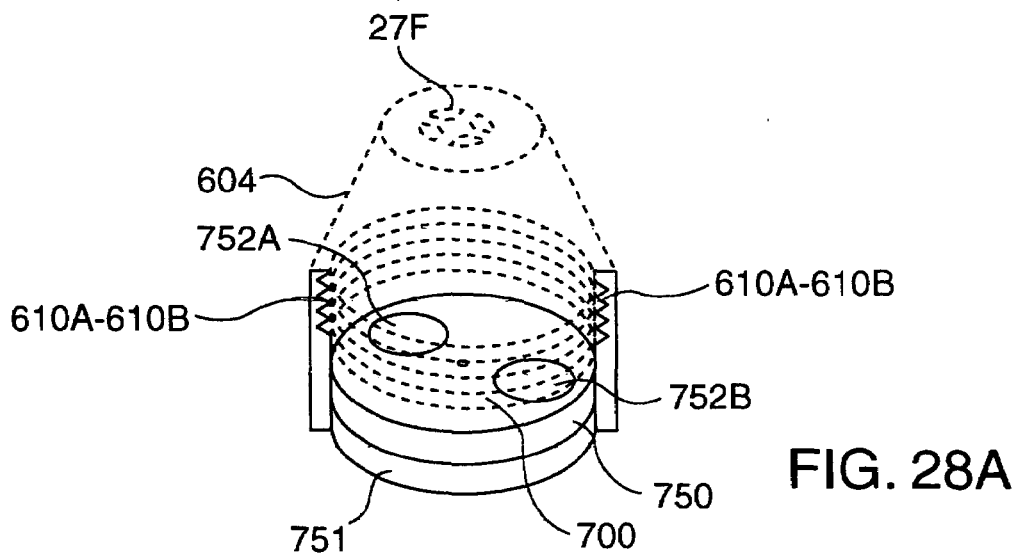

FIG. 28A is a schematic detailed perspective view of the cap member-mixing chamber compound lid assembly of the storage and delivery container of FIG. 27A, showing the positioning of the mixing chamber compound lid while the cap member is removably attached to the mixing chamber.

Figure 28B:
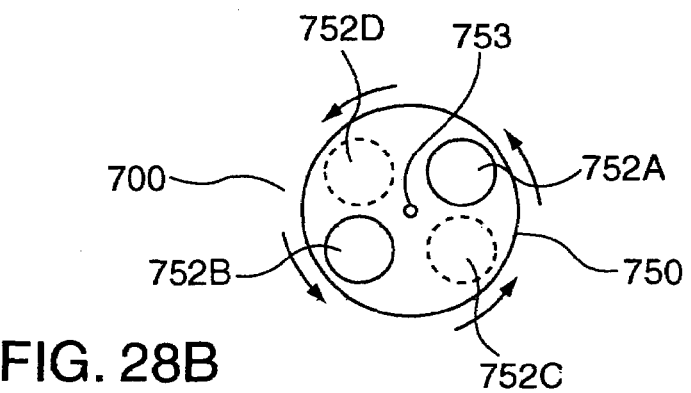
Figure 28C:
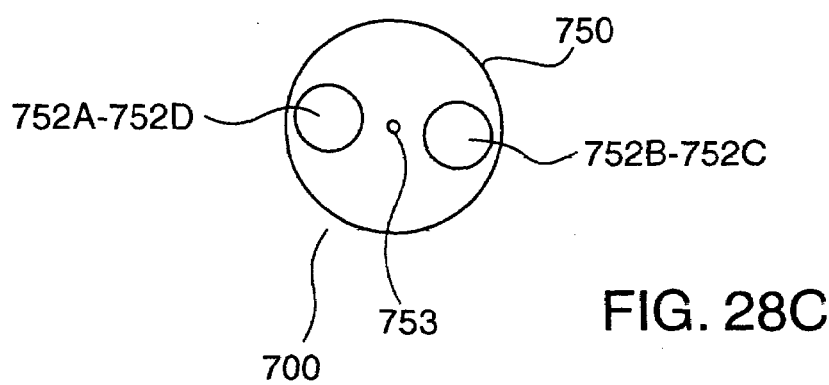

FIGS. 28B and 28C each shows a top view of the mixing chamber of the dual-compartment storage and delivery container of FIG. 27A having a mixing chamber compound lid containing orifices having adjustable dimensions with FIG. 28B showing the mixing chamber compound lid in a 'closed' position and FIG. 28C showing the mixing chamber compound lid in a fully open position.

DETAILED DESCRIPTION OF THE INVENTION

I. The Article of our Invention

The structural materials of the article compartments, air vent devices, communication tubes, check valve devices, fluidic composition flow control valves, mixing chamber, mixing chamber compound lid and cap member of the article of our invention must necessarily be chemically non-reactive and physically non-interactive with (i) the individually stable, pre-storable fluidic compositions (and constituents thereof) to be contained within each of the isolatably separate compartments of the article, as well as (ii) the unstable mixtures and components thereof formed within the mixing chamber of the article of our invention.

The term "chemically non-reactive" is herein intended to mean that during an extended reasonable time period of storage and repeated use, e.g. one year, the chemical structure of the materials of construction of the article compartments, air vent devices, communication tubes, check valve devices, fluidic composition flow control valves, mixing chamber, mixing chamber compound lid and cap member will be unaffected as a result of contact therewith by (i) the individually stable, pre-storable fluidic compositions (and constituents thereof) contained within each of the isolatably separate compartments of the article, as well as (ii) the unstable mixtures and components thereof formed within the mixing chamber of the article of our invention.

The term "physically non-interactive" is herein intended to mean that during an extended reasonable period of storage and repeated use, e.g. one year, the physical structure and/or physical properties, e.g. tensile strength and melt flow index (in the case of a polymeric material of construction), of the article compartments, air vent devices, communication tubes, check valve devices, fluidic composition flow control valves, mixing chamber, mixing chamber compound lid and cap member will not be adversely affected as a result of contact therewith by (i) the individually stable, pre-storable fluidic compositions (and constituents thereof) to be contained within each of the isolatably separate compartments of the article, as well as (ii) the unstable mixtures and components thereof formed within the mixing chamber of the article of our invention.

In addition, the operability of the article of our invention in accordance with the process of our invention necessitates a requirement for (i) continuously adequate flexibility or elastic deformability of each of the walls of the isolatably separate compartments as well as the fluidic composition communication tubes of our invention; (ii) continuously sufficient tensile strength and compressive strength and (iii) appropriate dimensions (e.g. wall thickness) of the base, the walls, the mixing chamber walls and the fluidic composition communication tubes which constitute the article of our invention in order to support the weight of the contents therein and the hydraulic pressure of the contents therein when as a result of manual pressure applied to the walls of the article, or pressure exerted on the fluidic compositions contained in the storage member compartments from other sources, the pre-stored, stable compositions contained each of the separate compartments are transported from the storage compartments through the fluidic composition communication tubes into the mixing chamber of the article of our invention.

Accordingly, the materials of construction of the article of our invention include metal alloys such as aluminum-titanium alloys and stable polymers, including, but not limited to high molecular weight medium density polyethylene, high molecular weight medium density polypropylene, polytesters, polymethylmethacrylate and styrene-butadiene elastomers. Preferred materials of construction are polymers described in the following U.S. Pat. Nos. 6,770,715; 6,787,589; 6,790,921 and 6,797,756.

With respect to the dimensions of the article of our invention, such dimensions will vary and depend upon the use to which the article is put, e.g. cleaning systems, oral care systems, fabric care systems, color forming systems and adhesion systems. Preferably when the article is thus used, the storage member separate compartment wall and base thickness is in the range of from about 0.2 to about 0.5 centimeters; the height of each storage member is in the range of from about 10 to about 30 cm.; the middle width of each storage member is in the range of from about 5 to about 15 cm.; the circumference of each horizontally-disposed planar storage member base is from about 10 cm. to about 80 cm.; the circumference of each horizontally-disposed planar storage member lid is from about 15 cm. to about 80 cm.; the circumference of the horizontally-disposed substantially planar mixing base is from about 10 cm. to about 70 cm.; the height of the upright hollow mixing chamber is from about 1.5 cm. to about 5 cm.; the circumference of the mixing chamber upper inner orifice rim is from about 10 cm. to about 70 cm.; the height of the hollow cap member is from about 4 cm. to about 10 cm.; the circumference of the substantially planar horizontally-disposed upper cap base is from about 8 cm. to about 20 cm.; and the internal diameter of each of the storage member-mixing chamber fluidic composition communication tubes is from about 0.5 cm. to about 2 cm.

Each of the fluidic composition communication tubes of the article of our invention preferably includes a one-way check valve, the purpose of which is to prevent a back-flow of unstable mixture into one or more of the separate compartments of the storage member immediately subsequent to the formation of the unstable mixture in the mixing chamber. A preferred check valve for use with the article of our invention is of the type disclosed in U.S. Pat. No. 3,760,986.

In order to enable repeated smooth introductions of stable fluidic compositions from each of the separate storage member compartments into the mixing chamber, it is preferable to employ air vents in the planar storage member lids and/or in the cap base, whereby such air vents, closed when the article is not in operation, are opened to supply outside air into each of the separate storage member compartments and the mixing chamber when the interiors of those parts of the article of our invention are subjected to negative internal pressure immediately after the formation of the unstable mixture in the mixing chamber. A preferred air vent device for use with the article of our invention is of the type disclosed in published U.S. patent application Ser. No. 2003/0168462 A1 and specified in FIG. 5 and the description thereof.

The article of our invention enables provision to a solid or semi-solid surface or to a liquid phase or vapor phase three-dimensional volume of a mixture of two, three or four compositions, one or more components of which chemically react and/or physically interact with another of the components of another of the compositions and whose reaction and/or interaction is desired to occur on the aforementioned solid or semi-solid solid surface or in the aforementioned liquid phase or vapor phase three-dimensional volume but not in the container wherein the aforementioned two, three or four compositions are stored. Examples of this type of system include:

Cleaning systems in which (i) an alkaline material and (ii) an acid material and/or (i) an oxidative material and (ii) a reductive material are brought together on a solid or semi-solid surface and/or in a liquid-phase volume to provide, for example, an effervescing action, a cleansing action, and a dissolution of soil on a solid or semi-solid surface and/or in a liquid phase volume, e.g. utilizing the dual container article and drain-cleaning compositions stored therein, LIQUID-PLUMR®, Clorox Company or the dual container article and drain-cleaning compositions stored therein sold as DRAINO® or the dual container article and carpet care compositions stored therein sold as OXY KIC® and described in U.S. patent application Ser. No. 2004/0063600 A1 and illustrated in U.S. Design Pat. D484,038. Further examples of these systems are described in the following references: U.S. Pat. Nos. 4,206,068, 4,585,150, 4,858,758, 5,804,546, U.S. patent application Ser. Nos. 2003/0171234 A1, US 2004/0002434 A1, European Patent, EP 0 733 097 B1; and Published PCT Patent Application WO 98/33880, and 01/00765.

Other embodiments include:
(a) Oral care systems in which (i) an oxidative material and (ii) a reductive material are brought together in the oral cavity to provide a cleansing action therein, e.g. utilizing the container article and sold as, MENTADENT® described in U.S. Pat. Nos. 4,528,180 and 4,687,663;

(b) Liquid personal care products in which (i) a body wash, a lotion, a cream, a shampoo, a hair conditioner, a hair color former and/or a hair color modifier, e.g. a hair bleach and (ii) a fluidic microencapsulated fragrance and/or benefit composition, e.g. an aqueous slurry of microencapsulated fragrance and/or benefit agent are admixed with such systems being described in the following U.S. Pat. Nos. 5,612,044, 6,767,534, 6,767,875, 6,770,103, and 6,790,434.

(c) Multi-component pharmaceutical formulations where one component is an oxidizing agent and the second component is a reducing agent with such a system being described in U.S. Pat. No. 6,790;

(d) Liquid fabric care products in which (i) a liquid detergent, e.g. that disclosed in U.S. Pat. Nos. 5,723,434 and 5,656,585 5,403,499, 5,411,671 5,574,179 and 5,562,849 and (ii) a fluidic microencapsulated fragrance and/or benefit agent composition, e.g. an aqueous slurry of microencapsulated fragrance and/or benefit agent as disclosed in U.S. patent application Ser. No. 10/823,033 filed on Apr. 13, 2004, are brought together on a solid or semi-solid surface or in a temporarily-storable admixture to provide an appropriately-treated solid or semi-solid surface e.g. a fabric surface or a cookware surface, with such system being described in the following U.S. Pat. Nos. 6,794,356 and 6,794,346;

(e) color forming systems in which (i) a first dye precursor and (ii) a second dye precursor are brought together and the resulting dye is appropriately applied to a surface or subsequently admixed with other appropriate components with such system being described in the following U.S. Pat. Nos. 6,776,308 and 6,790,819;

(f) Adhesion systems and/or plumbing systems in which (i) a pre-polymer such as an epoxy resin pre-polymer, e.g. the reaction product of epichlorohydrin and bis-phenol-A or a cross-linkable vinyl polymer such as a low molecular weight polyacrylic acid-polyacrylamide co-polymer, (ii) optionally a cross- linking agent such as a melamine-formaldehyde cross-linker and (iii) a curing catalyst are brought together at the junction of two solid surfaces of two articles in order to permanently adhere the article surfaces, one to the other, for example, using the package instructions for the epoxy resin pre-polymer—curing agent system sold as WELD® and Versa-Chem® 4 Minute Epoxy Steel Quick Set Type 44 with such systems being described in the following U.S. Pat. Nos.: 6,764,986; 6,784,224; 6,784,248; 6,790,919 and 6,794,479; and (g) Shelf-stable liquid pre-mixes separated into two or more components that are combinable to form food beverage products as described in U.S. Pat. No. 6,056,984;

II. The system of our invention for simultaneously (i) substantively imparting a fragrance and/or benefit agent to a solid or semi-solid surface or liquid-phase or gaseous-phase defined volume and (ii) treating said solid or semi-solid surface or liquid-phase or gaseous-phase defined volume with a fluidic surface or volume treatment agent composition.

(a) The Pre-Stored Stable Aqueous Slurry System

The pre-stored stable aqueous slurry system useful in the practice of our invention is, in general, a stable suspension of microencapsulated fragrance and/or benefit agent in an aqueous emulsion containing water, additional fragrance and/or benefit agent and an emulsifier having an HLB hydrophile-lipophile balance of from about 6 to about 40, with the provisos that (a) when using a non-ionic emulsifier the HLB value is in the range of from about 6 to about 20;

(b) when using an anionic emulsifier, the HLB value is in the range of from about 10 to about 40; and (c) when using a zwitterionic emulsifier, the HLB value is in the range of from about 6 to about 12.

as disclosed in U.S. patent application Ser. No. 10/823,033 filed on Apr. 13, 2004. More specifically, the stable suspension of our invention has a viscosity of from about 500 to about 20,000 centipoises at a shear rate of from about 0.5 to about 2.0 seconds$^{-1}$ and at about 25° C. which viscosity undergoes a minimal increase over an extended period of time on storage.

The term stable suspension is herein intended to mean a suspension of microencapsulated fragrance and/or benefit agent in an aqueous oil-in-water emulsion of non-confined fragrance and/or benefit agent where, on storage, over an extended period of time, no settling or precipitation of the microencapsulated fragrance and/or benefit agent occurs and the emulsion surrounding the microcapsules remains as a stable emulsion in the absence of separation into finite discrete non-emulsified liquid phases, an aqueous phase and an oil phase.

More specifically, the suspension useful in the practice of our invention comprises (a) from about 10% by weight to about 90% by weight of a non-confined liquid-phase which is a substantially solid particle-free first fragrance composition and/or a substantially solid particle-free first benefit agent composition comprising from about 10% to about 90% by weight of a hydrophobic fragrance and/or hydrophobic benefit agent, from about 0.5% to about 10% of an emulsifier based on the weight of the non-confined fragrance and from about 10% to about 90% water, in the form of a stable oil-in-water emulsion and (b) stably suspended in said non-confined liquid-phase from about 10% to about 90% by weight of a plurality of rupturable microcapsules each of which has (i) has an outside diameter in the range of from about 0.01 to about 1000 microns; (ii) has a wall thickness in the range of from about 0.01 to about 100 microns; (iii) has a wall composed of a rupturable polymer; and (iv) has a liquid phase monophasic core comprising a substantially solid particle-free second fragrance composition and/or substantially solid particle-free second benefit agent composition with the composition of each of the monophasic cores of each of said rupturable microcapsules being (A) the same and/or different from one another and (B) the same or different from the first fragrance composition and/or first benefit agent composition wherein the weight % of substantially solid particle-free second fragrance composition and/or substantially solid particle-free second benefit agent composition initially contained in each of the rupturable microcapsules is from about 5% to 90% by weight of the rupturable microcapsules.

Among the emulsifiers that may be employed are (a) non-ionic emulsifiers having HLB values in the range of from about 6 to about 20, a number of examples of which are set forth in the following Table VIIa together with their respective HLB values:

TABLE VIIA

| Common Name ("TWEEN ®", "SPAN ®" and "ATLAS ®" of ICI Americas Inc. | Chemical Designation | HLB Value |
|---|---|---|
| SPAN 40 | Sorbitan monpalmitate | 6.7 |
| ATLAS G-2800 | Polyoxypropylene mannitol dioleate | 8.0 |
| PEG 400 monolaurate | polyoxyethylene monolaurate | 13.1 |
| TWEEN 60 | polyoxyethylene sorbitan monostearate | 14.9 |
| TWEEN 40 | polyoxyethylene sorbitan monopalmitate | 15.6 |
| TWEEN 20 | polyoxyethylene sorbitan monolaurate | 16.7 |
| ATLAS G-2159 | polyoxyethylene monostearate | 18.8 |

(b) anionic emulsifiers having HLB values in the range of from about 10 to about 40, a number of examples of which are set forth in the following table VIIb together with their respective HLB values:

TABLE VIIB

| Common Name | Chemical Name | HLB Value |
|---|---|---|
| ATLAS G-3300 | An alkyl aryl sulfonate | 11.7 |
| Triethanolamine oleate | Triethanolamine oleate | 12 |
| Sodium Oleate | Sodium Oleate | 18 |
| Potassium Oleate | Potassium Oleate | 20 |
| Sodium Lauryl Sulfate | Sodium Lauryl Sulfate | 40 | and (c) zwitterionic emulsifiers having HLB values in the range of from about 6 to about 12, which are 'lecithins' containing one or more phosphatidyl cholines, phosphatadylethanolamines and/or phosphatidylinositols, a number of examples of which are set forth in the following table VIIc, together with their respective HLB values:

TABLE VIIC

| Common Name Products of Central Soya Company Inc. | HLB Value |
|---|---|
| Centrophase ® HR 4B | 7.5 |
| Blendmax ® K | 8.0 |
| Centrolene ® A | 10 |
| Centromix ® E | 12 |
| Centromix ® CPS | 12 |

With respect to the microcapsules employed in the practice of our invention, those disclosed in the following U.S. Patents and published patent applications as well as in application Ser. No. 10/823,033 filed on Apr. 13, 2004 as well as the following disclosures U.S. Pat. Nos. 3,505,432; 4,496,467; 4,521,541; 6,213,409; 6,790,543; U.S. patent application Ser. Nos. 2001/0008874 A1; 2004/0005830 A1; 2004/0138093 A1; 2004/014828 A1 and PCT Application WO 03/074580.

The microcapsule walls are preferably composed of an aminoplast resin, more specifically a substituted or un-substituted acrylic acid polymer or co-polymer cross-linked with a urea-formaldehyde pre-condensate or a melamine-formaldehyde pre-condensate. The microcapsule is formed by means of either (a) forming an aqueous dispersion of a non-cured aminoplast resin by reacting under acidic pH conditions a urea-formaldehyde pre-condensate or a melamine-formaldehyde pre-condensate with one or more substituted or un-substituted acrylic acid polymers or co-polymers; then coacervating the resulting non-cured aminoplast resin shell about the surface of a fragrance and/or malodour counteractant-solvent monophasic droplet under homogenization and then curing the microcapsule shell wall at an elevated temperature, e.g. 50-85° C. or (b) forming the aminoplast resin wall at the surface of the fragrance and/or malodour counteractant—solvent monophasic droplet by means of reacting, at the surface of the droplet a urea-formaldehyde pre-condensate or a melamine-formaldehyde pre-condensate with one or more substituted or un-substituted acrylic acid polymers or co-polymers, and then curing the microcapsule shell wall at an elevated temperature, e.g. 50-85° C.

Microcapsule formation using mechanisms similar to the foregoing mechanism, using (i) melamine-formaldehyde or urea-formaldehyde pre-condensates and (ii) polymers containing substituted vinyl monomeric units having proton-donating functional group moieties (e.g. sulfonic acid groups or carboxylic acid anhydride groups) bonded thereto is disclosed in U.S. Pat. No. 4,406,816 (2-acrylamido-2-methylpropane sulfonic acid groups), UK published Patent Application GB 2,062,570 A (styrene sulfonic acid groups) and UK published Patent Application GB 2,006,709 A (carboxylic acid anhydride groups).

The cross-linkable acrylic acid polymer or co-polymer microcapsule shell wall precursor has a plurality of carboxylic acid moieties:

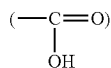

and is preferably one or a blend of the following:

(i) an acrylic acid polymer;

(ii) a methacrylic acid polymer;

(iii) an acrylic acid-methacrylic acid co-polymer;

(iv) an acrylamide-acrylic acid co-polymer;

(v) a methacrylamide-acrylic acid co-polymer;

(vi) an acrylamide-methacrylic acid co-polymer;

(vii) a methacrylamide-methacrylic acid co-polymer;

(viii) a $C_1$-$C_4$ alkyl acrylate-acrylic acid co-polymer;

(ix) a $C_1$-$C_4$ alkyl acrylate-methacrylic acid co-polymer;

(x) a $C_1$-$C_4$ alkyl methacrylate-acrylic acid co-polymer;

(xi) a $C_1$-$C_4$ alkyl methacrylate-methacrylic acid co-polymer;

(xii) a $C_1$-$C_4$ alkyl acrylate-acrylic acid-acrylamide co-polymer;

(xiii) a $C_1$-$C_4$ alkyl acrylate-methacrylic acid-acrylamide co-polymer;

(xiv) a $C_1$-$C_4$ alkyl methacrylate-acrylic acid-acrylamide co-polymer;

(xv) a $C_1$-$C_4$ alkyl methacrylate-methacrylic acid-acrylamide co-polymer;

(xvi) a $C_1$-$C_4$ alkyl acrylate-acrylic acid-methacrylamide co-polymer;

(xvii) a $C_1$-$C_4$ alkyl acrylate-methacrylic acid-methacrylamide co-polymer;

(xviii) a $C_1$-$C_4$ alkyl methacrylate-acrylic acid-methacrylamide co-polymer; and (xix) a $C_1$-$C_4$ alkyl methacrylate-methacrylic acid-methacrylamide co-polymer.

and more preferably, an acrylic acid-acrylamide copolymer.

When substituted or un-substituted acrylic acid co-polymers are employed in the practice of our invention, in the case of using a co-polymer having two different monomeric units, e.g. acrylamide monomeric units and acrylic acid monomeric units, the mole ratio of the first monomeric unit to the second monomeric unit is in the range of from about 1:9 to about 9:1, preferably from about 3:7 to about 7:3. In the case of using a co-polymer having three different monomeric units, e.g. ethyl methacrylate, acrylic acid and acrylamide, the mole ratio of the first monomeric unit to the second monomeric unit to the third monomeric unit is in the range of 1:1:8 to about 8:8:1, preferably from about 3:3:7 to about 7:7:3.

The molecular weight range of the substituted or un-substituted acrylic acid polymers or co-polymers useful in the practice of our invention is from about 5,000 to about 1,000,000, preferably from about 10,000 to about 100,000. The substituted or un-substituted acrylic acid polymers or co-polymers useful in the practice of our invention may be branched, linear, star-shaped, dendritic-shaped or may be a block polymer or copolymer, or blends of any of the aforementioned polymers or copolymers.

The urea-formaldehyde and melamine-formaldehyde pre-condensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing our invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g. methanol, ethanol, 2-propanol, 3-propanol, 1-butanol, 1-pentanol or 1-hexanol, thereby forming a partial ether where the mole ratio of melamine or urea:formalhyde:alkanol is in the range of 1:(0.1-6):(0.1-6). The resulting ether moiety-containing product may by used 'as-is' as a cross-linking agent for the aforementioned substituted or un-substituted acrylic acid polymer or copolymer, or it may be self-condensed to form dimmers, trimmers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. No. 3,516,846, 6,261,483, and Lee et al. J. Microencapsulation, 2002, Vol. 19, No. 5, pp 559-569, "Microencapsulation of fragrant oil via in situ polymerization: effects of pH and melamine-formaldehyde molar ratio". Examples of urea-formaldehyde pre-condensates useful in the practice of our invention are URAC 180 and URAC 186, Cytec Technology Corp. Examples of melamine-formaldehyde pre-condensates useful in the practice of our invention are CYMEL U-60, CYMEL U-64 and CYMEL U-65, Cytec Technology Corp. In the practice of our invention it is preferable to use as the precondensate for cross-linking the substituted or un-substituted acrylic acid polymer or co-polymer the melamine-formaldehyde pre-condensate having the structure:

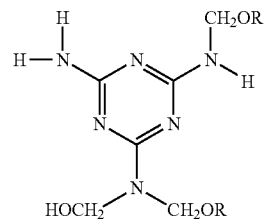

wherein each of the R groups are the same or different and each represents hydrogen or $C_1$-$C_6$ lower alkyl, e.g. methyl, ethyl, 1-propyl, 2-propyl, 1-butyl, 2-butyl, 2-methyl-1-propyl, 1-pentyl, 1-hexyl and/or 3-methyl-1-pentyl.

In practicing our invention, the range of mole ratios of urea-formaldehyde precondensate or melamine-formaldehyde pre-condensate: substituted or un-substituted acrylic acid polymer or co-polymer is in the range of from about 9:1 to about 1:9, preferably from about 5:1 to about 1:5 and most preferably from about 1:2 to about 2:1.

The average outside diameter of the resulting microcapsule is in the range of from about 0.01 microns to about 1000 microns; preferably from about 0.05 microns to about 100 microns and more preferably from about 2.0 microns to about 20 microns. The average wall thickness of the resulting microcapsule is in the range of from about 0.01 microns to about 100 microns; preferably from about 0.05 microns to about 10 microns and more preferably from about 0.2 microns to about 2.0 microns.

The content of the resulting microcapsule includes a fragrance composition and/or a benefit agent such as a malodour counteractant composition in combination with a compatible hydrophobic solvent. The term "compatible" is herein intended to mean chemically non-reactive with every fragrance component and/or benefit agent such as a malodour counteractant component and capable of forming a single liquid phase with each fragrance composition component and with each benefit agent component such as a malodour counteractant composition component. In the practice of our invention, the range of weight percent of solvent/fragrance composition components and/or solvent/malodour counteractant composition components contained in each of the microcapsules is from about 50% to about 97% by weight of the microcapsule, preferably from about 91% to about 96%. Thus, the range of weight ratios of encapsulating polymer to solvent/fragrance composition components and/or solvent/malodour counteractant components is from about 1:25 to about 1:1; preferably from about 1:10 to about 4:96. In addition, the range of weight percent of solvent in the microcapsule is from about 10% to 80% by weight of the filled microcapsule. The preferred ratio of weight of solvent: weight of encapsulated fragrance composition and/or encapsulated malodour counteractant composition is from about 2:1 to about 1:2, with the most preferred ratio being 1:1.

The compatible hydrophobic solvent used in combination with the microencapsulated fragrance composition and/or microencapsulated benefit agent, e.g. malodour counteractant composition is preferably a mono-, di- or tri-$C_4$-$C_{26}$ saturated or unsaturated fatty acid glyceride, diethyl phthalate, dibutyl phthalate, diisodecyl adipate, a liquid polydimethyl siloxane, a liquid polydimethylcyclosiloxane, the methyl ester of soya fatty acid, a mixture of soya fatty acid methyl ester and isopropyl myristate with the weight ratio of soya fatty acid:isopropyl myristate being from 2:1 to 20:1 and a mineral oil compatible with each component of said fragrance composition and/or said benefit agent, e.g. malodour counteractant composition. More preferably, the solvent is a tri-$C_4$-$C_{26}$ saturated or unsaturated fatty acid glyceride. Most preferably, the solvent is the tri-glyceride ester of a mixture of caprylic acid and capric acid, commercially available as NEOBEE M-5, Stepan Chemical Company. The C $\log_{10}$P' of the solvent is greater than 3.3, where P' is the n-octanol/water partition coefficient of the hydrophobic solvent; preferably greater than about 8 and most preferably greater than about 10.

The C $\log_{10}$P of each component of the encapsulated fragrance composition and/or the encapsulated malodour counteractant composition preferably is in the range of from about 3.3 to about 8, where P is the n-octanol/water partition coefficient of the fragrance component, although relatively low percentages of fragrance components having a lower value of C $\log_{10}$P may be used in conjunction with the components having a C $\log_{10}$P of between 3.3 and 8.

The values of $\log_{10}$P have been reported; for example, the Pomona92 database, available from Daylight Chemical Information Systems, Inc., Daylight CIS, Irvine, Calif. However, the $\log_{10}$P values are most conveniently calculated by the "CLOGP" program, also available from Daylight CIS. This program also lists experimental $\log_{10}$P values when they are available in the Pomona92 database. The "calculated $\log_{10}$P" (C $\log_{10}$P) is determined by the Hansch and Leo "fragment" approach based on the chemical structure of each functional product ingredient, and takes into account the numbers and types of atoms, the atom connectivity and the chemical bonding. The C $\log_{10}$P values which are the most reliable and widely used estimates for this physicochemical property, are preferably used instead of the experimental $\log_{10}$P values for the selection of functional ingredients, including perfume ingredients which are useful components in the microencapsulate-containing slurries useful in the practice of our invention.

Specific examples of preferred fragrance components useful in the aminoplast microencapsulates used in the practice of our invention, and the molecular weights and C $\log_{10}$P values of each of said components are set forth in Table IX as follows:

TABLE IX

| Fragrance Component | Clog$_{10}$P value | Molecular Weight |
| --- | --- | --- |
| amyl salicylate | 4.601 | 208.26 |
| benzyl salicylate | 4.383 | 228.25 |
| β-caryophyllene | 6.333 | 204.36 |
| ethyl undecylenate | 4.888 | 212.34 |
| geranyl anthranilate | 4.216 | 273.38 |
| α-irone | 3.820 | 206.33 |
| β-phenyl ethyl benzoate | 4.058 | 226.28 |
| α-santalol | 3.800 | 220.36 |
| amyl salicylate | 4.601 | 208.26 |
| β-caryophyllene | 6.333 | 204.36 |
| cedrol | 4.530 | 222.37 |
| cedryl acetate | 5.436 | 264.41 |
| cedryl formate | 5.070 | 238.37 |
| cyclohexyl salicylate | 5.265 | 220.29 |
| γ-dodecalactone | 4.359 | 198.31 |
| β-phenylethyl phenyl acetate | 3.767 | 240.31 |
| 5-acetyl-1,1,2,3,6-hexamethyl indane | 5.977 | 258.41 |
| cyclopentadecanolide | 6.246 | 240.39 |
| amyl cinnamic aldehyde | 4.324 | 202.30 |
| linalyl benzoate | 5.233 | 258.36 |

Specific examples of malodour counteractant composition components useful in the aminoplast microencapsulates used in the composition and process of our invention are as follows:

Malodour Counteractant Component Group I 1-cyclohexylethan-1-yl butyrate; 1-cyclohexylethan-1-yl acetate; 1-cyclohexylethan-1-ol;

1-(4'-methylethyl)cyclohexylethan-1-yl propionate; and

2'-hydroxy-1'-ethyl(2-phenoxy)acetate each of which compound is marketed as VEILEX® by International Flavors & Fragrances Inc.

Malodour Counteractant Component Group II

β-naphthyl methyl ether; β-naphthyl ketone; benzyl acetone:mixture of hexahydro-4,7-methanoinden-5-yl propionate and hexahydro-4,7-methanoinden-6-yl propionate;4-(2,6,6-trimethyl-2-cyclohexen-1-yl)-3-methyl-3-buten-2-one; 3,7-dimethyl-2,6-nonadien-1-nitrile; dodecahydro-3a, 6,6,9a-tetramethylnaphtho(2,1-b)furan; ethylene glycol cyclic ester of n-dodecanedioic acid; 1-cyclohexadecen-6-one; 1-cycloheptadecen-10-one; and corn mint oil.

Preferred insect repellent agents useful in the practice of our invention are disclosed in the following U.S. Pat. Nos. 5,633,236; 5,665,781; 5,753,686 and 5,798,385.

Preferred insect repellent components useful in the practice of our invention are geraniol, geranium oil, citral and nerol.

Optionally, in order to provide an increased period of time during which the microencapsulates are retained on surfaces to be treated using the consumable products into which the suspensions of our invention are incorporated, the aminoplast microencapsulates used in the practice of our invention may be coated with a cationic polymer as disclosed in U.S. patent application Ser. Nos. 2004/0142828 and 2004/0138093. The rate of use of such cationic polymer coatings on the microencapsulates is from about 1% to about 3000% by weight of the filled microencapsulates; preferably from about 5% to about 1000% by weight of the filled microencapsulates; and most preferably from about 10% to about 500% by weight of the filled microencapsulates.

Examples of such cationic polymers used as coatings are cationically modified starch and cationically modified guar, polymers comprising poly diallyl dimethyl ammonium halides (PolyDADMAC), and copolymers of DADMAC with vinyl pyrrolidone, acrylamides, imidazoles, imidazolinium halides, and the like. For instance, Polyquaternium-6, 7, 22 and 39, available from Ondeo Nalco.

The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc.

The preferred cationic guar has a molecular weight of from about 50,000 to about 5,000,000. The preferred cationic guar products are Jaguar C-162 and Jaguar C-17 and are commercially available from Rhodia Inc.

Additional examples of cationic polymers useful for coating the aminoplast encapsulated solvent/fragrance compositions and/or solvent/malodour counteractant compositions of our invention are the water-soluble cationic amino resins, cationic urea resins, specifically, urea-formaldehyde prepolymers subjected to polycondensation with a cationic modifier such as diethylenetriamine, tetraethylene pentamine, guanidine, guanyl urea and oxazolidine as disclosed in published U.S. patent application Ser. No. US 2001/0008874, for example U-RAMIN P-1500, a urea-formaldehyde prepolymer modified with diethylene triamine.

An additional embodiment of the invention includes a stable suspension of microencapsulated fragrances in an oil-in-water emulsion as set forth supra, where the capsule wall is relatively permeable. The details of such microencapsulated fragrances are set forth in co-pending application for U.S. Letters patent Ser. No. 10/718,240 filed on Nov. 20, 2003 (IFF 56). In such a case, since the capsule wall is permeable, it is possible for capsules containing a core of hydrophobic or high C $\log_{10}P$ fragrance materials optionally in combination with one or more high C $\log_{10}P$ compatible solvents to actually absorb fragrance materials from a fragrance containing base, e.g. a fragranced fabric conditioner/softener base such as that described in U.S. Pat. No. 5,411,671. This process can be improved via the initial inclusion of a more soluble solvent, which may be a lower C $\log_{10}P$ material, in the core which partitions out of the core when placed in the base, thus providing free volume for fragrance material initially present in the base to occupy.

The migration of fragrance materials into the capsule also provides for the production of capsules by simply loading the capsules into a high concentration of fragrance material. The fragrance materials will preferably migrate into the core of the capsules. This allows an encapsulated fragrance to be manufactured by the selection of a permeable capsule material and hydrophobic core and immersing the capsules in a liquid system that contains a high fragrance loading.

In such case, each of the rupturable microcapsules is a permeable microcapsule containing at least 20 weight percent of a 'sacrificial' solvent capable of migrating outside of the capsule over a period of time ranging from about 50 hours to about 200 hours. Preferable 'sacrificial' solvents are benzyl acetate and n-octanol or mixtures thereof, e.g. a 40:60 weight weight mixture of benzyl acetate and n-octanol.

The non-confined fragrance and/or benefit agent composition in the stable suspension useful in the practice of our invention is contained in the "oil-in-water" emulsion droplets which are part of the emulsion in which the microencapsulated fragrance and/or benefit agent is suspended. The C $\log_{10}P$ range of each of the non-confined fragrance and/or benefit agent components is in the range of from about 1 to about 8 thus enabling a greater range of fragrance and/or benefit agent component types in the non-confined fragrance and/or benefit agent as opposed to the components of the confined or microencapsulated fragrance and/or benefit agent.

Within the scope of our invention, each of the oil phase component droplets of the emulsion containing non-confined fragrance and/or benefit agent has a diameter in the range of from about 0.01 to about 1 microns; preferably in the range of from about 0.05 to about 0.8 microns, and more preferably in the range of from about 0.1 to about 0.5 microns.

Specific examples of non-confined fragrance components, their molecular weights and their C $\log_{10}P$'s are set forth in the following Table XI:

TABLE XI

| Fragrance Component | $C\log_{10}P$ value | Molecular Weight |
|---|---|---|
| benzaldehyde | 1.480 | 106.12 |
| benzyl acetate | 1.960 | 150.17 |
| laevo-carvone | 2.083 | 150.22 |
| geraniol | 2.649 | 154.26 |
| cis-jasmone | 2.712 | 164.25 |
| β-phenylethyl alcohol | 1.183 | 122.17 |
| α-terpineol | 2.569 | 154.25 |

TABLE XI-continued

| Fragrance Component | $C\log_{10}P$ value | Molecular Weight |
|---|---|---|
| 1-phenyl hexanol-5 | 3.299 | 178.28 |
| dihydromyrcenol | 3.03 | 156.27 |
| δ-undecalactone | 3.830 | 184.28 |
| amyl cinnamate | 3.771 | 218.30 |
| benzophenone | 3.120 | 182.22 |
| nerol | 2.649 | 154.25 |
| 2-methoxynaphthalene | 3.235 | 158.20 |
| ethyl undecylenate | 4.888 | 212.34 |
| geranyl anthranilate | 4.216 | 273.38 |
| α-irone | 3.820 | 206.33 |
| α-santalol | 3.800 | 220.36 |
| iso-eugenol | 2.547 | 164.21 |
| amyl salicylate | 4.601 | 208.26 |
| benzyl salicylate | 4.383 | 228.25 |
| β-caryophyllene | 6.333 | 204.36 |
| cedrol | 4.530 | 222.37 |
| cedryl acetate | 5.436 | 264.41 |
| cedryl formate | 5.070 | 238.37 |
| cyclohexyl salicylate | 5.265 | 220.29 |
| γ-dodecalactone | 4.359 | 198.31 |
| ethyl undecylenate | 4.888 | 212.34 |
| geranyl anthranilate | 4.216 | 273.38 |
| β-phenylethyl benzoate | 4.058 | 226.38 |
| β-phenylethyl phenyl acetate | 3.767 | 240.31 |
| 5-acetyl-1,1,2,3,3,6-hexamethyl indane | 5.977 | 258.41 |
| cyclopentadecanolide | 6.246 | 240.39 |
| d-limonene | 4.232 | 136.24 |
| cis-p-t-butylcyclohexyl acetate | 4.019 | 198.31 |
| amyl cinnamic aldehyde | 4.324 | 202.30 |

The non-confined fragrance and/or benefit agent composition useful in the practice of our invention may also contain at least one of the following auxiliary substances in amounts of from about 0.01% to about 10% by weight of the non-confined fragrance and/or benefit agent composition:

at least one deposition aid;
at least one additional surfactant;
at least one humectant;
at least one viscosity control agent; and
at least one solvent.

Examples of such auxiliary substances are set forth in co-pending U.S. Published application Ser. Nos. 2004/0142828 and 2004/0138093.

(b) The Pre-Storable Stable Fluidic Surface and/or Volume Treatment Composition

The stable, pre-storable fluidic surface and/or volume treatment compositions useful in the practice of our invention include various consumable articles including but not limited to liquid anionic, cationic, non-ionic or zwitterionic detergents, shampoos, body washes, soaps, hair conditioners, skin lotions, skin creams, skin moisturizers, anti-perspirants, deodorants and liquid fabric softener and/or fabric conditioner compositions. The following table sets forth U.S. Patents disclosing such consumable articles for mixing with the stable microencapsulated fragrance and/or benefit agent-containing suspensions useful in the practice of our invention to form unstable mixtures, including U.S. Pat. Nos. 5,403,499; 5,411,671; 5,562,849; 5,656,585, and 5,723,434.

For example, members of the following group of isotropic liquids disclosed in U.S. Pat. No. 5,723,434 are particularly useful as stable, pre-storable fluidic surface treatment compositions for admixing with a stable microencapsulated fragrance and/or benefit agent slurry suspension whereby an 'unstable' surface treatment composition for delivery to, for example, a washing machine simultaneously with the delivery to the washing machine of a fabric to be treated:

(i) 1% to 85% by wt. of a surfactant selected from the group consisting of anionic, cationic, amphoteric and zwitterionic surfactants and mixtures thereof;

(ii) 0.1% to 25% by wt. of a hydrotrope which is an organic polyol;

(iii) 0.1% to 20.0% by wt. of an electrolyte; and (iv) 0.1% to 10% by wt. of a polymer having a hydrophilic backbone and a tail comprising a monomeric unit comprising a pendant hydrophilic group and a pendant hydrophobic group.

(c) Multi-Compartment Containers Useful for the Operation of the System

The multi-compartment container groups useful for the operation of the system of our invention for simultaneously (i) substantively imparting a fragrance and/or benefit agent to a solid or semi-solid surface or liquid-phase or gaseous-phase defined volume and (ii) treating the solid or semi-solid surface or liquid-phase or gaseous-phase defined volume with a fluidic surface or volume treatment agent composition are not limited to the article of our invention as described supra, but may also include multi-component containers as disclosed in the following disclosures: U.S. Pat. Nos. 2,661,870; 2,941,694; 2,973,883; 3,269,389; 3,416,709; 4,687,663; 4,826,048; 5,252,312; 5,685,422; 5,740,947; 5,767,055 and 6,758,411, U.S. patent application Ser. No. 2004/0063600 A1 and U.S. Design Pat. D336,846; D484,038 and D495,949.

(d) Relevant Algorithms

When practicing our invention using, for example, a member of the group of isotropic liquids disclosed in U.S. Pat. No. 5,723,434 as a re-storable, individually stable surface treatment composition with a stable microencapsulated fragrance and/or benefit agent slurry suspension whereby an 'unstable' surface treatment composition for delivery to, for example, a washing machine simultaneously with the delivery to the washing machine of a fabric to be treated, the following algorithms have been determined:

(i) For the relationship of viscosity, v (in centipoises) vs time, $\theta$ (in minutes) for admixtures of suspension and liquid detergent compositions and/or fabric softener compositions:

$$(v-F)\left(\frac{T}{273}\right) = Ae^{-K\theta} - BLN(\theta + C) + D$$

wherein T is mixture temperature in degrees Kelvin and wherein $15 \leq A \leq 30$ $0.1 \leq K \leq 0.2$ $5 \leq B \leq 20$ $1 \leq C \leq 10$ $15 \leq D \leq 80$ $70 \leq F \leq 120$ (ii) For the relationship of change of viscosity with respect to time, $$\frac{\partial v}{\partial \theta}$$

(in centipoises/minute) vs time, $\theta$ (in minutes) for admixtures of suspension and liquid detergent composition and/or fabric softener composition:

$$\frac{\partial v}{\partial \theta} = -\alpha e^{-\kappa\theta} - \beta e^{-\lambda\theta} - \frac{J}{M+\theta} - \frac{Q}{N+\theta}$$

wherein $1 \leq \alpha \leq 2$ $1 \leq \beta \leq 2$ $0.1 \leq \kappa \leq 0.2$ $0.1 \leq \lambda \leq 0.2$ $20 \leq J \leq 40$ $1 \leq M \leq 2$ $5 \leq Q \leq 15$ $5 \leq N \leq 15$ Referring to FIGS. 1, 2, 3, 4A and 4B an article 10 for effecting the dispensing of a mixture of two fluidic compositions each of which fluidic composition has a chemical constituency different from any other of the fluidic compositions and each of which fluidic composition is chemically and/or physically reactive with each of the other fluidic compositions when in intimate contact therewith over a finite period of time, the article has:

(a) two upright hollow storage members 6A and 6B vertically juxtaposed to one-another at location 9. Each storage member has an internal storage 3-space. Each storage member 6A and 6B has a substantially horizontally-disposed substantially planar storage member base having a storage member base circumferential edge. Extending upwardly from the entirety of the storage member base circumferential edge is an elastically deformable vertically-disposed liquid-impermeable storage member sidewall 11A having an outer side and an inner side, terminating at its upper end at the entirety of the circumferential edge of a substantially horizontally-disposed planar storage member lid 13A and 13B. Each lid is shown to contain an air vent, 1B, described in detail in the descriptions of FIGS. 1B, 1B' and 27F, infra. Each storage member sidewall 11A has a fluidic composition-exiting orifice there through, 20A and 20B proximate the storage member base. Thus, each of the internal storage 3-spaces is bounded by (i) a planar storage member base, (ii) a storage member sidewall 11A and (iii) a planar storage member lid 13A and 13B;

(b) Atop a section of each of the storage member lids 13A and 13B, and covering a substantial surface area thereof is an upright hollow mixing chamber 14 having a horizontally-disposed planar mixing chamber base juxtaposed in its entirety with each of the planar storage member lids 13A and 13B and having a mixing chamber circumferential edge. Extending upwardly from the entirety of the mixing chamber base circumferential edge is a substantially vertically-disposed continuous liquid-impermeable mixing chamber sidewall terminating at its upper end at a mixing chamber upper horizontally-disposed planar lid 18 having an orifice there through, said orifice having a mixing chamber upper inner orifice rim 19. The mixing chamber sidewall has two spaced mixing chamber fluidic composition entry orifices there through 15A and 15B;

(c) Abutting the entirety of the mixing chamber upper orifice rim 19 in a liquid-tight manner is a hollow substantially frusto-conical cap member 16 having a substantially planar horizontally-disposed upper cap base 17 having an upper cap base circumferential edge. Air vent 1B, described in detail in the detailed description of FIGS. 1B, 1B' and 27F, infra, is shown to be contained in the upper cap base. Extending downwardly from the upper cap base circumferential edge, a substantially continuous substantially vertically-disposed cap sidewall terminating at and abutting the upper circumferential rim 19 of the mixing member 14; and (d) Two vertically disposed storage member-mixing chamber fluidic composition elastically deformable communication tubes 12A and 12B each of which tube extends in a substantially vertical direction from and connects with the fluidic composition exiting orifice 20A and 20B, respectively, of a storage member 6A and 6B, respectively, to one fluidic composition entry orifice 15A and 15B, respectively, of the mixing member adjacent to and abutting the outer side of said storage member sidewall 11A. Each communication tube 12A and 12B is shown to contain a one-way check valve, 1A, described in detail in the detailed description of FIG. 1A, infra. FIG. 1 illustrates the vertically-positioned parallel fluidic composition communication tubes 12A and 12B located at the front of the container 10. FIGS. 2, 3, 4A and 4B illustrate the vertically-positioned parallel fluidic composition tubes 12A and 12B located at opposite external sides of container 10.

Figure 4A:
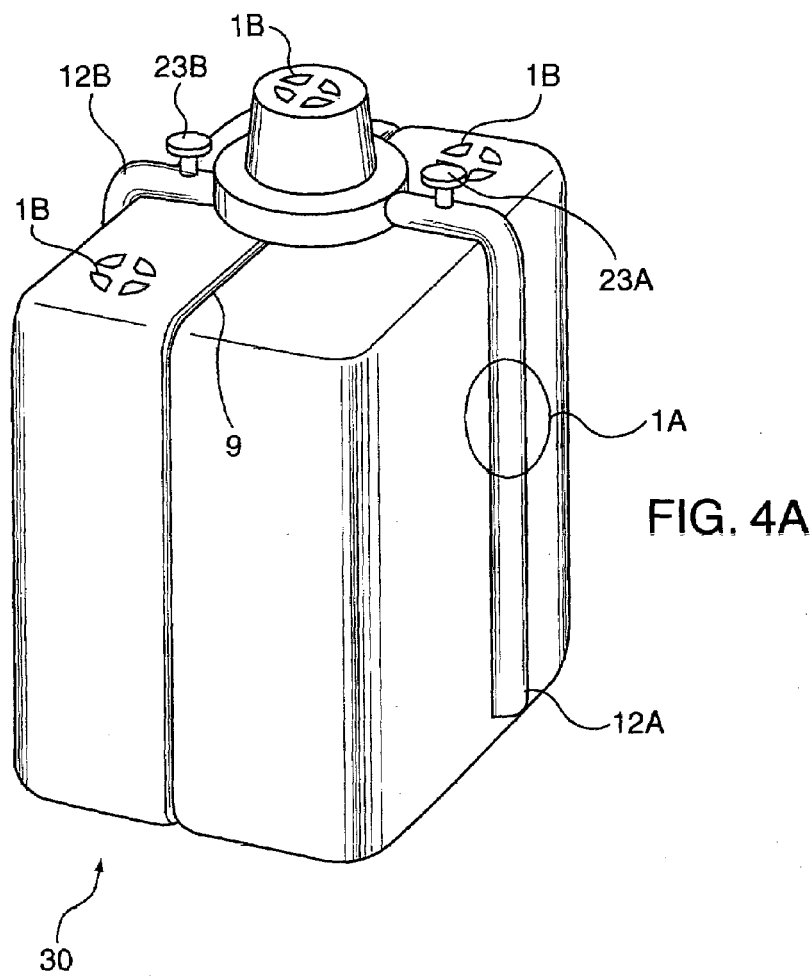
Figure 4B:
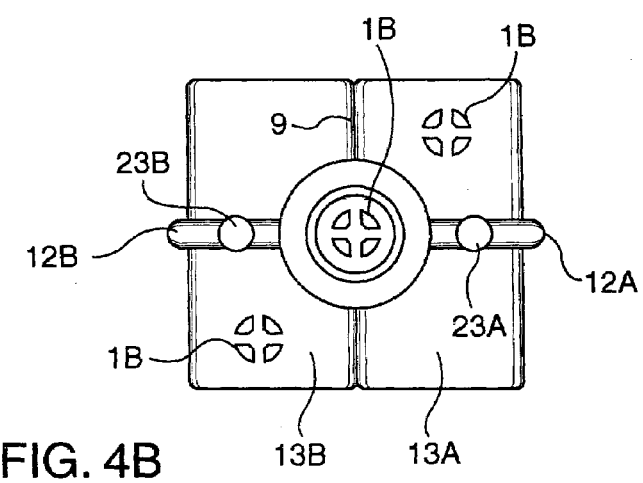
FIG. 4B is a top view of the storage and delivery container of FIG. 4A.

Thus, when external manual pressure is exerted on a given storage member sidewall 11A where the storage member contains a fluidic composition, the fluidic composition will flow from the storage member 3-space (inner three-dimensional volume) through the fluid communication tube 12A and 12B from a location at the storage member sidewall exiting orifice 20A and 20B, past the corresponding mixing chamber fluidic composition entry orifice 15A and 15B into the mixing chamber 14. Referring specifically to FIGS. 3, 4A and 4B each of the storage member-mixing chamber fluidic composition communication tubes 12A and 12B is shown to contain flow rate control valves 23A and 23B, respectively.

The one-way fluidic composition check valve of FIG. 1A is shown in the articles of FIGS. 1, 2, 3, 4A, 4B, 6, 8, 10 and 11 to be contained in fluidic composition communication tubes 12A and 12B (FIGS. 1, 2, 3, 4A and 4B); communication tubes 12C, 12D and 12E (FIG. 6 described infra); communication tubes 12H and 12J (FIG. 8 described infra); communication tubes 12L and 12M (FIG. 10 and FIG. 11 described infra) as indicated therein by reference 1A. The one-way fluidic composition check valve of FIG. 1A is also shown in FIG. 27A and 27B, described infra, to be contained in fluidic composition communication tubes 609A and 609B as indicated by reference numerals 607A and 607B in FIGS. 27A and 27B. The check valve of FIG. 1A is also described in detail in U.S. Pat. No. 3,760,986. Specifically, the check valve of FIG. 1A consists of three dependent tubes: tube 21 (the outer check valve holding tube which also serves as the fluidic composition communication tube) static tube 22 and vertically reciprocating movable tube 32. Thus, tube 21 in FIG. 1A is equivalent to any one of fluid communication tubes 12A, 12B, 12C, 12D, 12E, 12H, 12J, 12L, 12M, 609A and 609B. The inner side of tube 21 is indicated by reference numeral 11. The check valve is thus composed of static inner tube 22, the outer wall of which is juxtaposed with the inner wall 11 of tube 21, and vertically-reciprocating movable tube 32, the outer wall of which is juxtaposed or abutting the inner wall of tube 22. Tube 22 has one constriction which has an internal diameter approximately 50% of the internal diameter of tube 22. Tube 32 has one constriction 34 which has an internal diameter of approximately 50% of the internal diameter of tube 32. Ball check 28 having a diameter of about 75% of the internal diameter of tube 22 rests at the point of constriction of tube 22 and, when the valve 1A is in closed position (when no flow of the fluidic composition is taking place) the ball 28 is held in place by a resilient spring 30. Ball check 36 having a diameter of about 75% of the internal diameter of tube 32 rests at on constriction 34 of tube 32 and is also held in place by a resilient spring when valve 1A is in closed position.

Figure 5:
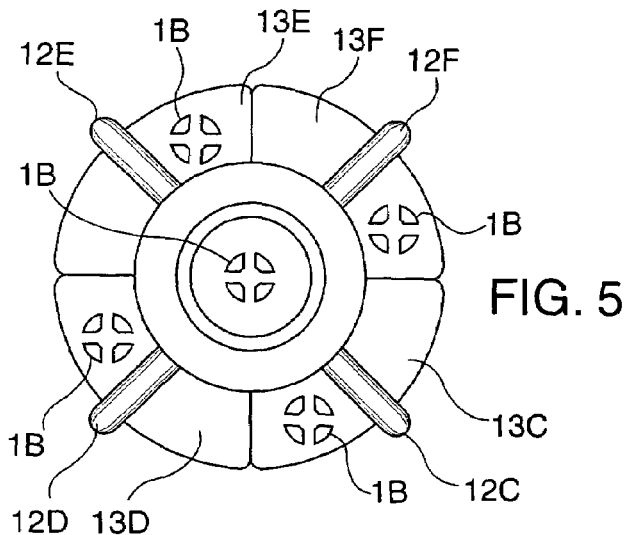
FIG. 5 is a top view of a third embodiment of the multi-compartment storage and delivery container of our invention, a tetra (4)-compartment storage and delivery container.
Figure 6:
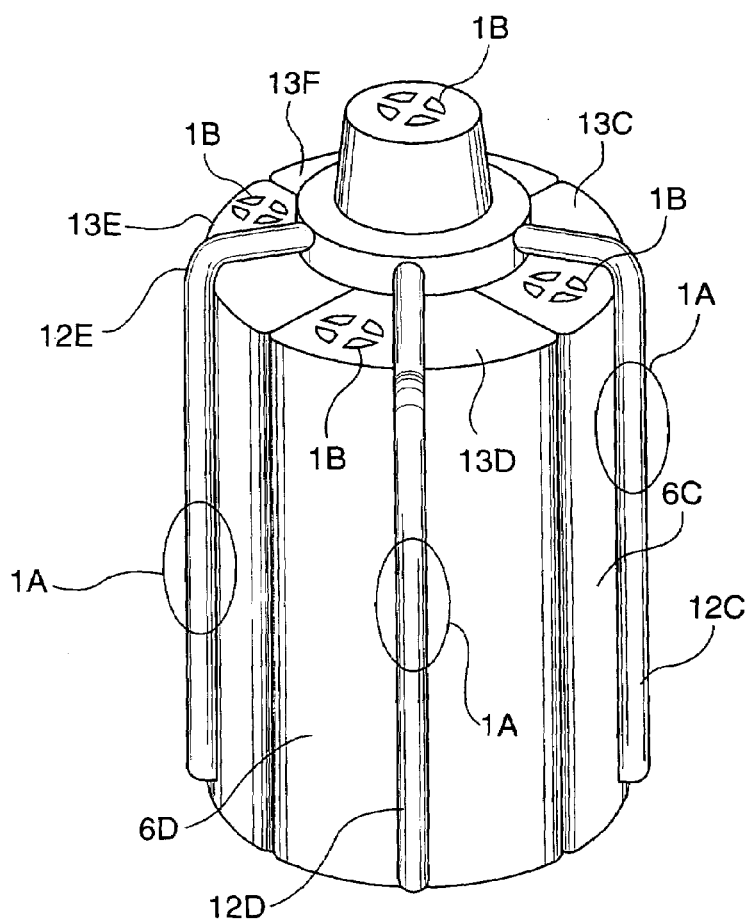
FIG. 6 is an upright perspective view of the storage and delivery container of FIG. 5.

The air vent of FIGS. 1B, 1B' and 27F is shown in the articles of FIGS. 1, 2, 3, 4A and 4B described supra (using the reference 1B); FIGS. 5, 6, 7, 8, 9 and 10 described infra (using the reference, 1B) and in FIGS. 27A, 27B, 27C and 28A described in detail, infra (using the reference, 27F) to be contained (i)in planar storage member lids 13A and 13B (as indicated in FIG. 1); 13D, 13E and 13F (as indicated in FIGS. 5 and 6); and 640A and 640B (as indicated in FIG. 27B and (ii) in the horizontally-disposed upper cap base 17 (using the reference, 1B as indicated in FIG. 1 described supra). The air vent of FIGS. 1B, 1B' and 27F is described in detail in U.S. application Ser. No. 2003/0168462 A1. Thus, air vent 4 provided in planar storage member lid 13 (as shown in FIG. 27F) has an air supply hole 4a penetrating the upper an lower surfaces of planar storage lid 13. In an opening on the upper face side of the air supply hole, 4a, a cross-shaped rib is provided to prevent foreign matter from entering the inner voids of the articles. The valve means indicated by reference numeral 5 in FIG. 1B' and indicated by reference numeral 710 in FIG. 27F is composed of a thin film-shaped valve element 710a formed of, for example silicone rubber and a needle-shaped protrusion 710b projectingly provided on the lower face of the cross-shaped rib 4b. The valve element 710a is formed into a cup shape. The top portion of the valve element 710a is formed with air hole 710c which is opened and closed by the protrusion 710b and a flange portion projectingly provided in the lower end portion of the valve element 710a is held between the lower end of the projecting portion and a pressing cap 711 mounted at the outer periphery of a projecting portion. In the bottom face of the pressing cap 711 is formed an opening 711a having a diameter approximately equal to the inside diameter of the projecting portion.

Referring to FIGS. 5 and 6 an article for effecting the dispensing of a mixture of four fluidic compositions each of which fluidic composition has a chemical constituency different from any other of the fluidic compositions and each of which fluidic composition is chemically and/or physically reactive with each of the other fluidic compositions when in intimate contact therewith over a finite period of time, the article has:

(a) four upright hollow storage members 6C, 6D, 6E and 6F vertically juxtaposed to one-another. Each storage member has an internal storage 3-space. Each storage member has a substantially horizontally-disposed substantially planar storage member base having a storage member base circumferential edge. Extending upwardly from the entirety of the storage member base circumferential edge is an elastically deformable vertically-disposed liquid-impermeable storage member sidewall having an outer side and an inner side, terminating at its upper end at the entirety of the circumferential edge of a substantially horizontally-disposed planar storage member lid 13C, 13D, 13E and 13F. Each lid is shown to contain an air vent, 1B, described in detail in the descriptions of FIGS. 1B, 1B' and 27F, supra. Each storage member sidewall has a fluidic composition-exiting orifice there through proximate the storage member base. Thus, each of the internal storage 3-spaces is bounded by (i) a planar storage member base, (ii) a storage member sidewall and (iii) a planar storage member lid 13C 13D, 13E and 13F;

(b) Atop a section of each of the storage member lids 13C 13D, 13E and 13F and covering a substantial surface area thereof is an upright hollow mixing chamber having a horizontally-disposed planar mixing chamber base juxtaposed in its entirety with each of the planar storage member lids 13C, 13D, 13E and 13F and having a mixing chamber circumferential edge. Extending upwardly from the entirety of the mixing chamber base circumferential edge is a substantially vertically-disposed continuous liquid-impermeable mixing chamber sidewall terminating at its upper end at a mixing chamber upper horizontally-disposed planar lid having an orifice there through, said orifice having a mixing chamber upper inner orifice rim. The mixing chamber sidewall has four spaced mixing chamber fluidic composition entry orifices there through;

(c) Abutting the entirety of the mixing chamber upper orifice rim in a liquid-tight manner is a hollow substantially frusto-conical cap member having a substantially planar horizontally-disposed upper cap base having an upper cap base circumferential edge. Air vent 1B, described in detail in the detailed description of FIGS. 1B, 1B' and 27F, supra, is shown to be contained in the upper cap base. Extending downwardly from the upper cap base circumferential edge, a substantially continuous substantially vertically-disposed cap sidewall terminating at and abutting the upper circumferential rim of the mixing chamber; and (d) Four vertically disposed storage member-mixing chamber fluidic composition elastically deformable communication tubes 12C, 12D, 12E and 12F each of which tube extends in a substantially vertical direction from and connects with the corresponding fluidic composition exiting orifice of a storage member 6C, 6D, 6E and 6F, respectively, to one fluidic composition entry orifice of the mixing member adjacent to and abutting the outer side of the corresponding storage member sidewall. Each communication tube 12C, 12D, 12E and 12F is shown to contain a one-way check valve, 1A, described in detail in the detailed description of FIG. 1A, supra.

Thus, when external manual pressure is exerted on a given storage member sidewall where the storage member contains a fluidic composition, the fluidic composition will flow from the storage member 3-space (inner three-dimensional volume) through the fluid communication tube 12C, 12D, 12E and 12F from a location at the storage member sidewall exiting orifice, past the corresponding mixing chamber fluidic composition entry orifice into the mixing chamber.

Figure 7:
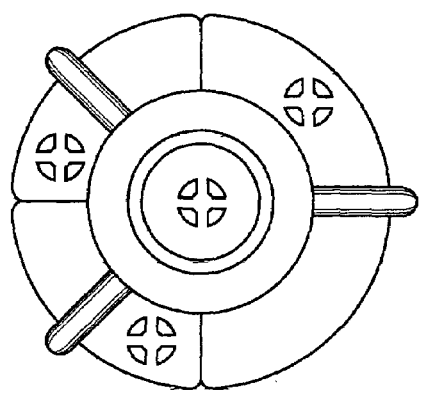
FIG. 7 is a top view of a fourth embodiment of the multi-compartment storage and delivery container of our invention, a tri (3)-compartment storage and delivery container.
Figure 8:
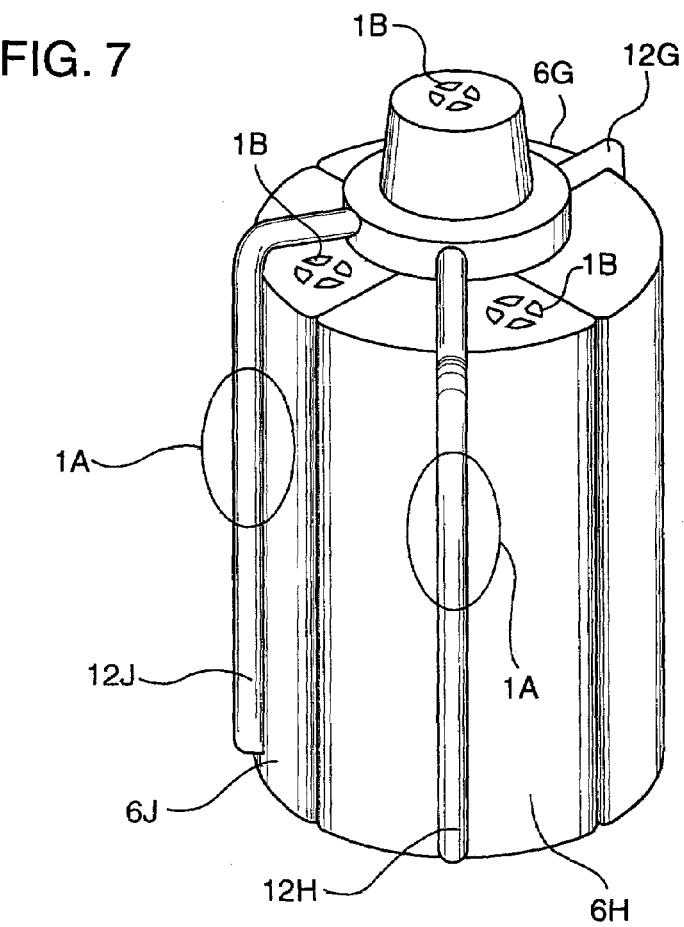
FIG. 8 is an upright perspective view of the storage and delivery container of FIG. 7.

Referring to FIGS. 7 and 8 an article for effecting the dispensing of a mixture of three fluidic compositions each of which fluidic composition has a chemical constituency different from any other of the fluidic compositions and each of which fluidic composition is chemically and/or physically reactive with each of the other fluidic compositions when in intimate contact therewith over a finite period of time, the article has:

(a) three upright hollow storage members 6G, 6H and 6J vertically juxtaposed to one-another. Each storage member has an internal storage 3-space. Each storage member has a substantially horizontally-disposed substantially planar storage member base having a storage member base circumferential edge. Extending upwardly from the entirety of the storage member base circumferential edge is an elastically deformable vertically-disposed liquid-impermeable storage member sidewall having an outer side and an inner side, terminating at its upper end at the entirety of the circumferential edge of a substantially horizontally-disposed planar storage member lid. Each lid is shown to contain an air vent, 1B, described in detail in the descriptions of FIGS. 1B, 1B' and 27F, supra. Each storage member sidewall has a fluidic composition-exiting orifice there through proximate the storage member base. Thus, each of the internal storage 3-spaces(or 'three-dimensional volumes') is bounded by (i) a planar storage member base, (ii) a storage member sidewall and (iii) a planar storage member lid;

(b) Atop a section of each of the storage member lids and covering a substantial surface area thereof is an upright hollow mixing chamber having a horizontally-disposed planar mixing chamber base juxtaposed in its entirety with each of the planar storage member lids and having a mixing chamber circumferential edge. Extending upwardly from the entirety of the mixing chamber base circumferential edge is a substantially vertically-disposed continuous liquid-impermeable mixing chamber sidewall terminating at its upper end at a mixing chamber upper horizontally-disposed planar lid having an orifice there through, said orifice having a mixing chamber upper inner orifice rim. The mixing chamber sidewall has three spaced mixing chamber fluidic composition entry orifices there through;

(c) Abutting the entirety of the mixing chamber upper orifice rim in a liquid-tight manner is a hollow substantially frusto-conical cap member having a substantially planar horizontally-disposed upper cap base having an upper cap base circumferential edge. Air vent 1B, described in detail in the detailed description of FIGS. 1B, 1B' and 27F, supra, is shown to be contained in the upper cap base. Extending downwardly from the upper cap base circumferential edge, a substantially continuous substantially vertically-disposed cap sidewall terminating at and abutting the upper circumferential rim of the mixing chamber; and (d) Three vertically disposed storage member-mixing chamber fluidic composition elastically deformable communication tubes 12G, 12H and 12J each of which tube extends in a substantially vertical direction from and connects with the corresponding fluidic composition exiting orifice of a storage member 6G, 6H and 6J, respectively, to one fluidic composition entry orifice of the mixing member adjacent to and abutting the outer side of the corresponding storage member sidewall. Each communication tube 12G, 12H and 12J is shown to contain a one-way check valve, 1A, described in detail in the detailed description of FIG. 1A, supra.

Thus, when external manual pressure is exerted on a given storage member sidewall where the storage member contains a fluidic composition, the fluidic composition will flow from the storage member 3-space (inner three-dimensional volume) through the fluid communication tube 12G, 12H and 12J from a location at the storage member sidewall exiting orifice, past the corresponding mixing chamber fluidic composition entry orifice into the mixing chamber.

Figure 9:
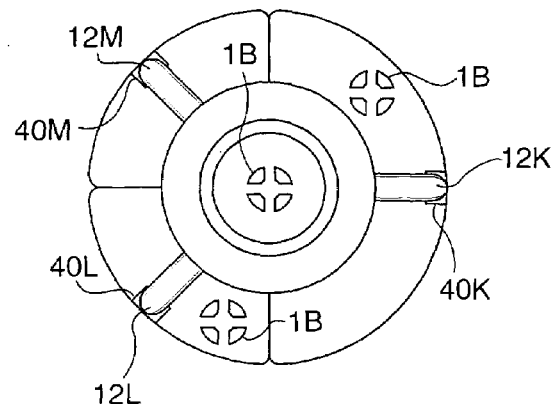
FIG. 9 is a top view of a fifth embodiment of the multi-compartment storage and delivery container of our invention, a tri(3)-compartment storage and delivery container wherein each compartment has an outer wall having a lengthwise vertical unbroken wall depression and a corresponding compartment lid depression and wherein each of the parallel fluidic composition communication tubes abuts a wall of a storage member and is fitted into a wall depression and corresponding compartment lid depression.
Figure 10:
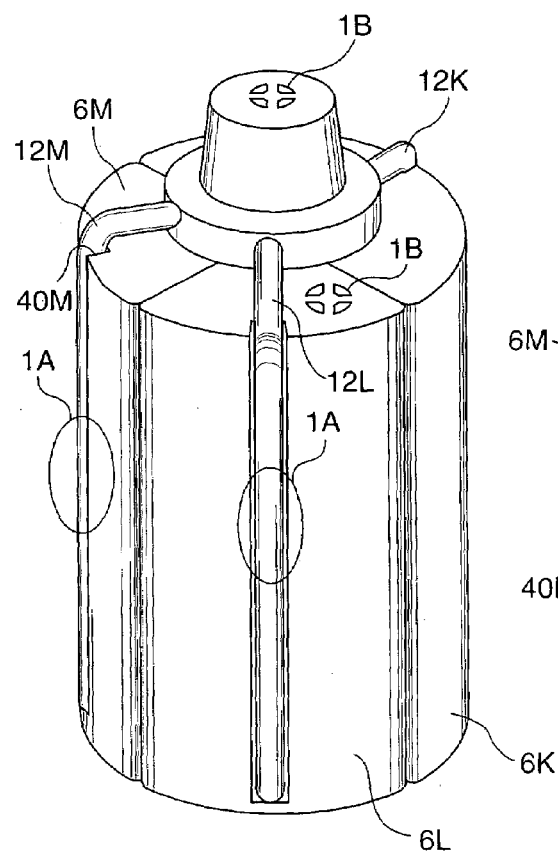
FIG. 10 is an upright perspective view of the storage and delivery container of FIG. 9.
Figure 11:
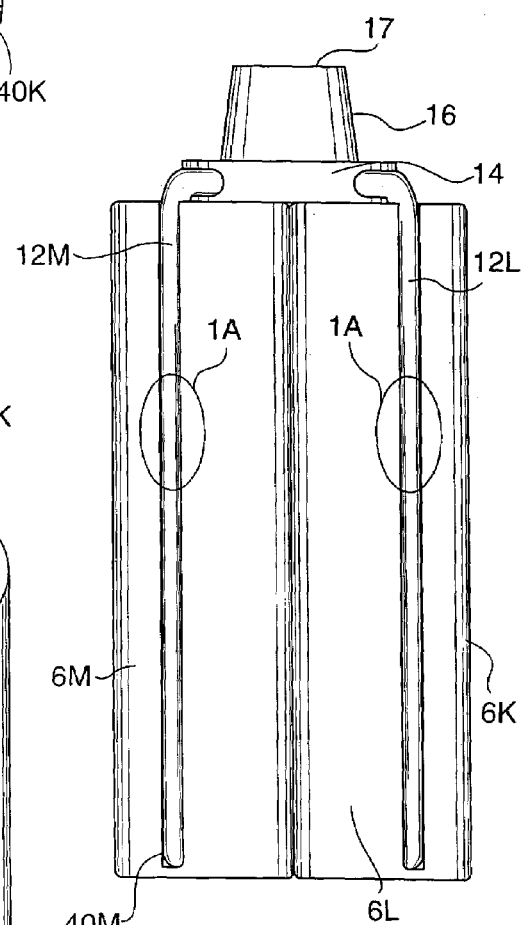
FIG. 11 is a front elevation view of the storage and delivery container of FIG. 9.

Referring to FIGS. 9, 10 and 11 an article for effecting the dispensing of a mixture of three fluidic compositions each of which fluidic composition has a chemical constituency different from any other of the fluidic compositions and each of which fluidic composition is chemically and/or physically reactive with each of the other fluidic compositions when in intimate contact therewith over a finite period of time, the article has:

(a) three upright hollow storage members 6K, 6L and 6M vertically juxtaposed to one-another. Each storage member has an internal storage 3-space. Each storage member has a substantially horizontally-disposed substantially planar storage member base having a storage member base circumferential edge. Extending upwardly from the entirety of the storage member base circumferential edge is an elastically deformable vertically-disposed liquid-impermeable storage member sidewall having an outer side and an inner side and having a lengthwise unbroken wall depression 40K, 40L and 40M having a diameter approximately 5% greater than the diameter of a fluidic composition communication tube described in part (d), infra, terminating at its upper end at the entirety of the circumferential edge of a substantially horizontally-disposed planar storage member lid. Each lid optionally has a depression corresponding to the aforementioned unbroken wall depression (as shown in FIG. 9 but not in FIG. 10 or FIG. 11) having a diameter approximately 5% greater than the diameter of the fluidic composition communication tube described in part (d), infra leading directly to a mixing chamber entry orifice, described infra. Each lid is shown to contain an air vent, 1B, described in detail in the descriptions of FIGS. 1B, 1B' and 27F, supra. Each storage member sidewall has a fluidic composition-exiting orifice there through proximate the storage member base. Thus, each of the internal storage 3-spaces (or 'three-dimensional volumes') is bounded by (i) a planar storage member base, (ii) a storage member sidewall and (iii) a planar storage member lid;

(b) Atop a section of each of the storage member lids and covering a substantial surface area thereof is an upright hollow mixing chamber 14 having a horizontally-disposed planar mixing chamber base juxtaposed in its entirety with each of the planar storage member lids and having a mixing chamber circumferential edge. Extending upwardly from the entirety of the mixing chamber base circumferential edge is a substantially vertically-disposed continuous liquid-impermeable mixing chamber sidewall terminating at its upper end at a mixing chamber upper horizontally-disposed planar lid having an orifice there through, said orifice having a mixing chamber upper inner orifice rim. The mixing chamber sidewall has three spaced mixing chamber fluidic composition entry orifices there through;

(c) Abutting the entirety of the mixing chamber upper orifice rim in a liquid-tight manner is a hollow substantially frusto-conical cap member 16 having a substantially planar horizontally-disposed upper cap base 17 having an upper cap base circumferential edge. Air vent 1B, described in detail in the detailed description of FIGS. 1B, 1B' and 27F, supra, is shown to be contained in the upper cap base. Extending downwardly from the upper cap base circumferential edge, a substantially continuous substantially vertically-disposed cap sidewall terminating at and abutting the upper circumferential rim of the mixing chamber; and (d) Three vertically disposed storage member-mixing chamber fluidic composition elastically deformable communication tubes 12K, 12L and 12M each of which tube extends within the aforementioned vertical wall depression 40K, 40L and 40M in a substantially vertical direction from and connects with the corresponding fluidic composition exiting orifice of a storage member 6K, 6L and 6M, respectively, to one fluidic composition entry orifice of the mixing member adjacent to and abutting the outer side of the corresponding storage member sidewall. Optionally, each lid has a corresponding depression for each fluidic composition communication tube leading to the corresponding mixing chamber entry orifice (as shown in FIG. 9; but not in FIG. 10 or FIG. 11). Each communication tube 12K, 12L and 12M is shown to contain a one-way check valve, 1A, described in detail in the detailed description of FIG. 1A, supra.

Thus, when external manual pressure is exerted on a given storage member sidewall where the storage member contains a fluidic composition, the fluidic composition will flow from the storage member 3-space (inner three-dimensional volume) through the fluid communication tube 12K, 12L and 12M from a location at the storage member sidewall exiting orifice, past the corresponding mixing chamber fluidic composition entry orifice into the mixing chamber.

FIGS. 27A, 27B, 27C, 27D, 27E, 28A, 28B and 28C illustrate, schematically, process steps employing the article 600 of our invention (specifically shown in FIGS. 27A and 27B, cut-away side elevation views of FIG. 3 taken along lines 27A-27A') and components thereof (specifically the cap member-compound adjustable orifice lid assembly shown in FIGS. 28A, 28B and 28C) wherein the separate pre-stored fluidic compositions, (i) a microencapsulated fragrance and/or benefit agent slurry suspension and (ii)a liquid fabric care composition, e.g. the liquid detergent, WISK® and/or the fabric softener SUAVITEL® (which, if admixed at temperatures of 37-42° C. interact with one-another over a given period of time (as shown in FIGS. 17, 18A, 18B, 24 and 25 described in detail, infra) are admixed and the mixture is promptly delivered to a fabric article in a washing machine device comprising the steps of:

(a) Providing a dis-assembled article of FIG. 3 whereby the cap member 604 which contains in its upper base vent 27F is removed from the mixing chamber upper circumferential rim 610A-610B in order to facilitate (i) entry of a microencapsulated fragrance and/or benefit agent slurry suspension into one compartment of the article illustrated in FIG. 27A at location 601 and (ii) entry of a liquid fabric care composition, e.g. the liquid detergent, WISK® and/or the fabric softener SUAVITEL® composition at location 602;

(b) at least partially filling (i) the storage member 3-space having inner wall 616A and planar storage member base 615A with a microencapsulated fragrance and/or benefit agent slurry suspension and (ii) the storage member 3-space having inner wall 616B and planar storage member base 615B with a liquid fabric care composition, e.g. the liquid detergent, WISK® and/or the fabric softener SUAVITEL® composition;

(c) completing assembly the article whereby (i) fluidic composition check valves 607A and 607B are placed in fluidic composition communication tubes 609A and 609B, respectively; (ii) a compound lid 660 (illustrated in detail in FIGS. 28A, 28B and 28C) (having orifices 659 which have adjustable diameters) covers the orifice in the mixing chamber (having internal mixing chamber void 630) upper horizontally-disposed planar lid; (iii) the cap member 604 having inner void 605 and an upper cap member base including air vent 27F therein is detachably attached at screw threads 610A-610B to the mixing chamber upper circumferential rim;

(d) applying manual pressure to the sidewall of each of the storage members containing a fluidic composition, thereby effecting fluid flow from the two storage member 3-spaces through fluidic composition communication tubes 609A and 609B past check valves 607A and 607B and fluidic composition flow control valves 608A and 608B into the mixing chamber 3-space, 630 thereby forming in said mixing chamber a mixture of (i) microencapsulated fragrance and/or benefit agent slurry suspension and (ii) a liquid fabric care composition, e.g. the liquid detergent, WISK® and/or the fabric softener SUAVITEL® (Pressure within and outside the article is equalized as a result of the presence of air vents 27F in each of the storage member lids 640A and 640B as shown in FIG. 27C);

(e) removing the cap member 604 from the article 600;

(f) transporting the resulting mixture 603 of (i) microencapsulated fragrance and/or benefit agent slurry suspension and (ii) a liquid fabric care composition, e.g. the liquid detergent, WISK® and/or the fabric softener SUAVITEL® into the inner void 606 of the cap member 604; and (g) dispensing the mixture 603 of (i) microencapsulated fragrance and/or benefit agent slurry suspension and (ii) a liquid fabric care composition, e.g. the liquid detergent, WISK® and/or the fabric softener SUAVITEL® from the cap member 604 into a washing machine 612 together with fabric article 613 (as shown in FIG. 27D).

Referring to FIGS. 28A, 28B and 28C, the compound lid 700 is composed of two lid members: lid member 750 having orifices 752A and 752B and lid member 751 having orifices 752C and 752D. Lid members 750 and 751 are co-circumferential and rotatable about pin 753, thereby permitting adjustment of the orifice openings prior to carrying out the mixing procedure are set forth supra. Maximum orifice areas are achieved when orifices 752C and 752B coincide, and, consequently when orifices 752A and 752D coincide. The compound lid orifice openings are adjusted prior to attachment of cap member 604 to the mixing chamber upper orifice rim via screw threads 610A-610B (shown in FIG. 28A).

Figure 12:
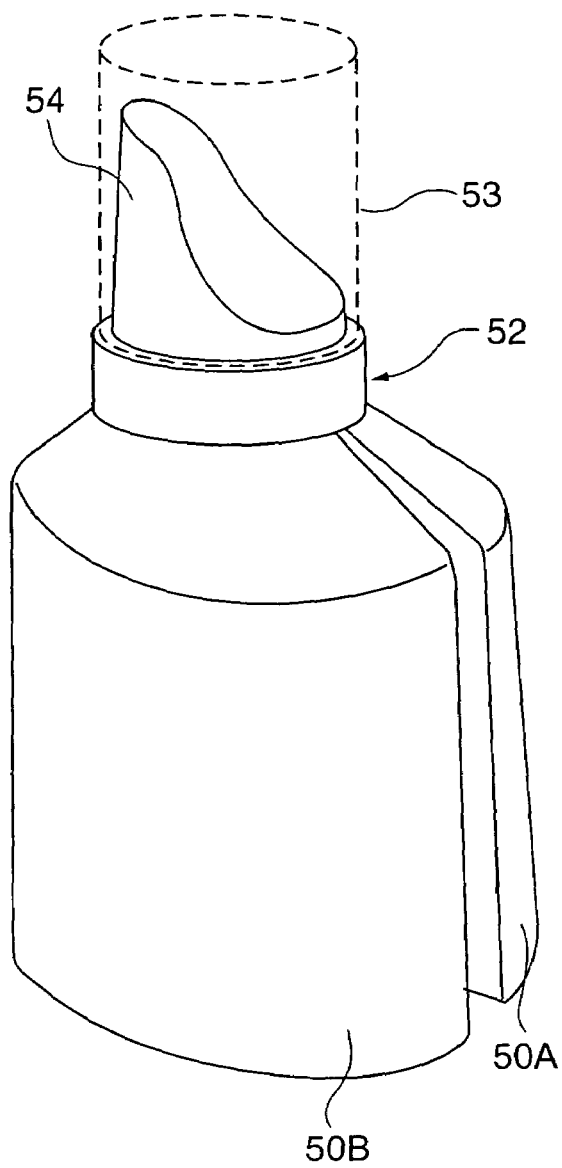
FIG. 12 is an upright perspective view of a first alternative embodiment of a dual-compartment storage and delivery container having side-by-side storage compartments useful in the practice of the process of our invention.
Figure 13:
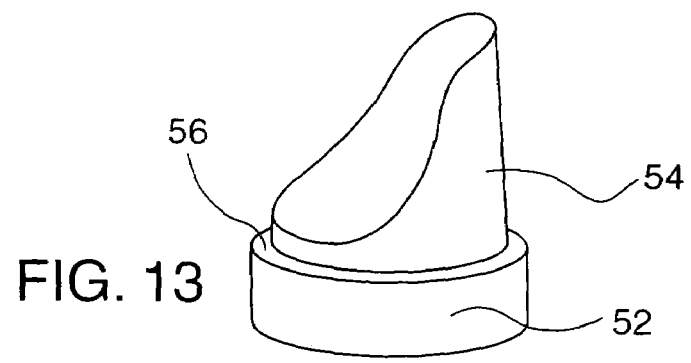
FIG. 13 is a detailed perspective view of the mixing chamber connected the spout of the dual-compartment storage and delivery container of FIG. 12.

The process of our invention can also be carried out using the dual compartment article illustrated in FIG. 12 using the cap member assembly ancillary to the FIG. 12 article illustrated in FIG. 13 and compound lid operation illustrated in FIGS. 13A, 13B and 13C. The dual compartment article of FIG. 12 has a compound entry and egress opening permitting filling of the container compartments separately and permitting egress of compositions from the compartments. Thus, into compartment 50A is placed (i) microencapsulated fragrance and/or benefit agent slurry suspension and into compartment 50B is placed (ii) a liquid fabric care composition, e.g. the liquid detergent, WISK® and/or the fabric softener SUAVITEL®. Prior to attachment of the cap member assembly to the co-joined compartments, the orifice areas of the compound lid are adjusted by rotating the upper lid member about pin 62. The compound lid, the top view of which is shown in FIGS. 13A, 13B and 13C, has two components: an upper member having orifices 59B and 60B and a lower member having orifices 59A and 60A. At maximum orifice area, orifices 59A and 59B coincide and, consequently, orifices 60A and 60B coincide as illustrated in FIG. 13C. The cap member assembly is then attached via screw thread or snap fitment attachment to the compound entry and egress opening. As the (i) microencapsulated fragrance and/or benefit agent slurry suspension and (ii) a liquid fabric care composition, e.g. the liquid detergent, WISK® and/or the fabric softener SUAVITEL® are poured from the compartments 50A and 50B, into, for example, a washing machine, mixing of the compositions occurs in spout 54 which is attached at location 56 to screw thread fitment or snap fitment 52. The article of FIG. 12 optionally may be fitted with a protective cap 53 to prevent internal cap member contamination during storage of the compositions.

Figure 14A:
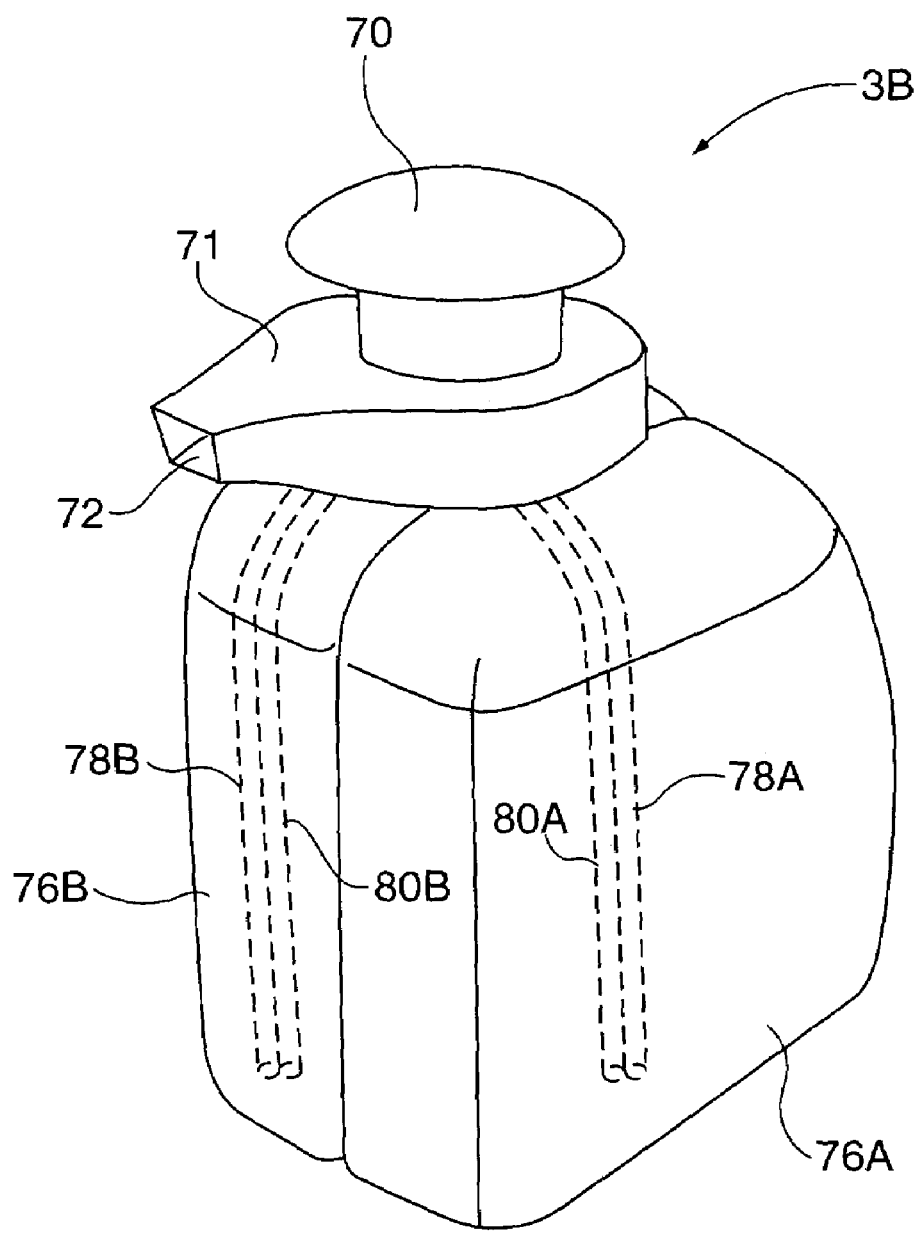
FIG. 14A is an upright perspective view of a second alternative embodiment of a dual-compartment storage and delivery container having side-by-side storage compartments and a manual vertical pump-type delivery system useful in the practice of the process of our invention.
Figure 14B:
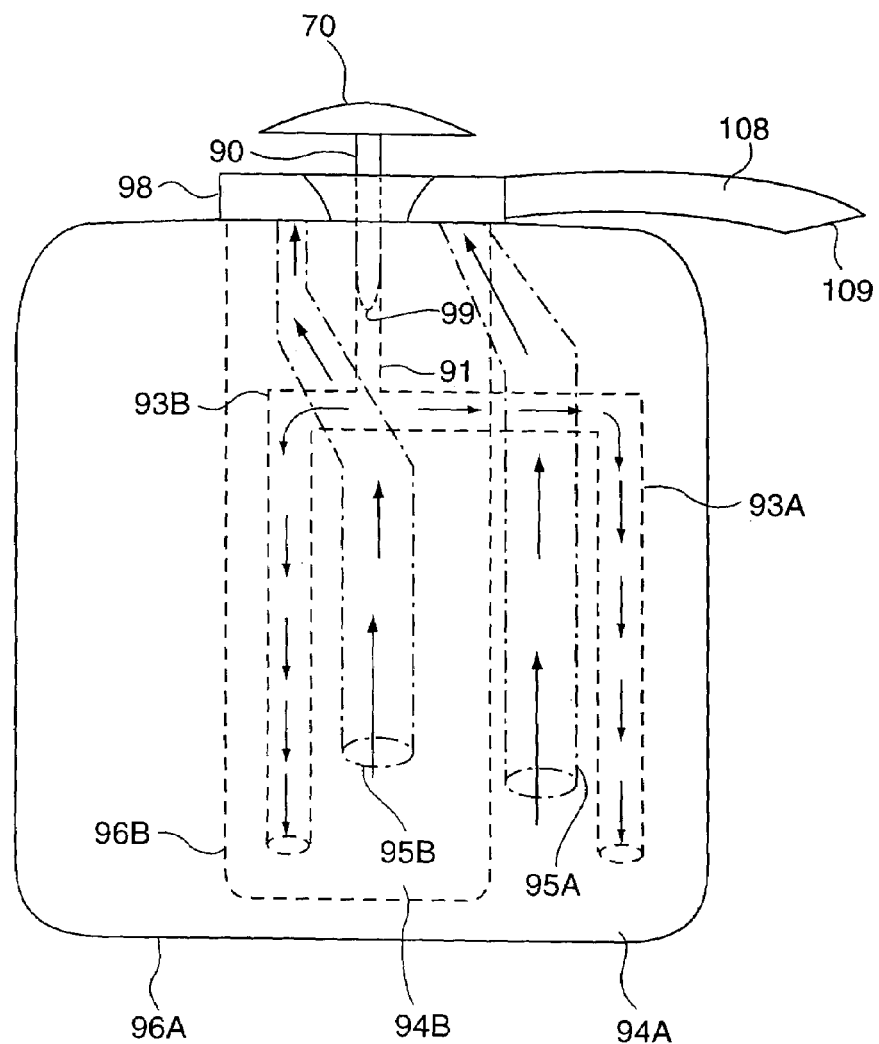
FIG. 14B is an upright perspective view of a third alternative embodiment of a dual-compartment storage and delivery container having concentric vertically-disposed cylindrical storage compartments and a manual 'vertical pump-type' delivery system useful in the practice of the process of our invention.

The process of our invention can also be carried out using the 'pump-type' dual compartment articles illustrated in FIGS. 14A and 14B. The dual compartment articles of FIGS. 14A and 14B each has a compound entry and egress opening permitting filling of the container compartments separately and permitting egress of compositions from the compartments. In employing the article of FIG. 14A in the process of our invention, into compartment 76A is placed (i) microencapsulated fragrance and/or benefit agent slurry suspension and into compartment 76B is placed (ii) a liquid fabric care composition, e.g. the liquid detergent, WISK® and/or the fabric softener SUAVITEL®. The pump/delivery assembly is then attached to the compound entry and egress opening. When pump handle 70 is engaged (that is downward pressure is applied thereto at 70) positive pressure through tubes 78A and 78B causes the microencapsulated fragrance and/or benefit agent slurry suspension to be transported through tube 80A and simultaneously causes the liquid fabric care composition, e.g. the liquid detergent, WISK® and/or the fabric softener SUAVITEL® to be transported through tube 80B with both compositions then mixing in mixing zone 71 and delivered through aperture 72 to, for example, a washing machine together with a fabric article to be treated. In employing the article of FIG. 14B, into compartment 94B having wall 96B is placed (i) microencapsulated fragrance and/or benefit agent slurry suspension and into compartment 94A having base 96A is placed (ii) a liquid fabric care composition, e.g. the liquid detergent, WISK® and/or the fabric softener SUAVITEL®. The pump/delivery assembly is then attached to the compound entry and egress opening. When pump handle 70/90 is engaged (that is downward hydraulic pressure is applied thereto at 70) positive pressure through tubes 91, 93A and 93B causes the microencapsulated fragrance and/or benefit agent slurry suspension to be transported through tube 95B and simultaneously causes the liquid fabric care composition, e.g. the liquid detergent, WISK® and/or the fabric softener SUAVITEL® to be transported through tube 95A with both compositions then flowing past location 98 and mixing in mixing zone 108 and delivered through aperture 109 to, for example, a washing machine together with a fabric article to be treated.

Figure 15:
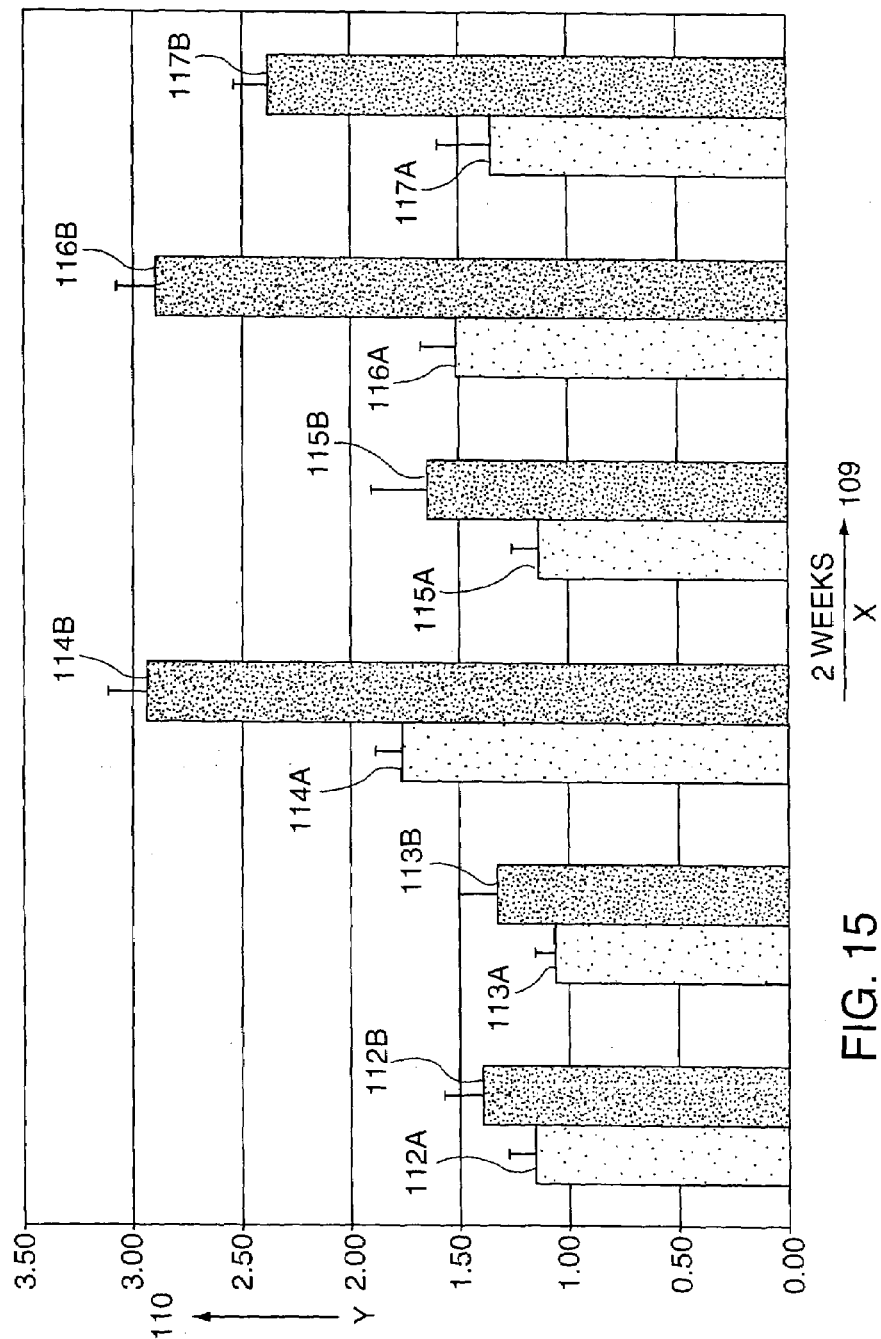

In FIG. 15, the set of bar graphs of perceived sensory intensity (on a scale of 0-5 as measured on the "Y" axis, indicated by reference numeral 110) for "pre-rub" (immediately after application of the suspension to fabric swatches, but before rubbing) is indicated by reference numerals 112A, 113A, 114A, 115A, 116A and 117A and "post-rub" (immediately after rubbing the fabric surface to which the suspension-containing base is applied) is indicated by reference numerals 112B, 113B, 114B, 115B, 116B and 117B. The bar graphs are arranged along the "X" axis, indicated by reference numeral 109. The bar graphs for the situation where a microencapsulated fragrance prepared according to Example B, infra, is formulated into a slurry suspension stored for a period of two weeks at a temperature of 25° C. at which time the suspension is admixed with liquid WISK® detergent and the resulting mixture is immediately applied to fabric swatches, are indicated by reference numerals 116A pre-rub; and 116B post-rub. The bar graphs for the situation where a microencapsulated fragrance prepared according to Example B, below is formulated into a slurry suspension stored for a period of two weeks at a temperature of 37° C. at which time the suspension is admixed with liquid WISK® detergent and the resulting mixture is immediately applied to fabric swatches are indicated by reference numerals 117A pre-rub and 117B post-rub. The bar graphs for the situation where mixtures of WISK® detergent and a microencapsulated fragrance prepared according to Example B, infra, are formulated into a slurry suspension stored for a period of two weeks at a temperature of 25° C. at which time the mixture is applied to fabric swatches are indicated by reference numerals 114A (pre-rub) and 114B (post-rub). The bar graphs for the situation where mixtures of WISK® detergent and a microencapsulated fragrance prepared according to Example B, infra, are formulated into a slurry suspension stored for a period of two weeks at a temperature of 37° C. at which time the mixture is applied to fabric swatches are indicated by reference numerals 115A (pre-rub) and 115B (post-rub). The bar graphs for the situation where a mixture of WISK® detergent and a neat fragrance prepared according to Example A, infra, is stored for a period of two weeks at a temperature of 25° C. at which time the mixture is applied to fabric swatches are indicated by reference numerals 112A (pre-rub) and 112B (post-rub). The bar graphs for the situation where a mixture of WISK® detergent and a neat fragrance prepared according to Example A, infra, is stored for a period of two weeks at a temperature of 37° C. at which time the mixture is applied to fabric swatches are. indicated by reference numerals 113A (pre-rub) and 113B (post-rub). In all cases, the mixtures are designed to give the equivalent of 1% fragrance.

Figure 16:
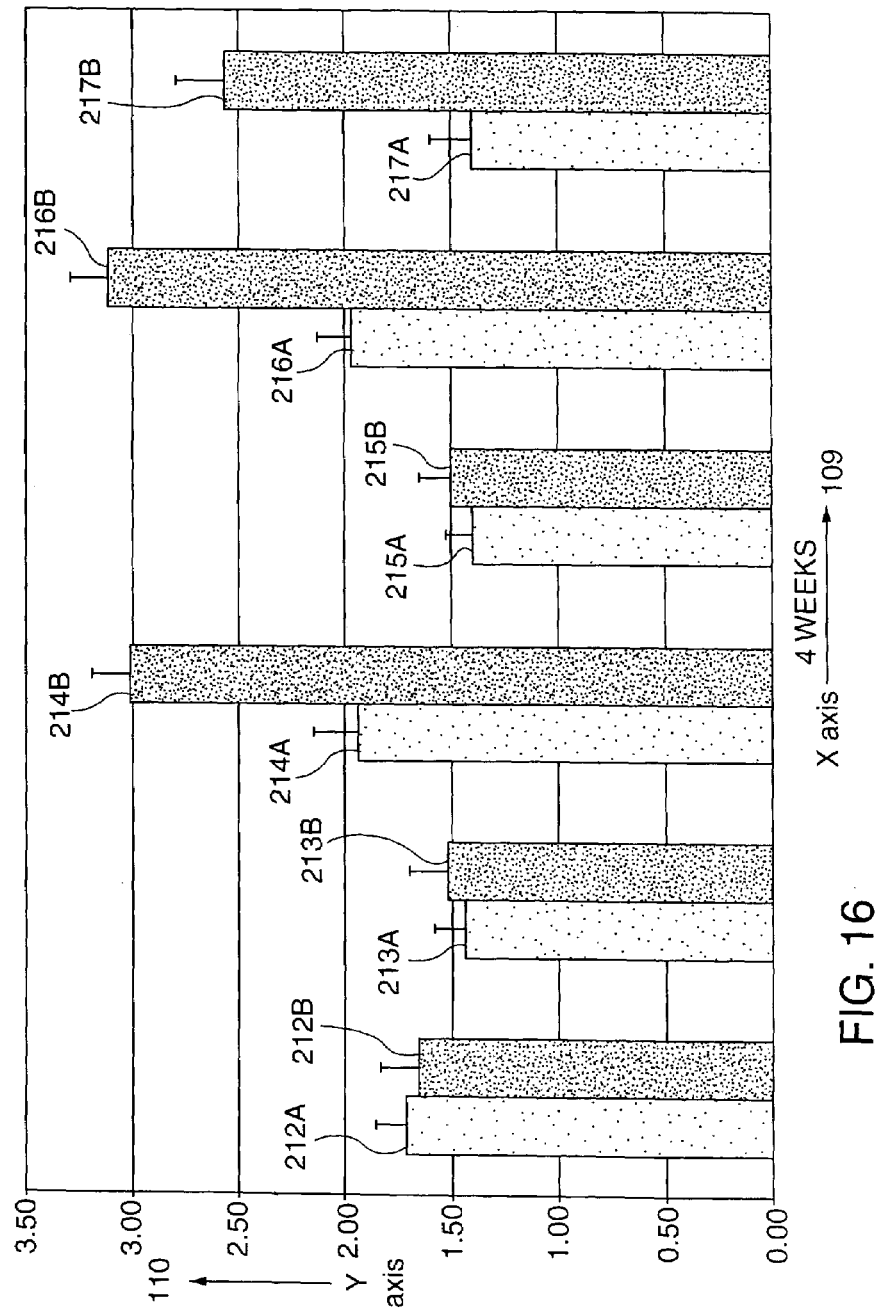

In FIG. 16, the set of bar graphs of perceived sensory intensity (on a scale of 0-5 as measured on the "Y" axis, indicated by reference numeral 110) for "pre-rub" (immediately after application of the suspension to fabric swatches, but before rubbing) is indicated by reference numerals 212A, 213A, 214A, 215A, 216A and 217A and "post-rub" (immediately after rubbing the fabric surface to which the suspension-containing base is applied) is indicated by reference numerals 212B, 213B, 214B, 215B, 216B and 217B. The bar graphs are arranged along the "X" axis, indicated by reference numeral 109. The bar graphs for the situation where a microencapsulated fragrance prepared according to Example B, infra, is formulated into a slurry suspension stored for a period of four weeks at a temperature of 25° C. at which time the suspension is admixed with liquid WISK® detergent and the resulting mixture is immediately applied to fabric swatches, are indicated by reference numerals 216A (pre-rub) and 216B (post-rub). The bar graphs for the situation where a microencapsulated fragrance prepared according to Example B, infra, is formulated into a slurry suspension stored for a period of four weeks at a temperature of 37° C. at which time the suspension is admixed with liquid WISK® detergent and the resulting mixture is immediately applied to fabric swatches are indicated by reference numerals 217A (pre-rub) and 217B (post-rub). The bar graphs for the situation where mixtures of WISK® detergent and a microencapsulated fragrance prepared according to Example B, infra, are formulated into a slurry suspension stored for a period of four weeks at a temperature of 25° C. at which time the mixture is applied to fabric swatches are indicated by reference numerals 214A (pre-rub) and 214B (post-rub). The bar graphs for the situation where mixtures of WISK® detergent and a microencapsulated fragrance prepared according to Example B, infra, are formulated into a slurry suspension stored for a period of four weeks at a temperature of 37° C. at which time the mixture is applied to fabric swatches are indicated by reference numerals 215A (pre-rub) and 215B (post-rub). The bar graphs for the situation where a mixture of WISK® detergent and a neat fragrance prepared according to Example A, infra, is stored for a period of four weeks at a temperature of 25° C. at which time the mixture is applied to fabric swatches are indicated by reference numerals 212A (pre-rub) and 212B (post-rub). The bar graphs for the situation where a mixture of WISK® detergent and a neat fragrance prepared according to Example A, infra, is stored for a period of four weeks at a temperature of 37° C. at which time the mixture is applied to fabric swatches are indicated by reference numerals 213A (pre-rub) and 213B (post-rub). In all cases, the mixtures are designed to give the equivalent of 1% fragrance.

In FIG. 17, the set of bar graphs of perceived sensory intensity (on a scale of 0-5 as measured on the "Y" axis indicated by reference numeral 109) for "post-rub" (immediately after rubbing the fabric surface to which the suspension-containing base is applied) is measured vs. time (in weeks) on the "x" axis, indicated by reference 111. The bar graphs for the situations where a microencapsulated fragrance prepared according to Example B, infra, in a slurry suspension is stored separately for periods of 0, 2 and 4 weeks at a temperatures of 37° C. at which time the suspension is admixed with liquid WISK® detergent and the resulting mixture is immediately applied to fabric swatches are indicated, respectively, by reference numerals 317, 117B and 217B. The bar graphs for the situations where mixtures of liquid WISK® detergent and a microencapsulated fragrance prepared according to Example B, infra, in a slurry suspension are stored for periods of 0, 2 and 4 weeks at a temperatures of 37° C. at which time the mixture is applied to fabric swatches are indicated, respectively, by reference numerals 315, 115B and 215B. The bar graphs for the situations where mixtures of liquid WISK® detergent and a neat fragrance prepared according to Example A, infra, are stored for periods of 0, 2 and 4 weeks at a temperature of 37° C. at which time the mixture is applied to fabric swatches are indicated, respectively, by reference numerals 313, 113B and 213B. In all cases, the mixtures are designed to give the equivalent of 1% fragrance.

Figure 18A:
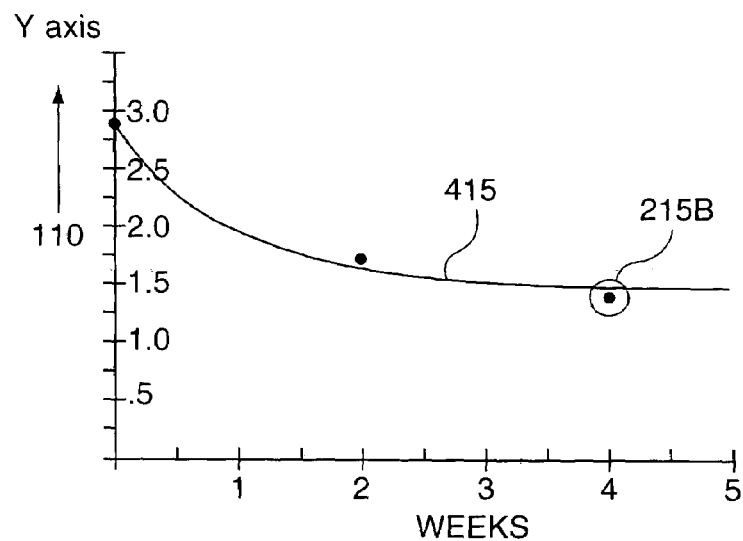
FIGS. 18A, 18B and 18C are graphs for the data of FIG. 17 with sensory intensity on the Y axis and time in weeks on the X axis.
Figure 18B:
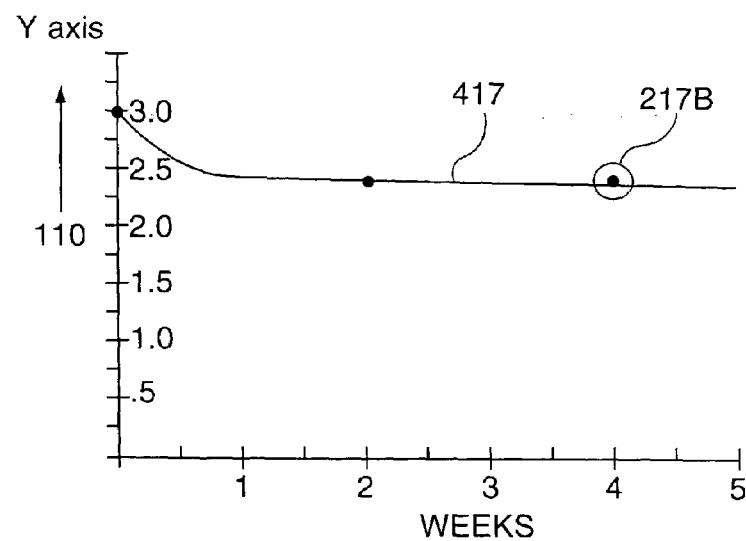
Figure 18C:
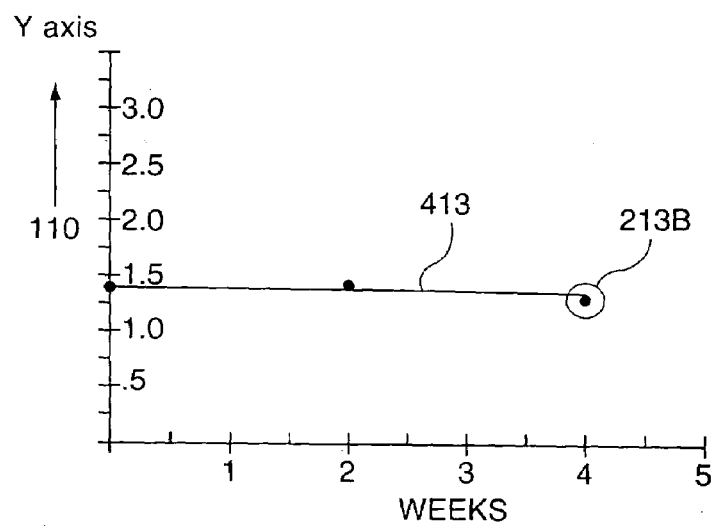

In FIGS. 18A, 18B and 18C each of the graphs are for the data of FIG. 17 with sensory intensity (on a scale of 0-5) on the "Y" axis (indicated by reference numeral 110) and time in weeks on the "X" axis (indicated by reference numeral 211). The regression algorithm for the situation where mixtures of liquid WISK® detergent and a microencapsulated fragrance are prepared according to Example B, infra, in a slurry suspension stored for periods of 0, 2 and 4 weeks at a temperatures of 37° C. at which time the mixture is applied to fabric swatches (with the results as set forth FIG. 18A, indicated by data point 215B and graph 415) is as follows:

$$Y=1.4e^{-X}+1.45$$

with a standard error of estimate=0.109. The regression algorithm for the situation where a microencapsulated fragrance prepared according to Example B, infra, in a slurry suspension is stored separately for periods of 0, 2 and 4 weeks at a temperatures of 37° C. at which time the suspension is admixed with liquid WISK® liquid detergent and the resulting mixture is immediately applied to fabric swatches (with the results as set forth in FIG. 18B, indicated by data point 217B and graph 417) is as follows:

$$Y=0.6e^{-3X}+2.4$$

with a standard error of estimate=0.02. The regression algorithm for the situation where mixtures of WISK® liquid detergent and a neat fragrance prepared according to Example A, infra, are stored for periods of 0, 2 and 4 weeks at a temperature of 37° C. at which time the mixtures are applied to fabric swatches (with results as set forth in FIG. 18C, indicated by data point 213B and graph 413) is as follows:

$$Y=0.013 \cdot LN(4-X)+1.387$$

with a standard error of estimate=0.006.

Figure 19:
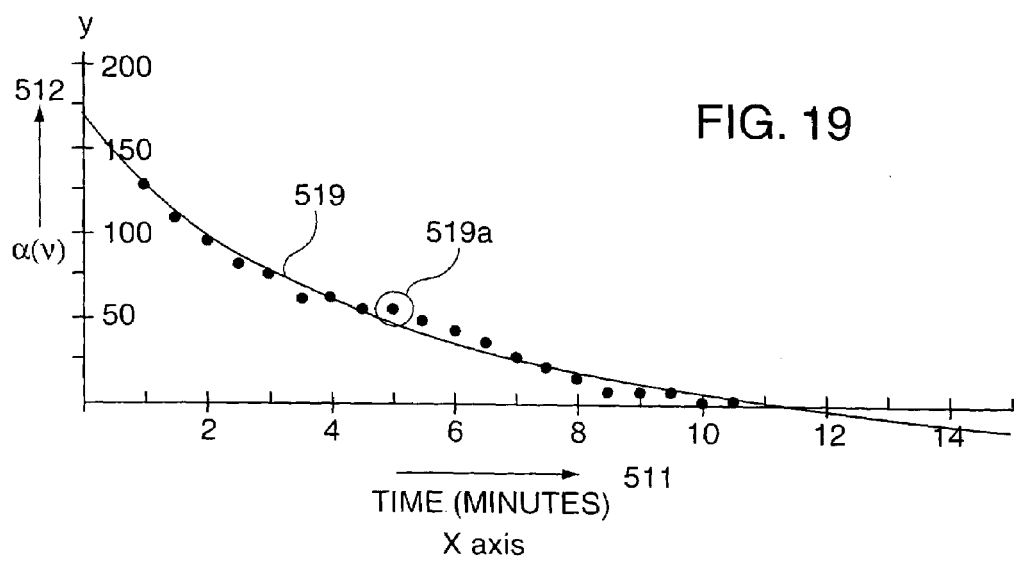
FIG. 19 is a graph of the viscosity function, (measured along the "Y" axis) for the microencapsulated fragrance, in a capsule slurry suspension vs. storage time (in minutes).

In FIG. 19 the graph of the viscosity function, $$\alpha(v) = (v-800)\left(\frac{T}{273}\right)$$

(measured along the "Y" axis indicated by reference numeral 512, wherein v is measured in centipoises using a model RV Brookfield Viscosimeter, Spindle:Vane-72, Speed: 30 rpm and temperature range: 19.83-19.90° C., and T is temperature in degrees Kelvin) for the microencapsulated fragrance of Example B, infra, in a capsule slurry suspension vs. storage time (θ) (in minutes) measured along the "X" axis (indicated by reference numeral 511) is indicated by reference numeral 519 showing sample data point 519a. The graph has 20 data pairs and shows a 'best-fit' regression function defined according to the algorithm:

$$(v-800)\left(\frac{T}{273}\right) = 80(2.45^{-0.34\theta} + 125 - 50 \cdot LN(\theta+2)$$

with a standard error of estimate=4.94.

Figure 20:
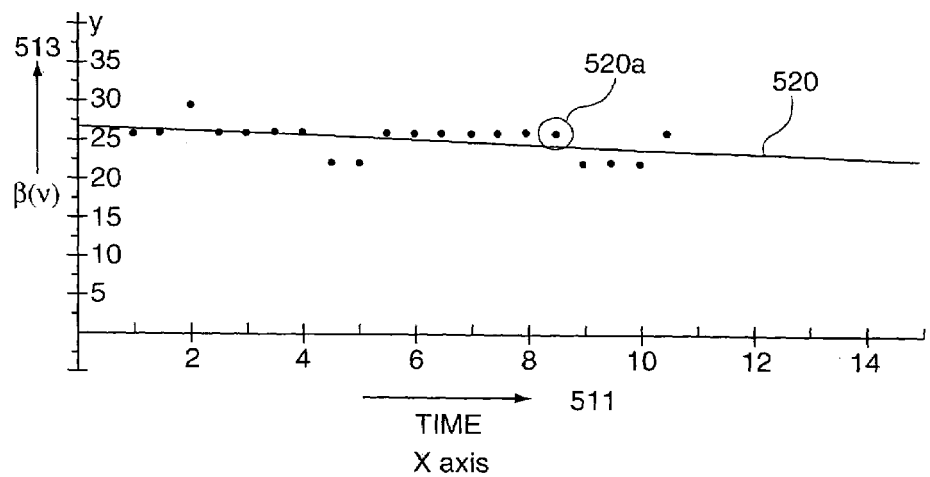
FIG. 20 is a graph of the viscosity function, (measured along the "Y" axis wherein v is measured in centipoises using a model RV Brookfield Viscosimeter, FIG. 21 is a graph of the viscosity function, on the "Y" axis, vs. storage time (θ) measured along the "X" axis.

In FIG. 20, the graph of the viscosity function, $$\beta(v) = (v-200)\left(\frac{T}{273}\right)$$

(measured along the "Y" axis, indicated by reference numeral 513, wherein v is measured in centipoises using a model RV Brookfield Viscosimeter, Spindle:Vane-72, Speed: 30 rpm and temperature range:21.28-21.35° C., and T is temperature in degrees Kelvin) for liquid WISK® detergent vs. storage time (θ) (in minutes) measured along the "X" axis (indicated by reference numeral 511) is indicated by reference numeral 520 with sample data point 520a. The graph has 20 data pairs and shows a 'best-fit' regression function defined according to the algorithm:

$$(v-200)\left(\frac{T}{273}\right) = -0.289\theta + 26.62$$

with a standard error of estimate=1.78.

Figure 21:
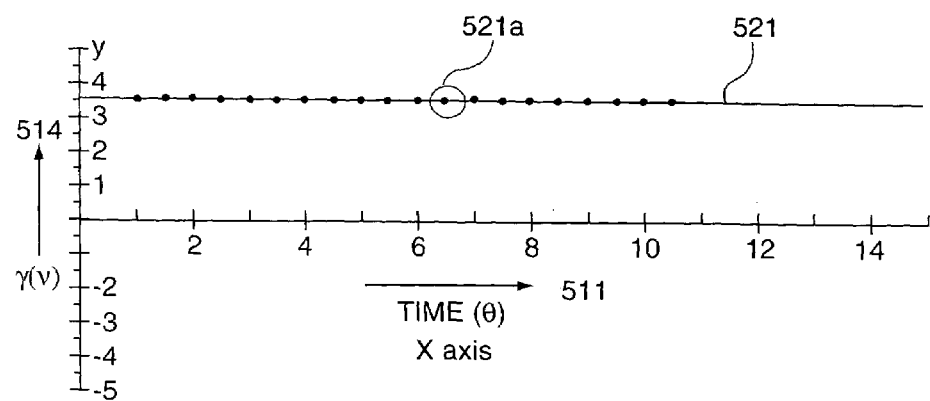

In FIG. 21, the graph of the viscosity function, $$\gamma(v) = (v-200)\left(\frac{T}{273}\right)$$

(measured along the "Y" axis, indicated by reference numeral 514, wherein v is measured in centipoises using a model RV Brookfield Viscosimeter, Spindle:Vane-72, Speed: 30 rpm and temperature range: 22.08-22.23° C., and T is temperature in degrees Kelvin) for liquid WISK® detergent pre-stored for a period of 2 days at 40° C. vs. storage time (θ) (in minutes) measured along the "X" axis (indicated by reference numeral 511) is indicated by reference numeral 521 with sample data point 521a. The graph has 20 data pairs and shows a 'best-fit' regression function defined according to the algorithm:

$$(v-200)\left(\frac{T}{273}\right) = 3.5$$

with a standard error of estimate=0.

Figure 22:
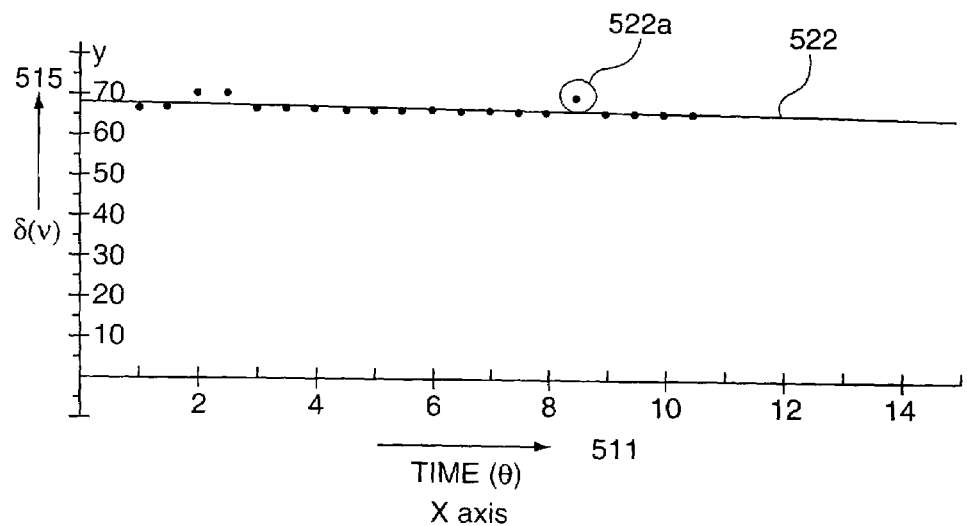
FIG. 22 is a graph of the viscosity function, the "Y" axis vs. storage time measured along the "X" axis.

In FIG. 22 the graph of the viscosity function, $$\delta(v) = (v-200)\left(\frac{T}{273}\right)$$

(measured along the "Y" axis, indicated by reference numeral 515, wherein v is measured in centipoises using a model RV Brookfield Viscosimeter, Spindle:Vane-72, Speed: 30 rpm and temperature range:21.15-21.28° C., and T is temperature in degrees Kelvin) for a microencapsulated fragrance of Example B, infra, in a slurry suspension vs. storage time (θ) (in minutes) measured along the "X" axis (indicated by reference numeral 511) is indicated by reference numeral 522 with sample data point 522a. The graph has 20 data pairs and shows a 'best-fit' regression function defined according to the algorithm:

$$(v-200)\left(\frac{T}{273}\right) = -0.095\theta + 67.5$$

with a standard error of estimate=1.36.

Figure 23:
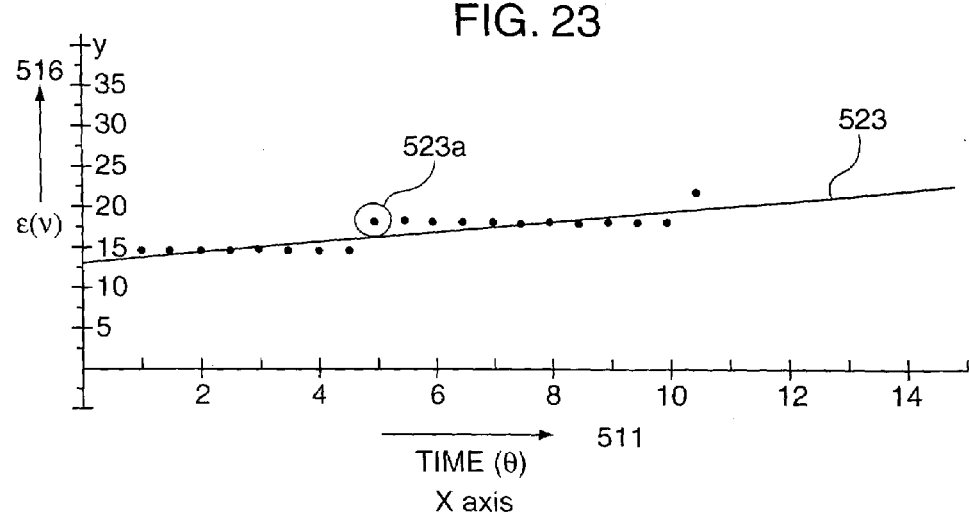
FIG. 23 is a graph of the viscosity function, for the microencapsulated fragrance of Example B, in a capsule slurry suspension pre-stored for a period of 2 days at 40° C. vs. storage time (θ) (in minutes) measured along the "X" axis.

In FIG. 23, the graph of the viscosity function, $$\varepsilon(v) = (v-200)\left(\frac{T}{273}\right)$$

(measured along the "Y" axis, indicated by reference numeral 516, wherein v is measured in centipoises using a model RV Brookfield Viscosimeter, Spindle:Vane-72, Speed: 30 rpm and temperature range:21.90-21.95° C., and T is temperature in degrees Kelvin) for a microencapsulated fragrance of Example B, infra, in a capsule slurry suspension pre-stored for a period of 2 days at 40° C. vs. storage time (θ) (in minutes) measured along the "X" axis (indicated by reference numeral 511) is indicated by reference numeral 523 with sample data point 523a. The graph has 20 data pairs and shows a 'best-fit' regression function defined according to the algorithm:

$$(v-200)\left(\frac{T}{273}\right) = 0.64\theta + 13.33$$

with a standard error of estimate=1.10.

Figure 24:
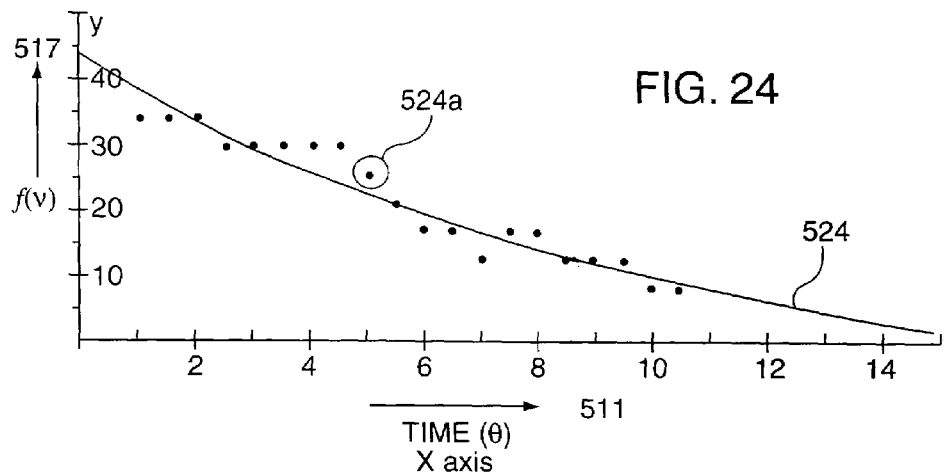
FIG. 24 is a graph of the viscosity function, measured along the "Y" axis vs. storage time (θ) (in minutes) measured along the "X" axis. The graph has 20 data pairs and shows a 'best-fit' regression function defined according to the algorithm.

In FIG. 24, the graph of the viscosity function, $$f(v) = (v-100)\left(\frac{T}{273}\right)$$

(measured along the "Y" axis, indicated by reference numeral 517, wherein v is measured in centipoises using a model RV Brookfield Viscosimeter, Spindle:Vane-72, Speed: 30 rpm and temperature range:40.48-40.65° C., and T is temperature in degrees Kelvin) for a microencapsulated fragrance of Example B, infra, in a capsule slurry suspension contained at a level of 1.71 weight % in WISK® liquid detergent vs. storage time (θ) (in minutes) measured along the "X" axis (indicated by reference numeral 511) is indicated by reference numeral 524 with sample data point 524a. The graph has 20 data pairs and shows a 'best-fit' regression function defined according to the algorithm:

$$(v-100)\left(\frac{T}{273}\right) = 47.27e^{-0.14\theta} - 1.62$$

with a standard error of estimate=2.89.

In FIG. 25, the graph of the viscosity function, $$g(v) = (v-80)\left(\frac{T}{273}\right)$$

(measured along the "Y" axis, indicated by reference numeral 518, wherein v is measured in centipoises using a model RV Brookfield Viscosimeter, Spindle:Vane-72, Speed: 30 rpm and temperature range:39.83-40.25° C., and T is temperature in degrees Kelvin) for microencapsulated fragrance of Example B, infra, in a capsule slurry suspension contained at a level of 1.71 weight % in WISK® liquid detergent vs. storage time (θ) (in minutes) measured along the "X" axis (indicated by reference numeral 511) is indicated by reference numeral 525 with sample data point 525a. The graph has 20 data pairs and shows a 'best-fit' regression function defined according to the algorithm:

$$(v-80)\left(\frac{T}{273}\right) = 17e^{-0.17\theta} + 26 - 7.5 \cdot LN(\theta + 1.7)$$

with a standard error of estimate=2.56.

In FIG. 26, the graph of the rate of change of viscosity with respect to time, $$\frac{\partial v}{\partial \theta}$$

(measured along the "Y" axis, indicated by reference numeral 617) as a function of time, θ, in minutes $$\left(\frac{\partial v}{\partial \theta} = \lambda(\theta)\right)$$

measured along the "X" axis, (indicated by reference numeral 611) for the microencapsulated fragrance of Example B, infra, in a capsule slurry suspension contained at a level of 1.71 weight % in WISK® liquid detergent using the data of FIGS. 24 and 25, is indicated by reference numeral 624. The graph 624 shows a 'best-fit' regression function defined according to the algorithm:

$$\frac{\partial v}{\partial \theta} = -1.26e^{-0.17\theta} - 1.14e^{-0.14\theta} - \left(\frac{32.68}{\theta + 1.7}\right) - \left(\frac{9.15}{\theta + 9}\right)$$

The following examples are not meant to define or otherwise limit the scope of the invention. Rather the scope of the invention is to be ascertained according to the claims that follow the examples. Unless noted to the contrary, all percentages are given on a weight percent on a dry basis.

EXAMPLE A

The Following Fragrance Composition was Prepared

| Fragrance Component | $C\log_{10}P$ value | Molecular Weight | Parts by Weight |
|---|---|---|---|
| ethyl undecylenate | 4.888 | 212.34 | 3.0 |
| geranyl anthranilate | 4.216 | 273.38 | 7.5 |
| α-irone | 3.820 | 206.33 | 6.3 |
| phenyl ethyl benzoate | 4.058 | 226.28 | 3.2 |
| d-limonene | 4.232 | 136.24 | 3.2 |
| cis-p-t-butylcyclohexyl acetate | 4.019 | 198.31 | 5.8 |
| amyl cinnamic aldehyde | 4.324 | 202.30 | 7.3 |
| hexyl cinnamic aldehyde | 5.473 | 216.33 | 12.6 |
| hexyl salicylate | 5.260 | 222.29 | 12.6 |

EXAMPLE B

Part 1-Preparation of Fragrance-containing Microcapsules 50 parts by weight of the fragrance of Example A was admixed with 50 parts by weight of NEOBEE-M5 solvent thereby forming a 'fragrance/solvent composition'. In a homogenizer fragrance/solvent composition-containing microcapsules were prepared by interfacial polymerization of a microcapsule wall encapsulating fragrance/solvent composition droplets. To make the capsule slurry, a copolymer of acrylamide and acrylic acid was first dispersed in water together with a methylated melamine-formaldehyde pre-condensate having the structure:

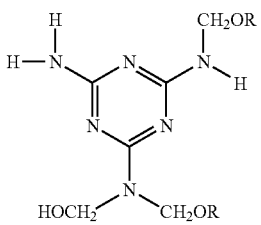

wherein one of the R moieties represents methyl and the other of the R moieties represents hydrogen. These two components were allowed to react under acidic conditions. The fragrance/solvent composition was then added into the solution and droplets of the desired size were achieved by high shear homogenization. Curing of the polymeric layer around the fragrance/solvent composition droplets was achieved by increasing the temperature to 50-85° C. The resulting capsule slurry contained 55% water, and 45% filled microcapsules (35% core consisting of 50% fragrance of Example A, and 50% NEOBEE M-5 and 10% microcapsule wall)

EXAMPLE B

Part 2

Preparation of Capsule Product Which Contains Both Encapsulated and Non-confined Fragrance An oil-in-water type emulsifier (TWEEN 20) was selected and added into neat fragrance oil prepared according to Example B, part 1, supra at 2.5 weight % using an overhead mixer. The emulsifier-containing neat fragrance oil was homogenized with the slurry of capsules having shell walls composed of an acrylamide-acrylic acid co-polymer cross-linked with melamine-formaldehyde resin as described in Example B, part 1, supra, using a high shear mixer. Emulsifier-containing fragrance oil was added into capsule slurry at a weight ratio such that 1 part free fragrance to 1 part encapsulated fragrance was achieved in the final capsule product, the stable suspension used in the following Example I.

EXAMPLE I

Part 1-Panel data (summarized in FIG. 15, described supra) was obtained for a set of bar graphs of perceived sensory intensity (on a scale of 0-5 as measured on the "Y" axis) for "pre-rub" (immediately after application of the suspension to towel fabric swatches, but before rubbing) and "post-rub" (immediately after rubbing the fabric surface to which the suspension-containing base was applied) for. (a) a microencapsulated fragrance prepared according to Example B, infra, in a slurry suspension stored for a period of two weeks at temperatures of 25° C. or 37° C. at which time the suspension was admixed with liquid WISK® detergent and the resulting mixture was immediately applied to fabric swatches; (b) mixtures of WISK® detergent and a microencapsulated fragrance prepared according to Example B, infra, in a slurry suspension stored for a period of two weeks at temperatures of 25° C. or 37° C. at which time the mixtures were separately applied to fabric swatches or (c) mixtures of WISK® detergent and a neat fragrance prepared according to Example A, supra, stored for a period of two weeks at temperatures of 25° C. or 37° C. at which time the mixtures were applied to fabric swatches. In all cases, the mixtures are designed to give the equivalent of 1% fragrance.

Part 2-Panel data (summarized in FIG. 16 described, supra) was obtained for a set of bar graphs of perceived sensory intensity (on a scale of 0-5 as measured on the "Y" axis) for "pre-rub" (immediately after application of the suspension to fabric swatches, but before rubbing) and "post-rub" (immediately after rubbing the fabric surface to which the suspension-containing base was applied) for. (a) a microencapsulated fragrance prepared according to Example B, infra, in a slurry suspension stored for a period of four weeks at temperatures of 25° C. or 37° C. at which time the suspension was admixed with liquid WISK® detergent and the resulting mixture was immediately applied to fabric swatches; (b) mixtures of WISK® detergent and a microencapsulated fragrance prepared according to Example B, supra, in a slurry suspension stored for a period of four weeks at temperatures of 25° C. or 37° C. at which time the mixture was applied to fabric swatches or (c) mixtures of WISK® detergent and a neat fragrance prepared according to Example A, infra, stored for a period of four weeks at temperatures of 25° C. or 37° C. at which time the mixture was applied to fabric swatches. In all cases, the mixtures are designed to give the equivalent of 1% fragrance.

Part 3-Panel data of FIGS. 15 and 16, described supra was included in a set of bar graphs (of perceived sensory intensity (on a scale of 0-5 as measured on the "Y" axis) for "post-rub" (immediately after rubbing the fabric surface to which the suspension-containing base is applied) for (a) a microencapsulated fragrance prepared according to Example B, infra, in a slurry suspension stored separately for periods of 0, 2 and 4 weeks at a temperatures of 37° C. at which time the suspension was admixed with liquid WISK® detergent and the resulting mixture is immediately applied to fabric swatches; (b) mixtures of liquid WISK® detergent and a microencapsulated fragrance prepared according to Example B, infra, in a slurry suspension stored for periods of 0, 2 and 4 weeks at a temperatures of 37° C. at which time the mixture was applied to fabric swatches or (c) mixtures of liquid WISK® detergent and a neat fragrance prepared according to Example A, infra, stored for periods of 0, 2 and 4 weeks at a temperature of 37° C. at which time the mixture was applied to fabric swatches. In all cases, the mixtures are designed to give the equivalent of 1% fragrance.

Part 4-Summaries of the data of FIG. 17 were prepared as shown in FIGS. 18A, 18B and 18C with sensory intensity (on a scale of 0-5) on the "Y" axis and time in weeks on the "X" axis. The regression algorithm for the situation where mixtures of liquid WISK® detergent and a microencapsulated fragrance prepared according to Example B, infra, in a slurry suspension were stored for periods of 0, 2 and 4 weeks at a temperatures of 37° C. at which time the mixtures were applied to fabric swatches (with the results as set forth FIG. 18A) is as follows:

$$Y=1.4e^{-X}+1.45$$

with a standard error of estimate=0.109. The regression algorithm for the situation where a microencapsulated fragrance prepared according to Example B, infra, in a slurry suspension was stored separately for periods of 0, 2 and 4 weeks at a temperatures of 37° C. at which time the suspension was admixed with liquid WISK® liquid detergent and the resulting mixture was immediately applied to fabric swatches (with the results as set forth in FIG. 18B) is as follows:

$$Y=0.6e^{-3X}+2.4$$

with a standard error of estimate=0.02. The regression algorithm for the situation where mixtures of WISK® liquid detergent and a neat fragrance prepared according to Example A, infra, were stored for periods of 0, 2 and 4 weeks at a temperature of 37° C. at which time the mixtures are applied to fabric swatches (with results as set forth in FIG. 18C) is as follows:

$$Y = 0.013 \cdot LN(4-X) + 1.387$$

with a standard error of estimate=0.006.

The results described in Part 4 indicate that at 37° C. unexpectedly advantageous results are obtained with respect to washed fabric aroma intensity when the surface treatment agent (that is, the liquid detergent) is kept separate from the microencapsulated fragrance slurry until that point in time when the slurry suspension-liquid detergent mixture is ready for use at which time a mixture is formed and delivered (via fabric application in a washing cycle); as opposed to storing a mixture of liquid detergent and slurry suspension for a relatively long period of time prior to fabric application in a washing cycle.

EXAMPLE II

Part 1-Data shown in FIG. 19 was obtained for a graph of the viscosity function, $$\alpha(v) = (v - 800)\left(\frac{T}{273}\right)$$

(measured along the "Y" axis wherein v was measured in centipoises using a model RV Brookfield Viscosimeter, Spindle: Vane-72, Speed: 30 rpm and temperature range: 19.83-19.90° C., and T is temperature in degrees Kelvin) for the microencapsulated fragrance of Example B, infra, in a capsule slurry suspension vs. storage time (θ) (in minutes) measured along the "X" axis. The graph has 20 data pairs and shows a 'best-fit' regression function defined according to the algorithm:

$$(v - 800)\left(\frac{T}{273}\right) = 80(2.45^{-0.34\theta} + 125 - 50 \cdot LN(\theta + 2)$$

with a standard error of estimate=4.94.

Part 2-Data shown in FIG. 20 was obtained for a graph of the viscosity function, $$\beta(v) = (v - 200)\left(\frac{T}{273}\right)$$

(measured along the "Y" axis wherein v is measured in centipoises using a model RV Brookfield Viscosimeter, Spindle: Vane-72, Speed: 30 rpm and temperature range:21.28-21.35° C., and T is temperature in degrees Kelvin) for liquid WISK® detergent vs. storage time (θ) (in minutes) measured along the "X" axis. The graph has 20 data pairs and shows a 'best-fit' regression function defined according to the algorithm:

$$(v - 200)\left(\frac{T}{273}\right) = -0.289\theta + 26.62$$

with a standard error of estimate=1.78.

Part 3-Data summarized in FIG. 21 was obtained for a graph of the viscosity function, $$\gamma(v) = (v - 200)\left(\frac{T}{273}\right)$$

(measured along the "Y" axis wherein v is measured in centipoises using a model RV Brookfield Viscosimeter, Spindle: Vane-72, Speed: 30 rpm and temperature range:22.08-22.23° C., and T is temperature in degrees Kelvin) for liquid WISK® detergent pre-stored for a period of 2 days at 40° C. vs. storage time (θ) (in minutes) measured along the "X" axis. The graph has 20 data pairs and shows a 'best-fit' regression function defined according to the algorithm:

$$(v - 200)\left(\frac{T}{273}\right) = 3.5$$

with a standard error of estimate=0.

Part 4-Data summarized in FIG. 22 was obtained for a graph of the viscosity function, $$\delta(v) = (v - 200)\left(\frac{T}{273}\right)$$

(measured along the "Y" axis wherein v is measured in centipoises using a model RV Brookfield Viscosimeter, Spindle: Vane-72, Speed: 30 rpm and temperature range:21.15-21.28° C., and T is temperature in degrees Kelvin) for the microencapsulated fragrance of Example B, infra, in a slurry suspension vs. storage time (θ) (in minutes) measured along the "X" axis. The graph has 20 data pairs and shows a 'best-fit' regression function defined according to the algorithm:

$$(v - 200)\left(\frac{T}{273}\right) = -0.095\theta + 67.5$$

with a standard error of estimate=1.36.

Part 5-Data summarized in FIG. 23 was obtained for a graph of the viscosity function, $$\varepsilon(v) = (v - 200)\left(\frac{T}{273}\right)$$

(measured along the "Y" axis wherein v is measured in centipoises using a model RV Brookfield Viscosimeter, Spindle: Vane-72, Speed: 30 rpm and temperature range:21.90-21.95° C., and T is temperature in degrees Kelvin) for the microencapsulated fragrance of Example B, infra, in a capsule slurry suspension pre-stored for a period of 2 days at 40° C. vs. storage time (θ) (in minutes) measured along the "X" axis.

The graph has 20 data pairs and shows a 'best-fit' regression function defined according to the algorithm:

$$(v-200)\left(\frac{T}{273}\right) = 0.64\theta + 13.33$$

with a standard error of estimate=1.10.

Part 6-Data summarized in FIG. 24 was obtained for a graph of the viscosity function, $$f(v) = (v-100)\left(\frac{T}{273}\right)$$

(measured along the "Y" axis wherein v is measured in centipoises using a model RV Brookfield Viscosimeter, Spindle: Vane-72, Speed: 30 rpm and temperature range:40.48-40.65° C., and T is temperature in degrees Kelvin) for the microencapsulated fragrance of Example B, infra, in a capsule slurry suspension contained at a level of 1.71 weight % in WISK® liquid detergent vs. storage time (θ) (in minutes) measured along the "X" axis. The graph has 20 data pairs and shows a 'best-fit' regression function defined according to the algorithm:

$$(v-100)\left(\frac{T}{273}\right) = 47.27 e^{-0.14\theta} - 1.62$$

with a standard error of estimate=2.89.

Part 7-Data summarized in FIG. 25 was obtained for a graph of the viscosity function, $$g(v) = (v-80)\left(\frac{T}{273}\right)$$

(measured along the "Y" axis wherein v is measured in centipoises using a model RV Brookfield Viscosimeter, Spindle: Vane-72, Speed: 30 rpm and temperature range:39.83-40.25° C., and T is temperature in degrees Kelvin) for the microencapsulated fragrance of Example B, infra, in a capsule slurry suspension contained at a level of 1.71 weight % in WISK® liquid detergent vs. storage time (θ) (in minutes) measured along the "X" axis. The graph has 20 data pairs and shows a 'best-fit' regression function defined according to the algorithm:

$$(v-80)\left(\frac{T}{273}\right) = 17 e^{-0.17\theta} + 26 - 7.5 \cdot LN(\theta + 1.7)$$

with a standard error of estimate=2.56.

Part 8-Using the data summarized in FIGS. 24 and 25, the graph of FIG. 26 was created illustrating the rate of change of viscosity with respect to time, $$\frac{\partial v}{\partial \theta}$$

as a function of time in minutes $$\left(\frac{\partial v}{\partial \theta} = \lambda(\theta)\right)$$

for the microencapsulated fragrance of Example B, infra, in a capsule slurry suspension contained at a level of 1.71 weight % in WISK® liquid detergent. The graph of FIG. 26 shows a 'best-fit' regression function defined according to the algorithm:

$$\frac{\partial v}{\partial \theta} = -1.26 e^{-0.17\theta} - 1.14 e^{-0.14\theta} - \left(\frac{32.68}{\theta + 1.7}\right) - \left(\frac{9.15}{\theta + 9}\right)$$

The results described in Part 1-8, inclusive of this Example II indicate that at 37° C. unexpectedly advantageous results are obtained with respect to washed fabric aroma intensity when the surface treatment agent (that is, the liquid detergent) is kept separate from the microencapsulated fragrance slurry until that point in time when the slurry suspension-liquid detergent mixture is ready for use at which time a mixture is formed and delivered (via fabric application in a washing cycle); as opposed to storing a mixture of liquid detergent and slurry suspension for a relatively long period of time prior to fabric application in a washing cycle.

INCORPORATION BY REFERENCE

The entire specification and claims of each of the U.S. Patents, U.S. Patent applications and U.S. Design patents herein referenced herein incorporated by reference as if set forth in their entirety.

What is claimed is:

1. An article for dispensing a mixture of a number of a number of fluidic compositions, said number being two to four, said fluidic compositions containing chemical constituencies different from each other and being chemically and/or physically reactive with each other when in contact, comprising:

said number of upright hollow storage members for storing said fluidic compositions vertically juxtaposed to one-another, each of the storage member members has a horizontally-disposed planar storage member base, an elastically deformable vertically-disposed liquid-impermeable storage member sidewall, and a horizontally-disposed planar storage member lid, wherein the storage member sidewall contains a fluidic composition-exiting orifice there through proximate the planar storage member base;

an upright hollow mixing chamber atop a section of the planar storage member lid and covering a substantial surface area thereof, the mixing chamber has a horizontally-disposed planar mixing chamber, a vertically disposed liquid-impermeable mixing chamber sidewall containing said number of spaced mixing chamber fluidic composition-entry orifices there through, and a mixing chamber upper horizontally-disposed planar lid containing an mixing chamber lid orifice there through, wherein the mixing chamber lid orifice contains a mixing chamber upper inner orifice rim;

a hollow cylindrical or frusto-conical cap member terminating at and abutting an entirety of the mixing chamber upper inner orifice rim in a liquid-tight manner, the cap member has a horizontally-disposed planar upper cap base and a vertically-disposed cap sidewall; and said number of elastically deformable vertically-disposed communication tubes, each of the tubes connects the fluidic composition-exiting orifice in each of the storage members to each of the fluidic composition-entry orifices abutting the outside of the storage member sidewall, whereby when pressure is exerted on a given storage member sidewall of a given storage member containing a given fluidic composition, the given fluidic composition will flow from the given storage member through fluidic composition-exiting orifice thereof, through a communication tube thereof and a fluidic composition-entry orifice thereof into the mixing chamber, and wherein an air vent is present in the planar storage member lid and/or the cap base; and wherein a fluid one-way check valve is contained in each of the communication tubes.

2. The article of claim 1, wherein each of the tubes further contains a flow rate control valve.

3. The article of claim 1, wherein each of the storage has members further contains a separate compartment wall, whereby the separate compartment wall and the planar storage member base have a thickness ranging from about 0.2 to about 0.5 cm; each of the storage members has a height ranging from about 10 to about 30 cm and a middle width ranging from about 5 to about 15 cm; the planar storage member base has a circumference ranging from about 10 to about 80 cm; the planar storage member lid has a circumference ranging from about 15 to about 80 cm; the mixing chamber base has a circumference ranging from about 10 to about 70 cm; the mixing chamber has a height ranging from about 1.5 to about 5 cm; the mixing chamber upper inner orifice rim has a circumference ranging from about 10 to about 70 cm; the cap member has a height ranging from about 4 to about 10 cm; the upper cap base has a circumference ranging from about 8 to about 20 cm; and each of the tubes has an internal diameter ranging from about 0.5 to about 2 cm.

4. The article of claim 1, wherein the mixture is dispensed with a process comprising the steps of:

providing the article, whereby the cap member is removed from the mixing chamber upper inner orifice rim in order to facilitate entering said fluidic compositions into said storage members;

providing said number of said fluidic compositions;

at least partially filling each of the storage members with each of said fluidic compositions;

attaching the cap member to the mixing chamber upper inner orifice rim;

exerting pressure on the given storage member sidewall to transport the given fluidic composition in the mixing chamber;

obtaining the mixing of said fluidic compositions;

removing the cap member;

transporting the mixture into the cap member; and dispensing the mixture from the cap member.

5. The article of claim 4, wherein said number is two and said fluidic compositions have a first fluidic composition and a second fluidic composition, whereby the first fluidic composition comprises an oxidizing agent and the second fluidic composition comprises a reducing agent.

6. The article of claim 4, wherein said number is two and said fluidic compositions have a first fluidic composition and a second fluidic composition, whereby the first fluidic composition comprises a sodium hypochlorite solution and the second fluidic composition comprises an aqueous slurry of microencapsulated fragrance.

7. The article of claim 4, wherein said number is two and said fluidic compositions have a first fluidic composition and a second fluidic composition, whereby the first fluidic composition comprises a personal care composition and the second fluidic composition comprises an aqueous slurry of microencapsulated fragrance.

8. The article of claim 4, wherein said number is two and said fluidic compositions have a first fluidic composition and a second fluidic composition, whereby the first fluidic composition comprises a surface treatment composition and the second fluidic composition comprises an aqueous slurry of microencapsulated fragrance.

9. The article of claim 8, wherein the surface treatment composition is selected from the group consisting of a liquid detergent composition and a liquid fabric softener composition.

10. The article of claim 4, wherein said number is two and said fluidic compositons have a first fluidic composition and a second fluidic composition, whereby the first fluidic composition comprises a pre-polymer and the second fluid composition comprises a solution of polymer curing agent 11. The article of claim 10, wherein the pre-polymer is a reaction product of epichlorohydrin and bis-phenol-A.

* * * * *